United States Patent
Liou et al.

(10) Patent No.: US 9,873,674 B2
(45) Date of Patent: Jan. 23, 2018

(54) C-REL INHIBITORS AND USES THEREOF

(71) Applicant: CORNELL UNIVERSITY, Ithaca, NY (US)

(72) Inventors: Hsiou-Chi Liou, New York, NY (US); Mei-Ling Liou, Germantown, MD (US); Samedy Ouk, San Diego, CA (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 14/429,874

(22) PCT Filed: Sep. 19, 2013

(86) PCT No.: PCT/US2013/060513
§ 371 (c)(1),
(2) Date: Mar. 20, 2015

(87) PCT Pub. No.: WO2014/047232
PCT Pub. Date: Mar. 27, 2014

(65) Prior Publication Data
US 2015/0218109 A1 Aug. 6, 2015

Related U.S. Application Data

(60) Provisional application No. 61/704,183, filed on Sep. 21, 2012.

(51) Int. Cl.
*A61K 31/515* (2006.01)
*C07D 239/62* (2006.01)
*C07D 239/66* (2006.01)

(52) U.S. Cl.
CPC .......... *C07D 239/66* (2013.01); *A61K 31/515* (2013.01); *C07D 239/62* (2013.01)

(58) Field of Classification Search
CPC ... C07D 239/62; C07D 239/66; A61K 31/515
USPC .................. 544/299, 300; 514/270
See application file for complete search history.

(56) References Cited

U.S. PATENT DOCUMENTS

| | | | |
|---|---|---|---|
| 3,764,321 A | 10/1973 | Kampfer et al. | |
| 5,705,188 A | 1/1998 | Junichi et al. | |
| 6,162,432 A | 12/2000 | Wallner et al. | |
| 2003/0229108 A1* | 12/2003 | De Belin | A61K 31/515 514/269 |
| 2005/0065066 A1* | 3/2005 | Kaarsholm | A61K 31/416 514/6.3 |
| 2007/0203236 A1* | 8/2007 | Smith | C07D 239/62 514/560 |
| 2010/0055116 A1* | 3/2010 | Liou | A61K 31/515 424/184.1 |

FOREIGN PATENT DOCUMENTS

| | | |
|---|---|---|
| GB | 922093 | 3/1963 |
| GB | 1 396 791 | 6/1975 |
| JP | 2003-313168 | * 11/2003 |
| WO | WO 93/08656 A1 | 4/1993 |
| WO | WO 97/30731 A2 | 8/1997 |
| WO | WO 02/69904 A2 | 9/2002 |
| WO | WO 02/098370 A2 | 12/2002 |
| WO | WO 2007/120842 A2 | 10/2007 |
| WO | WO 2009/059304 | * 5/2009 |
| WO | WO 2009/073620 | * 6/2009 |

OTHER PUBLICATIONS

Elben et al., CAPLUS Abstract 91:193283 (1979).*
Aripov et al., CAPLUS Abstract 108:216341 (1988).*
Gual, CAPLUS Abstract 101:207098 (1984).*
Guillen Sans et al., CAPLUS Abstract 110:219196 (1989).*
Singh et al., CAPLUS Abstract 116:235547 (1992).*
Swarup et al., CAPLUS Abstract 117:26481 (1992).*
Mohamed, CAPLUS Abstract 122:105831 (1995).*
Sastry et al., CAPLUS Abstract 122:89597 (1995).*
Andreani et al., CAPLUS Abstract 125:195499 (1996).*
Takahashi et al., CAPLUS Abstract 139:350644 (2003).*
Gura, Systems for identifying New Drugs Are Often Faulty, Cancer Models, Science, vol. 278, No. 5340, pp. 1041-1042, Nov. 1997.*
Johnson et al., Relationships between drug activity in NCI preclinical in vitro and in vivo models and early clinical trials, British Journal of Cancer (2001) 64(10): 1424-1431.*

(Continued)

*Primary Examiner* — Deepak Rao
(74) *Attorney, Agent, or Firm* — Scully Scott Murphy & Presser

(57) ABSTRACT

Compounds having a c-Rel inhibiting property according to the formula: (1) wherein $R^1$ and $R^2$ are each independently selected from hydrogen atom and hydrocarbon groups having at least one and up to thirty carbon atoms and optionally substituted with one or more heteroatoms selected from halogen, nitrogen, oxygen, and sulfur; $R^3$ is selected from hydrocarbon groups having at least one and up to thirty carbon atoms and optionally substituted with one or more heteroatoms selected from halogen, nitrogen, oxygen, and sulfur; and $X^1$, $X^2$, and $X^3$ are each independently selected from oxygen and sulfur atoms. Methods for treating diseases and conditions associated with c-Rel overexpression by administering compounds of Formula (1) or a pharmaceutical composition thereof to a subject afflicted with such a disease or condition are also described.

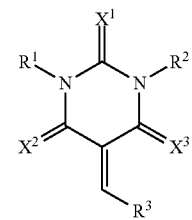

(1)

14 Claims, 9 Drawing Sheets

(56) References Cited

OTHER PUBLICATIONS

Pearce et al., Failure modes in anticancer drug discovery and development, Cancer Drug Design and Discovery Edited by Stephen Neidle, Chapter 18, pp. 424-435 (2008).*
Simone, Oncology: Introduction, Cecil Textbook of Medicine, 20th Edition, vol. 1, pp. 1004-1010, 1996.*
Machine Translation of JP 2003-313168 (2003).*
Akabori S., "1,3-Dimethylbarbituric Acid as an Aldehyde Reagent", *Berichte der Deutschen Chemischen Gesellschaft [Abteilung] B: Abhandlungen* 66B:139-143 (abstract) [online] Retrieved from STN, CA: 27:20579 (1933).
Akabori S., "Dimethylbarbituric Acid as an Aldehyde Reagent and a New Color Reaction of Furfuraldehyde", *Nippon Nagaku Kaishi (1921-47)* 52:601-605 (abstract) [online] Retrieved from STN, CA: 26:49167 (1931).
Ammirante M. et al., "B-Cell-Derived Lymphotoxin Promotes Castration-Resistant Prostate Cancer", *Nature* 464:302-306 (Mar. 11, 2010).
Annunziata C.M. et al., "Frequent Engagement of the Classical and Alternative NF-κB Pathways by Diverse Genetic Abnormalities in Multiple Myeloma", *Cancer Cell* 12:115-130 (Aug. 2007).
Bernal A. et al., "Survival of Leukemic B Cells Promoted by Engagement of the Antigen Receptor", *Blood* 98(10):3050-3057 (Nov. 15, 2001).
Bidere N. et al., "Casein Kinase 1α Governs Antigen-Receptor-Induced NF-κB Activation and Human Lymphoma Cell Survival", *Nature* 458:92-97 (Mar. 5, 2009).
Boehm J.S. et al., "Integrative Genomic Approaches Identify IKBKE as a Breast Cancer Oncogene", *Cell* 129:1065-1079 (Jun. 15, 2007).
Bogdanova et al., "Influence of Lipophilicity of Derivatives of Fullerene C60 on Their Ability to Inhibit Lipid Peroxidation in Aqueous Media", *Vestnik Moskovskogo Universiteta, Seriya 2: Khimiya* 53(4):241-245 (abstract) [online] Retrieved from STN, CA: 159:448925 (2012).
Bromberg J. et al., "Inflammation and Cancer: IL-6 and STAT3 Complete the Link", *Cancer Cell* 15:79-80 (Feb. 3, 2009).
Campbell I.K. et al., "Distinct Roles for the NF-κB1 (p50) and c-Rel Transcription Factors in Inflammatory Arthritis", *The Journal of Clinical Investigation* 105(12):1799-1806 (Jun. 2000).
Compagno M. et al., "Mutations of Multiple Genes Cause Deregulation of NF-κB in Diffuse Large B-Cell Lymphoma", *Nature* 459:717-722 (Jun. 4, 2009).
Criswell L.A., "Gene Discovery in Rheumatoid Arthritis Highlights the CD40/NF-κB Signaling Pathway in Disease Pathogenesis", *Immunological Reviews* 233:55-61 (2010).
Dox A.W. et al., "Condensation of Thiobarbituric Acid With Aromatic Aldehydes", *Journal of the American Chemical Society* 38:2164-2166 (abstract) [online] Retrieved from STN, CA: 10:14849 (1916).
Engler R., "Internal Corrosion of Holders", *American Gas Journal* 123:509-10, 519-20 (abstract) [online] Retrieved from STN, CA: 20:7976 (1925).
Finn P.W. et al., "Molecular Profiling of the Role of the NF-κB Family of Transcription Factors During Alloimmunity", *Journal of Leukocyte Biology* 72:1054-1062 (Nov. 2002).
Finn P.W. et al., "Inhibition of NF-κB-Dependent T Cell Activation Abrogates Acute Allograft Rejection", *The Journal of Immunology* 167:5994-6001 (2001).
Furman R.R. et al., "Modulation of NF-κB Activity and Apoptosis in Chronic Lymphocytic Leukemia B Cells", *The Journal of Immunology* 164:2200-2206 (2000).
Glas J. et al., "Novel Genetic Risk Markers for Ulcerative Colitis in the IL2/IL21 Region are in Epistasis With IL23R and Suggest a Common Genetic Background for Ulcerative Colitis and Celiac Disease", *The American Journal of Gastroenterology* 104:1737-1744 (2009).
Grivennikov S.I. et al., "Inflammation and Oncogenesis: A Vicious Connection", *Current Opinion in Genetics & Development* 20:65-71 (2010).
Hilliard B.A. et al., "Critical Roles of c-Rel in Autoimmune Inflammation and Helper T Cell Differentiation", *The Journal of Clinical Investigation* 110(6):843-850 (Sep. 2002).
Hitora K. et al., "Pyrimidine Derivatives and Related Compounds. 35 Synthesis and Analgesic Activity of Isoxazolo[3,4-d]Pyrimidines and Isothiazolo[5,4-d]Pyrimidines", *Nippon Kagaku Kaishi* 5:721-725 (abstract) [online] Retrieved from STN, CA: 95:25207a, 25210a (1981).
Keats J.J. et al., "Promiscuous Mutations Activate the Noncanonical NF-κB Pathway in Multiple Myeloma", *Cancer Cell* 12:131-144 (Aug. 2007).
Lamhamedi-Cherradi S-E et al., "Transcriptional Regulation of Type I Diabetes by NF-κB", *The Journal of Immunology* 171:4886-4892 (2003).
Márquez A. et al., "Novel Association of the Interleukin 2-Interleukin 21 Region With Inflammatory Bowel Disease", *The American Journal of Gastroenterology* 104:1968-1975 (Aug. 2009).
Wang Y. et al., "c-Rel is Essential for the Development of Innate and T Cell-Induced Colitis", *The Journal of Immunology* 180:8118-8125 (2008).
Yang H. et al., "Enforced c-Rel Deficiency Prolongs Survival of Islet Allografts", *Transplantation* 74(3):291-298 (Aug. 15, 2002).
STN Registry, compound with RN 905809-63-4 (Nov. 28, 2001).
STN Registry, compound with RN 372084-08-7 (Sep. 3, 2006).
International Search Report dated Mar. 27, 2014 received from Application No. PCT/US2013/060513.

* cited by examiner

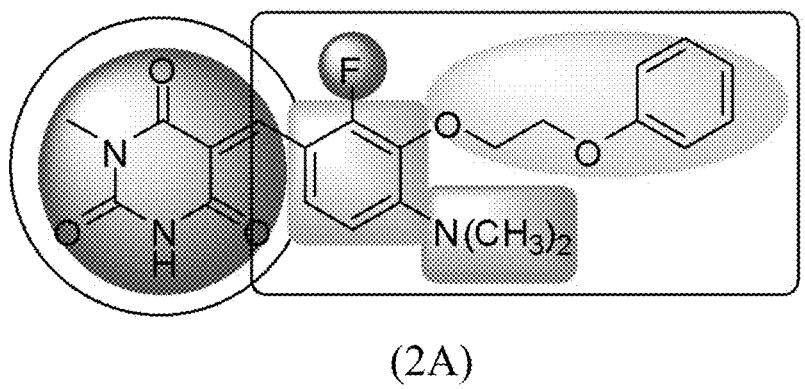
(2A)
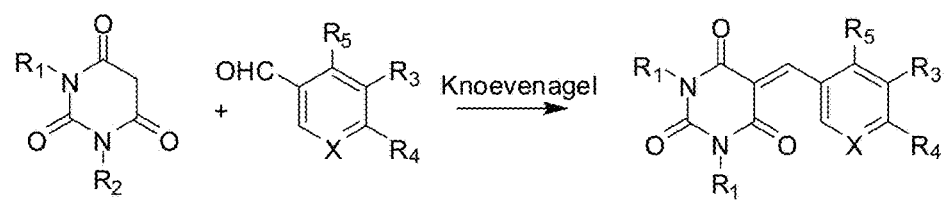
Examples of aldehyde to be reacted with barbituric acid
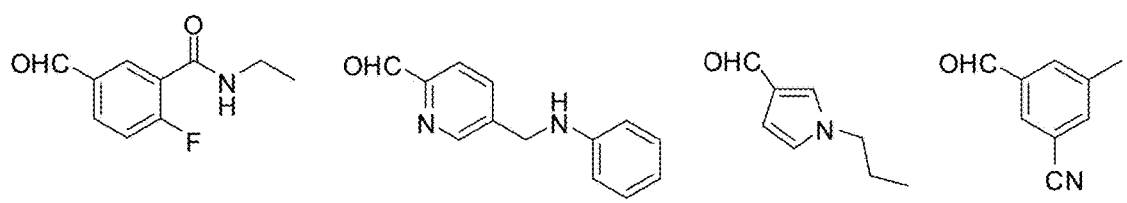
(2B)
FIGS. 2A, 2B

C-REL INHIBITORS AND USES THEREOF

CROSS-REFERENCE TO RELATED APPLICATIONS

This application claims priority from U.S. Provisional Application No. 61/704,183, filed Sep. 21, 2012, which is herein incorporated by reference in its entirety.

STATEMENT REGARDING FEDERALLY SPONSORED RESEARCH

This invention was made with government support under Contract No. GM086703 awarded by the National Institutes of Health. The government has certain rights in the invention.

FIELD OF THE INVENTION

This invention relates to compounds and pharmaceutically acceptable salts thereof having c-Rel inhibitory activities, and their use in the treatment of cancer, inflammation, autoimmune diseases, diabetes, transplant rejection, graft versus host disease, allergy, asthma, and bone loss.

BACKGROUND OF THE DISCLOSURE (I) The Rel Family c-Rel, cloned by Dr. Howard Temin's group in the 1980's, is the cellular homolog of the v-Rel oncogene encoded by the avian REV-T retrovirus. Subsequent cloning of NF-kB, p50 (NF-kB1) and p65 (RelA), in the early 1990's by Dr. David Baltimore's group identified the homology between NF-kB and c-Rel at the Rel Homologous Domain (RHD). Two other genes containing the RHD, p52 (NF-kB2) and RelB, were also identified by several groups. Hence, these five proteins are classified as the Rel transcription factor family. NF-kB and c-Rel are regulated by the "classical" pathway via the IKK$\alpha$/$\beta$/$\gamma$ kinase complex, whereas RelB and p52. (NF-kB2) are regulated by the "alternative" pathway via the IKK$\alpha$/NIK. Despite the similarity, each Rel member is distinct with regard to tissue expression pattern, response to receptor signals, and target gene specificity. These differences are evident from the non-redundant phenotypes exhibited by individual Rel knockout mouse. Thus, therapeutics targeted to different Rel members have different biological effects and safety/toxicity profiles.

C-Rel is distinct from NF-kB (p50, p65). c-Rel is the cellular homolog of the v-Rel oncogene encoded by the avian REV-T retrovirus. Unlike the NF-kB p50 and p65 that are ubiquitously expressed in all of the cells of the body, c-Rel is exclusively expressed in cells of hematopoietic origin including T cells, B cells, macrophages, and dendritic cells. In addition, c-Rel and NF-kB regulate distinct sets of target genes in different cells. As a result, they have distinct biological functions. c-Rel is a key culprit in many of the inflammatory and autoimmune diseases.

Many receptors and stimuli can activate Rel, including TCR/BCR, TNF receptor superfamily (e.g. CD40, TNFR1, TNFR2, BAFF, APRIL, RANK), the IL-1/TLR receptors, and the Nod-like receptors, as well as activating oncogenes (e.g. Src, Ras, LMP-1, Tax, v-FLIP), reactive oxygen radicals, radiation, and chemotherapeutic agents. In response to these stimuli, Rel regulates the expression of cytokines, chemokines, adhesion molecules, costimulatory molecules, cell cycle molecules, anti-apoptotic proteins, and angiogenic factors. As such, Rel transcription factors are important therapeutic targets for many human disorders, including inflammation, autoimmune diseases, and cancer.

Many human diseases including inflammation, autoimmune disease, and cancer are attributed to aberrant activation of transcription factors, which leads to dysregulated target gene expression and evidence of new biological activities as well as survival or proliferative advantages. In the transcription factor field, NF-kB has attracted central attention as being a transcription factor that is involved in a myriad of biological functions and pathological conditions including the regulation of innate and adaptive immune response to infection, inflammation, cell survival, and tumorigenesis.

Anti-inflammatory and immunosuppressive therapies for inflammation, autoimmune disease, and transplantation have undergone revolutionary development in the past several decades. Early therapies for treating the symptoms of autoimmune/inflammatory disorders relied on glucocorticoids or corticosteroids, hormones from the adrenal medulla discovered in the 1950's. Glucocorticoids are known to be effective in dampening the signs and symptoms of inflammation and the resultant immunopathology in many inflammatory disorders, including rheumatoid arthritis, asthma, allergic dermatitis, inflammatory bowel disease, multiple sclerosis, transplant rejection, graft vs host (GvH) disease, and organ-specific autoimmune diseases, such as thyroiditis and diabetes. Unfortunately, corticosteroids cause severe systemic side effects that impact almost all organ systems, and which preclude their chronic administration.

Palliation of the symptoms of chronic inflammatory disorders such as rheumatoid arthritis is made possible by drugs classified as non-steroid anti-inflammatory drugs (NSAIDs). However, long-term use of many of these agents can cause gastrointestinal (GI) bleeding. In the 1990s, a new class of drugs known as selective inhibitors of Cox2 (Vioxx®, Celebrex®, Bextra®) was developed to treat pain and inflammation but circumventing the NSAID's side effects on the GI tract. Both NSAID and Cox2 inhibitors generally treat only symptoms and relieve pain for autoimmune patients; these drugs are generally unable to curb the progression of the disease. Moreover, the sale of Cox2 inhibitor drugs declined significantly as cardiovascular risks appeared to be common in this class of drugs.

In the 1990's, novel biologics that block tumor necrosis factor (TNF), an inflammatory cytokine, were developed. The three drugs in this class, Enbrel®, Remicade®, and Humira®, have had a major impact in slowing the joint damage caused by rheumatoid arthritis, and one of the drugs is also approved to treat psoriasis, Crohn's disease, and ankylosing spondylitis. While these new biologics drugs have fewer side effects than steroids, they are generally very expensive and may be associated with risk of infections and certain cancers. Moreover, 30-35% of patients tend to become refractory to anti-TNF therapy over time due to the production of neutralizing antibodies.

These facts make apparent the need for alternative safe and efficacious therapies that are also affordable for the treatment of inflammatory, autoimmune, and related diseases and conditions. As suggested by the success of the TNF-blocking class of drugs, a therapy that targets specific cellular proteins involved in the core disease mechanism of autoimmunity is most desirable since such a therapy will slow disease progression. Based on the fundamental function of c-Rel in immune cells, c-Rel blockade further finds use in the treatment of other pathological conditions including inflammation, autoimmune disease, bone loss, transplant rejection, lymphoma, and solid tumors.

Cancer remains an incurable disease. Most current cancer therapies such as chemotherapies have broad cellular targets and exhibit unbearable side effects on the patients. The success of Gleevec® in CML and other related cancers has proved the principle that targeted therapy can be achieved as long as the oncogenic target is identified. c-Rel was first characterized as a proto-oncogene in chicken. Subsequently, c-Rel gene amplification or constitutive activation has been documented in many human B cell leukemia, lymphoma, as well as tumors derived from solid tissues. Therefore, c-Rel is a novel therapeutic target for human cancers with over-reactive c-Rel or NF-kB activity.

(II) c-Rel Knockout Mouse Studies Validate c-Rel as a Drug Target for Inflammatory and Autoimmune Diseases Evidence from knockout animal models and human genetic association studies support c-Rel as a potential therapeutic target for inflammatory and autoimmune diseases. Using c-Rel knockout mice, the Liou laboratory first showed that blocking c-Rel protected mice from developing experimental autoimmune encephalomyelitis (EAE) and Streptozocin-induced diabetes (Hilliard, B A et.al. 2002. J. Clin. Inv. 110, 843; Lamhamedi-Cherradi, S et. al. 2003. J. Immunol. 171,4886). Subsequent studies by us and others further demonstrated the role of c-Rel in collagen-induced arthritis, allergic asthma, *Helicobacter hepaticus*-induced colitis, $CCl_4$-induced liver inflammation, and stress-induced atherosclerosis (Campbell, I et. al. 2000. J. Clin. Inv. 105, 1799; Finn P W et. al. 2001. J. Immunol. 167, 5994; Finn P W et. al. 2002, J. Leuk. Biol., 72, 1054; Yang H. et. al. Transplantation, 2002. 74, 291; Wang, I et. al. 2008. J. Immunol. 180, 8118).

At cellular and molecular levels, c-Rel contributes to multiple steps in autoimmune diseases. These include inducing the expression of inflammatory cytokines of the Th1 and Th17 immune responses (e.g. IL-2, IFN-γ, TNF, IL-12/IL23 members), costimulatory function of antigen presenting cells (e.g. IL-12/IL23 members, OCILRP2), activation of autoreactive lymphocytes (via cell cycle and cell survival proteins), and antibody production. These collective studies thus validated c-Rel as a potential novel therapeutic target for autoimmune diseases.

In addition, intriguing data from recent large-scale genome-wide association studies link several genes in the Rel pathways with increased risks in human autoimmune diseases. These include the association of CD40, c-Rel, Btk, Blk, PKCθ, A20, and TRAF1 genetic variants with rheumatoid arthritis (Criswell, L A et. al. 2010. Immunol. Rev. 233, 55). Previous genetic linkage studies have also identified IL-2/IL2Rα (CD25) and CTLA4 variants as risk markers for Type 1 diabetes, Grave's disease, and inflammatory bowel disease and also link CTLA4 and PTPN22 genetic variants with many autoimmune diseases (Marquez, A et. al. 2009. Am. J Gastroenterol. 104, 1968; Glas J et. al. 2009. Am. J Gastroenterol. 104, 1737). It is important to note that these risk factor genes functionally converge at the Rel transcription factors, including the receptors (CD40, CTLA4), signaling molecules (e.g. Btk, PKCθ, TRAF1), and its downstream targets (e.g. IL-2, CD25, A20), thus corroborating the fundamental role c-Rel in the pathogenesis of autoimmune diseases in general.

Autoimmune diseases arise from the host immune system attacking its own tissues. There are at least 80 autoimmune diseases afflicting various tissues such as joints (rheumatoid arthritis), the central nervous system (multiple sclerosis), intestines (Crohn's disease), or the skin (psoriasis). It is estimated that autoimmune diseases affect 5-8% of the American population, or approximately 23.5 million people.

Since the underlying mechanisms of autoimmune diseases are similar, the Rel inhibitors described in this invention are applicable for the treatment of most of human autoimmune diseases, as listed in Table 2.

Anti-inflammatory and immunosuppressive therapies for inflammation, autoimmune disease, and transplantation have undergone revolutionary development in the past several decades. Since the 1950's, glucocorticoids have been widely used in dampening the signs and symptoms of inflammation and the resultant immunopathology in almost all inflammatory disorders, including rheumatoid arthritis, asthma, allergic dermatitis, inflammatory bowel disease, multiple sclerosis, transplant rejection, graft vs. host (GvH) disease, and organ-specific autoimmune diseases such as thyroiditis and diabetes. It has been shown that the primarily anti-inflammatory activity of glucocorticoids is through the inhibition of Rel activity. Unfortunately, corticosteroids have other cellular targets. Long-term use of corticosteroids can cause severe systemic side effects that impact almost all organ systems, and which preclude their chronic administration. Thus, the euphoria that corticosteroids might be "the cure" for chronic autoimmune and inflammatory diseases rapidly dissipated even before the 1960s. Subsequent development of non-steroid anti-inflammatory drugs (NSAIDs) and Cox2 inhibitors only treat symptoms and relieve pain for autoimmune patients. These drugs, however, are unable to curb the progression of the disease process. Long-term use of NSAIDs can cause gastrointestinal (GI) bleeding, whereas the Cox2 inhibitors were found to associate with increased cardiovascular risks.

Currently, there are several biologics based therapies for autoimmune diseases. The most successful agents are a new class of biologics that block TNF, e.g., Enbrel®, Remicade®, and Humira®. While these new biologic drugs are effective for the treatment of rheumatoid arthritis, psoriasis, and Crohn's diseases, 30-35% patients become refractory to anti-TNF therapies over time due to the production of neutralizing antibodies. Thus, there remains an unmet medical need for anti-TNF resistant patients.

Anti-TNF therapies, however, have not yet shown therapeutic effects on multiple sclerosis (MS). MS patients with relapsing remitting diseases are currently treated with a few disease-modifying drugs, including β-IFNs (Betaseron®, Avonex®, Rebif®), glatiramer acetate (Copaxone®), and Natalizumab (Tysabri®). These drugs are generally ineffective for primary progressive or secondary progressive MS patients. Unfortunately, most patients treated with these drugs eventually relapse and develop disease progression. In addition, Tysabri® has safety concerns as it may increase the risk of progressive multifocal leukoencephalopathy (PML) in small percentage of patients with MS, Crohn's disease, and psoriasis. In 2010, the FDA approved a new oral drug Fingolimod (Gilenya®) for the treatment of relapsing remitting MS patients. Fingolimod targets lysophospholipid S1P1 receptors and prevents lymphocyte migration into CNS. Post-marketing collection of data will help evaluate its safety profile and therapeutic superiority in larger patient pools.

Other therapies currently under clinical trials for autoimmune diseases, which also intercept the Rel pathway, include anti-CD20 (approved for rheumatoid arthritis; clinical trial for multiple sclerosis), anti-IL12/IL23 (approved for psoriasis; clinical trials for Crohn's disease, psoriatic arthritis), anti-IL17 (clinical trials for RA, Crohn's disease, psoriasis, psoriatic arthritis, uveitis), anti-IL-6 (approved for RA, juvenile RA, Crohn's disease, Castleman's disease; clinical trials for other autoimmune disorders, multiple myeloma, prostate cancer), and anti-IL1 (approved for RA, cryopyrin-associated periodic syndrome; clinical trials for RA, juvenile RA, COPD, gout, type 2 diabetes, coronary atherosclerosis).

In conclusion, many autoimmune diseases including multiple sclerosis, ankylosing spondylitis, and type 1 diabetes still have no effective treatments. Existing biologic drugs are very expensive and require administration by injection, thus reducing patient compliance. Therefore, there is a need for identifying new Rel inhibitors and validating their therapeutic potential in autoimmune diseases.

(III) Rel and Tumorigenesis

Many studies, including those from the inventor's lab, have reported the association of hyperactive Rel with human cancers. This may come as no surprise, as several molecules in the Rel pathways were initially identified as potential oncogenes. For example, c-Rel gene amplification and the p52 (p100, lyt10) gene truncation were frequently found in DLBCL. The Rel family has been shown to regulate the expression of cell cycle regulators, anti-apoptotic proteins, inflammatory mediators, cytokines, growth factors, chemokines, and adhesion molecules. As such, Rel could participate in various aspects of tumorigenesis including tumor growth, survival advantage, chemoresistance, angiogenesis, and metastasis. A review of the involvement of Rel in a variety of tumors and the potential mechanism involved in the tumorigenesis follows.

For many virus-induced tumors, it is well-established that some viral oncogenes can directly activate the Rel signaling pathways. For example, in HHV8 (or KSHV)-induced primary effusion lymphoma, it has been shown that the viral oncogene vFLIP associates with TRAFs signaling molecules, leading to constitutive activation of NF-kB (Guasparri I et. al. 2006. EMBO 7, 114). In Burkitt's lymphoma, EBV viral protein LMP-1 also works in a similar mechanism by associating with TRAFs, thus activating signaling pathways normally activated by the TNF receptor members such as CD40 and receptors for Baff and April. The Tax oncoprotein, expressed by HTLV-1 that induces adult T cell leukemia, is shown to activate the Rel pathway by binding to the IKK complex.

Rel activation has been reported in most B cell tumors, including multiple myeloma, diffuse large B cell lymphoma, CLL, primary mediastinal lymphoma, Burkitts' lymphoma, mantle cell lymphoma, MALT lymphoma, and Hodgkin's diseases (See Table 2). For many B cell tumors, the persistent activation of Rel family has been attributed to mutations in the Rel signaling pathways or overexpression of Rel activators. For example, it has been shown that some multiple myeloma (MM) cells have overexpression of the positive regulators of the NF-kB pathway (e.g. CD40, TACI, NIK, NFKB1, NFKB2), whereas others have deletions or mutations in the negative regulators of the Rel signaling components (e.g. TRAF3, CYLD, cIAP1/2) (Annunziata C M, et. al. 2007. Cancer Cell 12,115; Keats, J. et. al. 2007. Cancer Cell 12, 131).

Similar findings were also reported in DLBCL in that mutations in multiple Rel upstream regulators were detected (e.g. A20, CARD11, TRAF2, TRAF3, TAK1, RANK) (Compagno M et. al. 2009. Nature 459(7247):717; Bidère N et. al. 2009. Nature 458, 92).

In CLL however, the survival of tumor cells and its constitutive Rel activity is mostly attributed to persistent activation of the CD40 and the B cell antigen receptor (BCR) signaling pathways, rather than mutations in the signaling pathways (Furman, R R et. al. 2000. J. Immunol. 164, 2200; Bernal, A, et. al. 2001. Blood 98, 3050).

The Rel (NF-kB) has also been shown to be involved in epithelial derived solid tumors. Earlier studies in the late 90's have shown that NF-kB is required for Ras and Bcr-Abl mediated tumorigenesis. Subsequently, several studies point to the involvement of Rel activation in breast tumorigenesis. First, it was shown that EGF receptors such as Her2 can activate NF-kB. A transgenic mouse model demonstrated that overexpression of v-Rel in breast epithelial cells led to the development of breast tumors. IKKε was found to be amplified or overexpressed in breast cancer cell lines and patient-derived tumors. IKKε can activate c-Rel.

Perhaps the most important theme surrounding Rel mediated tumorigenesis is the production of inflammatory mediators. Initial activation of Rel by oncogenes in tumor cells leads to the production of inflammatory mediators (e.g. IL-6, chemokines) that increase tumor survival as well as recruiting bone marrow derived immune cells. The immune cells further produce cytokines and growth factors that amplify and promote tumor cell growth, angiogenesis, and metastasis, as well as conferring drug resistance. This theme has been demonstrated in numerous tumor models (Ammirante, M et. al. 2010. Nature 464, 302; Bromberg, J et. al. 2009 Cancer Cell 15, 79; Boehm, J S et. al. 2007. Cell 129, 1065; Grivennikov, S I and Karin, M 2010. Curr. Opin. Genet. Dev. 20, 65).

For example, in a prostate cancer mouse model, it was shown that B cells and bone marrow derived cells can produce IL-6 and LTβ, which are essential for promoting prostate cancer growth after androgen deprivation. In breast cancer, increased IL-6 expression is associated with metastasis and poor prognosis. It has been shown that Rel and Stat3 synergistically regulate IL-6 expression, thus establishing a positive feedback loop in breast tumorigenesis. In colitis-associated cancer and hepatocellular carcinoma models, both IL-6 and TNF produced by bone marrow derived myeloid cells were shown to promote tumor cell growth and survival. In head and neck squamous cell carcinomas, Rel activates the expression of pro-inflammatory and pro-angiogenic cytokines IL-1α, IL-6, IL-8, and GM-CSF, which promote tumor growth in vivo.

The theme also extends to B cell tumors and other cytokines besides IL-6 and TNF. For examples, in multiple myeloma, IL-17, Baff, and April have been shown to provide autocrine and paracrine growth and survival mediated by the interaction between tumor and stromal cells. IL-23 p19 was shown to be significantly upregulated in majority of carcinoma samples from various organ types, including colon, ovarian, head/neck, lung, breast, stomach, and melanoma. The above studies thus point to potential therapeutic benefits of blocking Rel and its downstream inflammatory mediators for the treatment of a wide variety of solid tumors and blood cancers.

Emerging studies have also demonstrated that radiation therapy and many clinically used chemotherapeutic agents (e.g. doxorubicin, vinca alkaloids, vincristine and vinblastine, camptothecin), can actually induce Rel activity. While some cancer therapies, such as Velcade® and thalidomide, presumably work through inhibiting Rel activity, recent studies have shown that resistance to these drugs is associated with increased Rel activation. Thus, it is conceivable that Rel inhibitors might provide therapeutic benefits to cancer patients either as monotherapy or combination therapy with other cancer drugs.

(IV) Other Diseases Associated with Rel Activation

Rel activation has also been implicated in a wide variety of diseases and pathological conditions, including AIDS, diabetes mellitus, cardiovascular diseases, atherosclerosis, septic shock syndrome, viral replication, osteoporosis, bone loss, organ transplant rejection, graft-versus-host diseases (GVHD), neurodegenerative disorders, ataxia telangiectasia, metabolic disorders, type 1 and type 2 diabetes, as well as aging. Specifically, the c-Rel knockout mice studies have clearly demonstrated the involvement of c-Rel activation in stress-induced atherosclerosis (A. Bierhaus et. al. 2010. JCI) and transplant rejection (Finn P W et. al. 2001, J I; Finn, P W et. al. 2002, J Leukoc. Biol; Yang H. et. al. Transplantation, 2002).

BRIEF SUMMARY OF THE DISCLOSURE

The present invention relates to compositions and methods for targeting c-Rel. In particular, the present invention provides compositions with c-Rel inhibitory (i.e., regulatory) activities, and their use in the treatment of cancer, autoimmune disease, inflammatory disease, diabetes, transplant rejection, graft versus host (GvH) diseases, allergy, asthma, and bone loss. The compositions may also be used for regulating or inhibiting c-Rel for research and drug screening applications. In some embodiments, the invention provides a method of decreasing c-Rel activity, comprising contacting a cell expressing a c-Rel gene with a c-Rel activity inhibitor.

In one set of embodiments, the compound having c-Rel inhibitory activity has the formula:

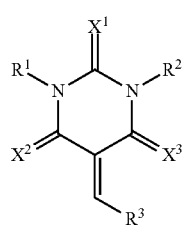

(1)

In Formula (1), $R^1$ and $R^2$ are each independently selected from hydrogen atom and hydrocarbon groups having at least one and up to thirty carbon atoms and optionally substituted with one or more heteroatoms selected from halogen, nitrogen, oxygen, and sulfur; $R^3$ is selected from hydrocarbon groups having at least one and up to thirty carbon atoms and optionally substituted with one or more heteroatoms selected from halogen, nitrogen, oxygen, and sulfur; and $X^1$, $X^2$, and $X^3$ are each independently selected from oxygen and sulfur atoms, provided that at least one of $X^1$, $X^2$, and $X^3$ is a sulfur atom.

In another set of embodiments, the compound having c-Rel inhibitory activity has the formula:

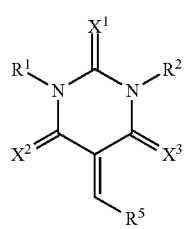

(2)

In Formula (2), $R^1$ and $R^2$ are each independently selected from hydrogen atom and hydrocarbon groups having at least one and up to thirty carbon atoms and optionally substituted with one or more heteroatoms selected from halogen, nitrogen, oxygen, and sulfur; $R^5$ is a fused ring system; and $X^1$, $X^2$, and $X^3$ are each independently selected from oxygen and sulfur atoms.

The invention is also directed to pharmaceutical compositions containing any of the c-Rel inhibiting compounds described above and a pharmaceutically acceptable carrier. The pharmaceutical composition may also include any number of other auxiliary agents used in the art, e.g., buffering agents, stabilizing agents, emulsifying agents, pH adjusting agents, surfactants, and flavorants.

In another aspect, the invention is directed to a method of treating a patient afflicted with a disease or condition associated with c-Rel hyperactivity (overexpression) by administering to the patient an effective amount of any of the c-Rel activity inhibitors described above. The disease or condition being treated can be, for example, cancer, autoimmune disease, inflammation or inflammatory disease, diabetes, transplant rejection, graft versus host (GvH) diseases, allergy, asthma, or bone loss.

Generally, the c-Rel regulatory or inhibitor compound functions as a "direct" Rel inhibitor. A "direct" Rel inhibitor is a compound that binds Rel directly and inhibits its DNA binding and transcriptional function Inhibitors blocking an upstream signaling molecule, such as IKKβ that are currently under development in the pharmaceutical industry only block the "classical" Rel pathway activated by IKKβ. Therefore, IKKβ inhibitor-based therapy will have limited efficacy toward tumor cells that utilize other NF-kB activating pathways, including IKKα, NIK, AKT, and MEKK. In fact, this is how "drug resistant" tumors frequently develop in patients using monotherapy. This is because, even though the drug may have killed most tumor cells that feed on the pathway blocked by the drug, it has little or no effect on residual tumor cells that are dependent on different survival pathways. As a result of drug selection, resistant tumor cells propagate.

By contrast, a particular advantage of "direct" Rel inhibitors is that they can block Rel activation mediated by a wide range of receptor signaling pathways. Thus, a therapy based on a "direct" inhibitor will significantly lower the probability of developing drug resistance or relapse that usually arises from tumor cells utilizing other pathways not blocked by the drug.

Novel strategies are described herein to identify Rel inhibitors that bind Rel protein directly. Based on the Rel structure, this strategy can identify compounds that bind to different allosteric sites, resulting in changes in protein conformation and subsequently affecting target gene expression. The Rel inhibitors can be further developed as specific probes or drug candidates for any of the conditions or diseases described above, such as inflammation, autoimmune diseases, transplantation rejection, and cancers in humans. Therapies based on these direct Rel inhibitors also minimize toxicity and reduce the development of drug resistance and relapse.

FIGS. 2A, 2B. Some structure-activity-relationships (SARs) strategy for the c-Rel inhibiting compounds (FIG. 2A), and exemplary synthetic method (FIG. 2B).

Figure 3:
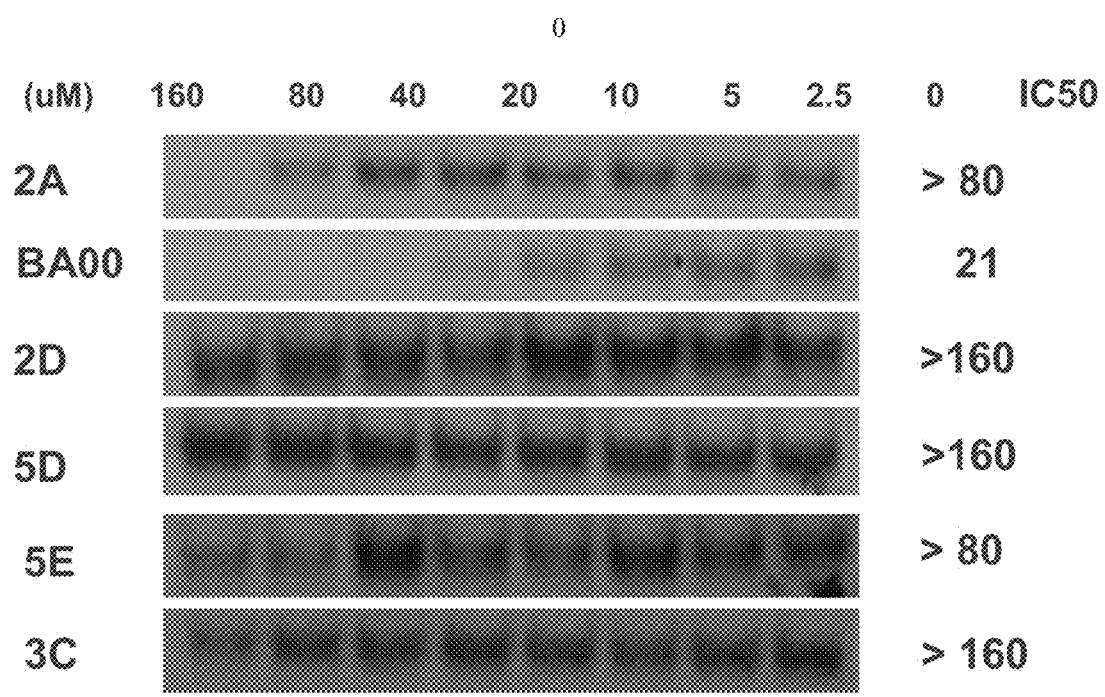

FIG. 3. Electrophoretic mobility shift assay (EMSA) of Rel inhibitor analogs (BA009 and other compounds) to determine $IC_{50}$ results.

Figure 4:
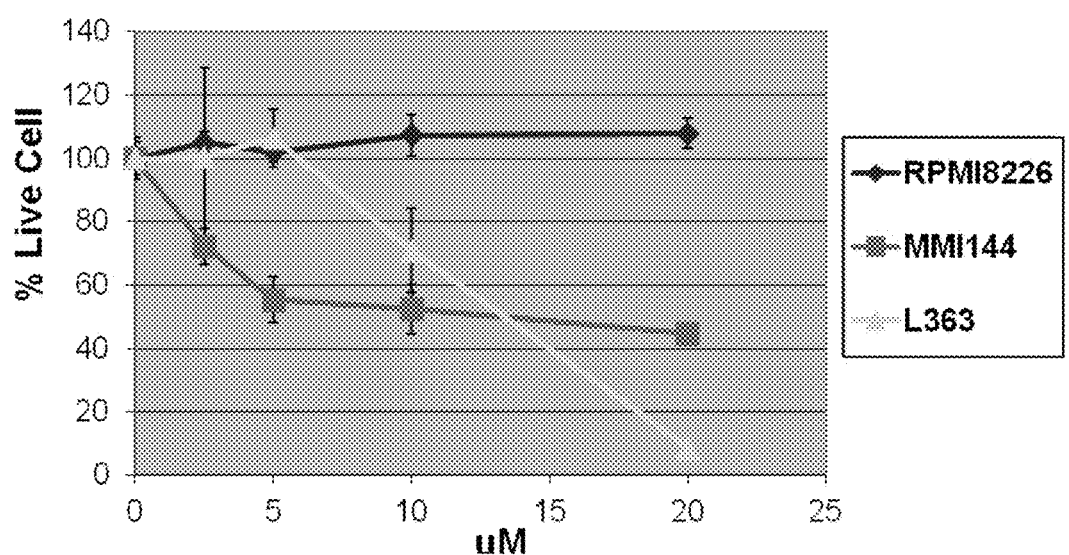

FIG. 4. Chart demonstrating the inhibitory effect of a representative compound (BA001) on the growth of three multiple myeloma cell lines (RPMI8226, MM144, and L363).

Figure 5:
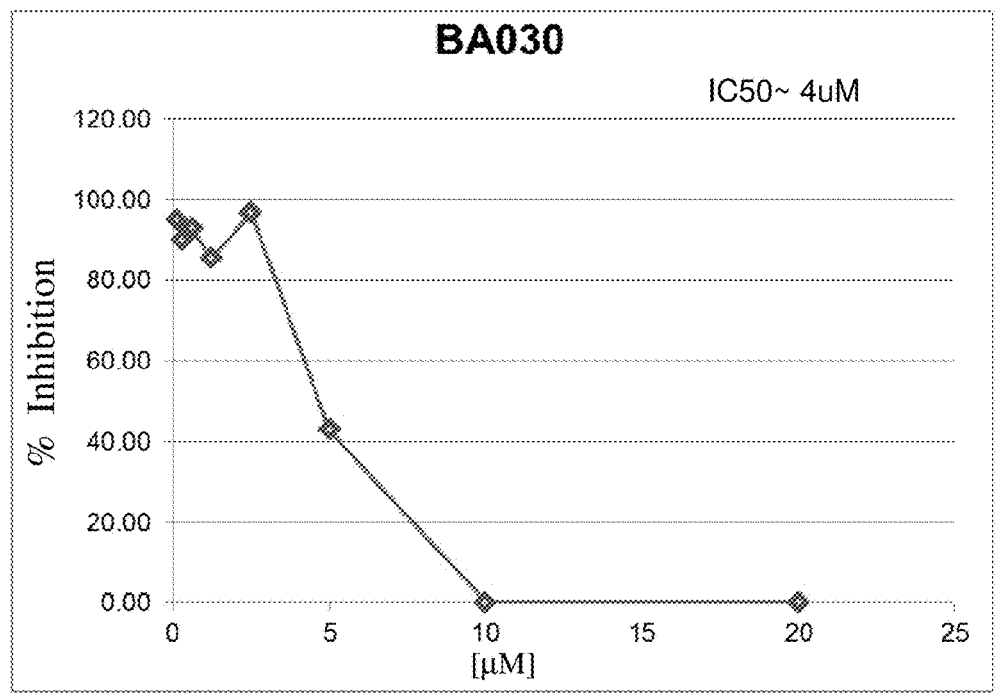

FIG. 5. Chart demonstrating anti-tumor activity of a representative Rel inhibitor (BA030) on cytotoxicity of DLBCL tumor cell lines.

Figure 6:
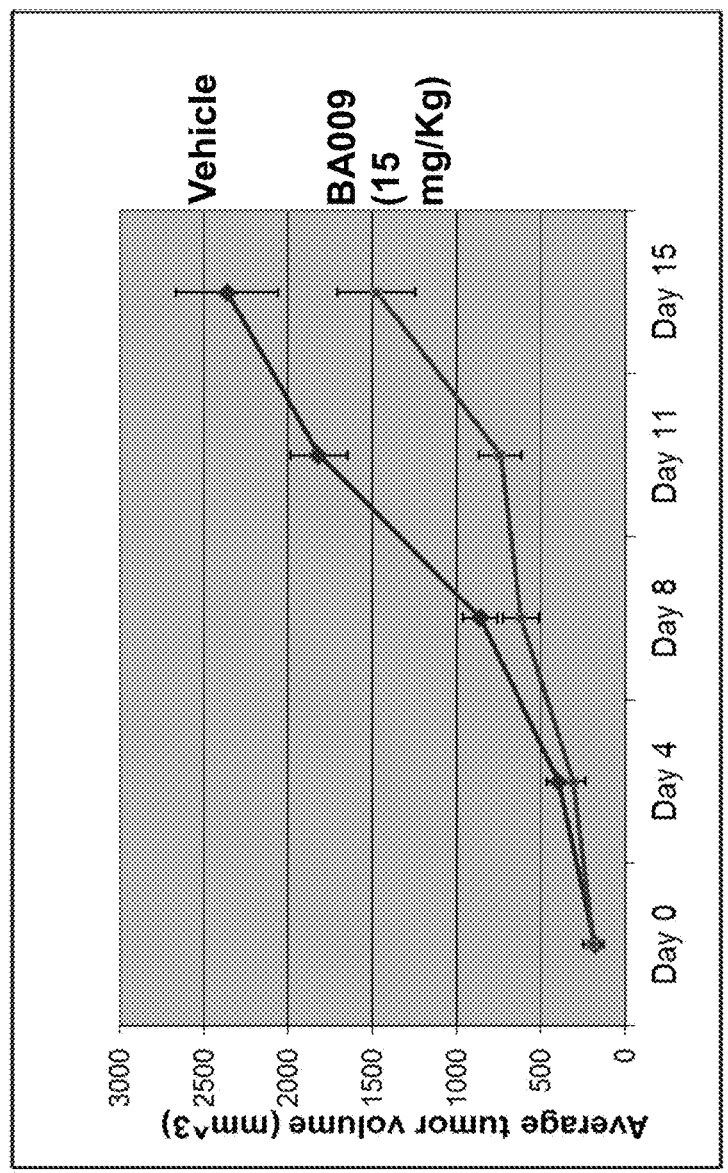

FIG. 6. Chart showing anti-tumor activity of a representative Rel inhibitor (BA009) in xenograft tumor models.

Figure 7:
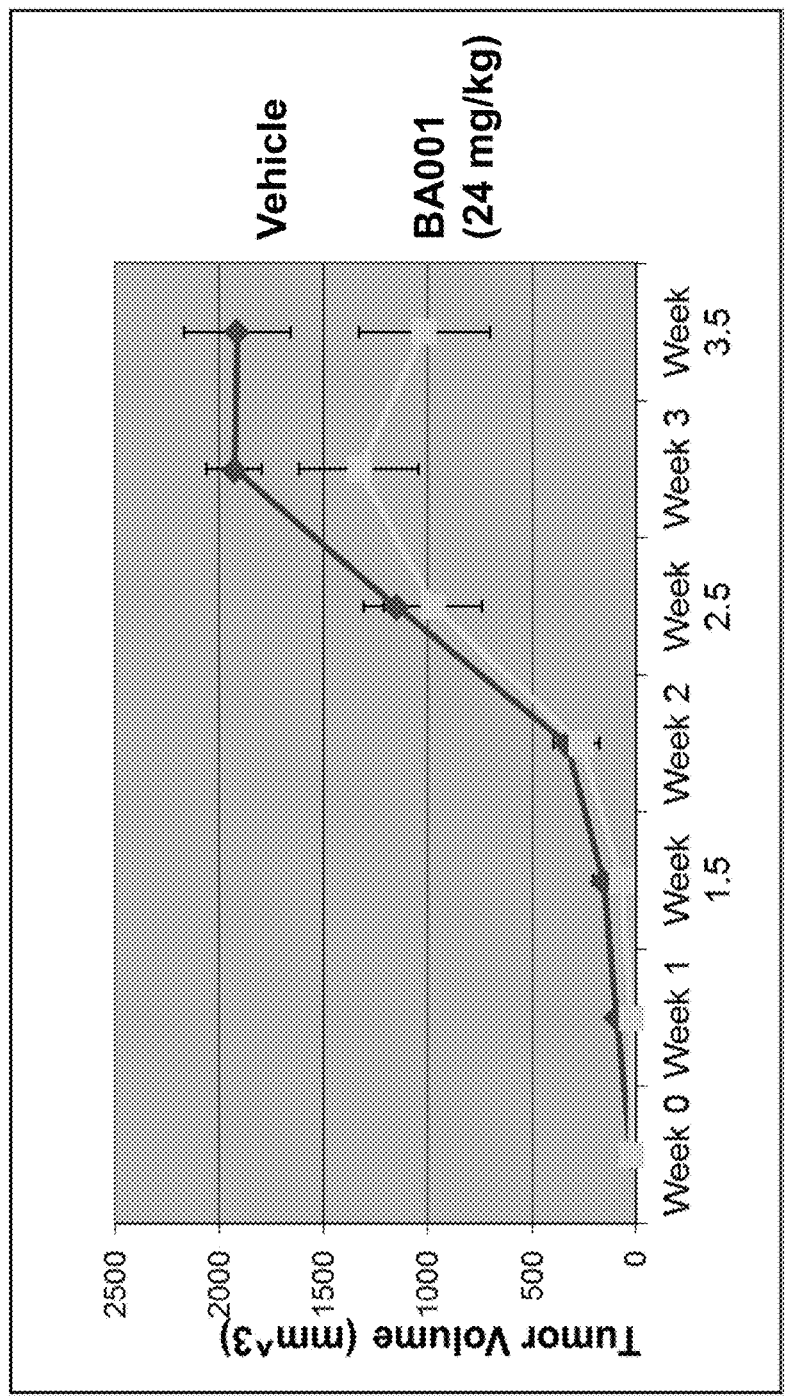

FIG. 7. Chart showing anti-tumor activity of a representative Rel inhibitor (BA001) in xenograft tumor models.

Figure 8:
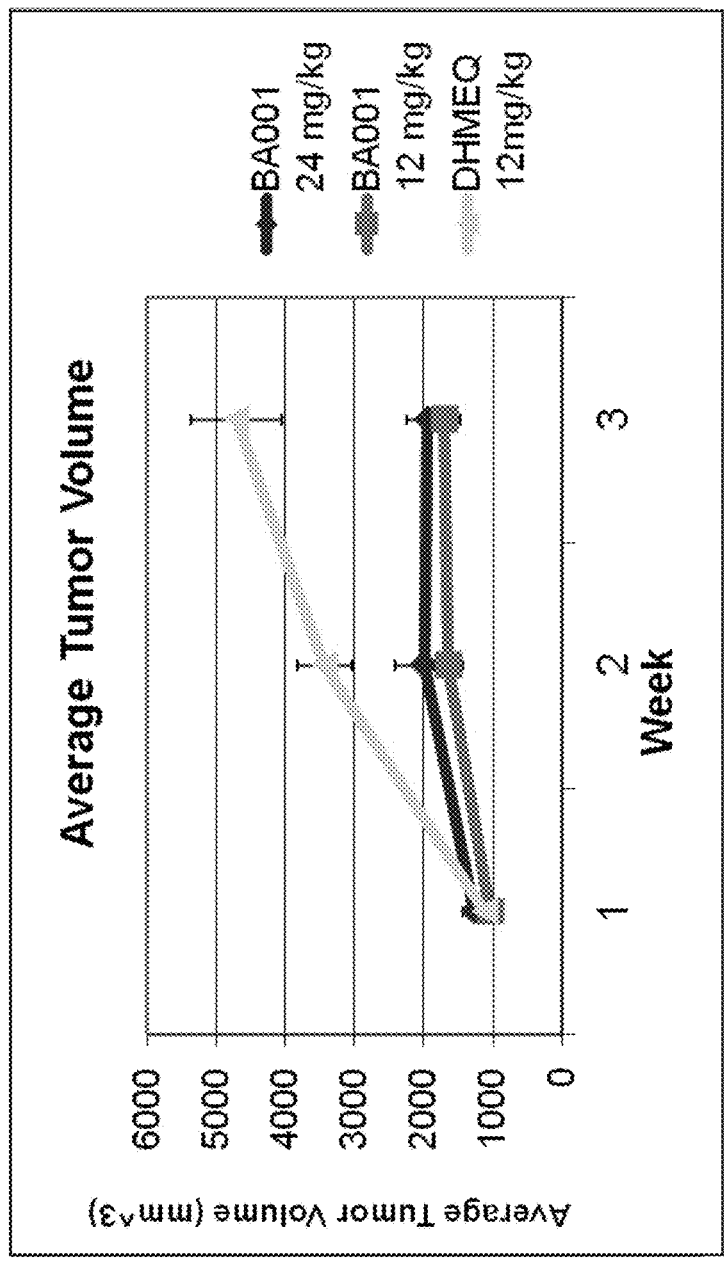

FIG. 8. Chart comparing anti-tumor activity of a representative Rel inhibitor (BA001) with DHMEQ in xenograft tumor models.

Figures 9A, 9B:
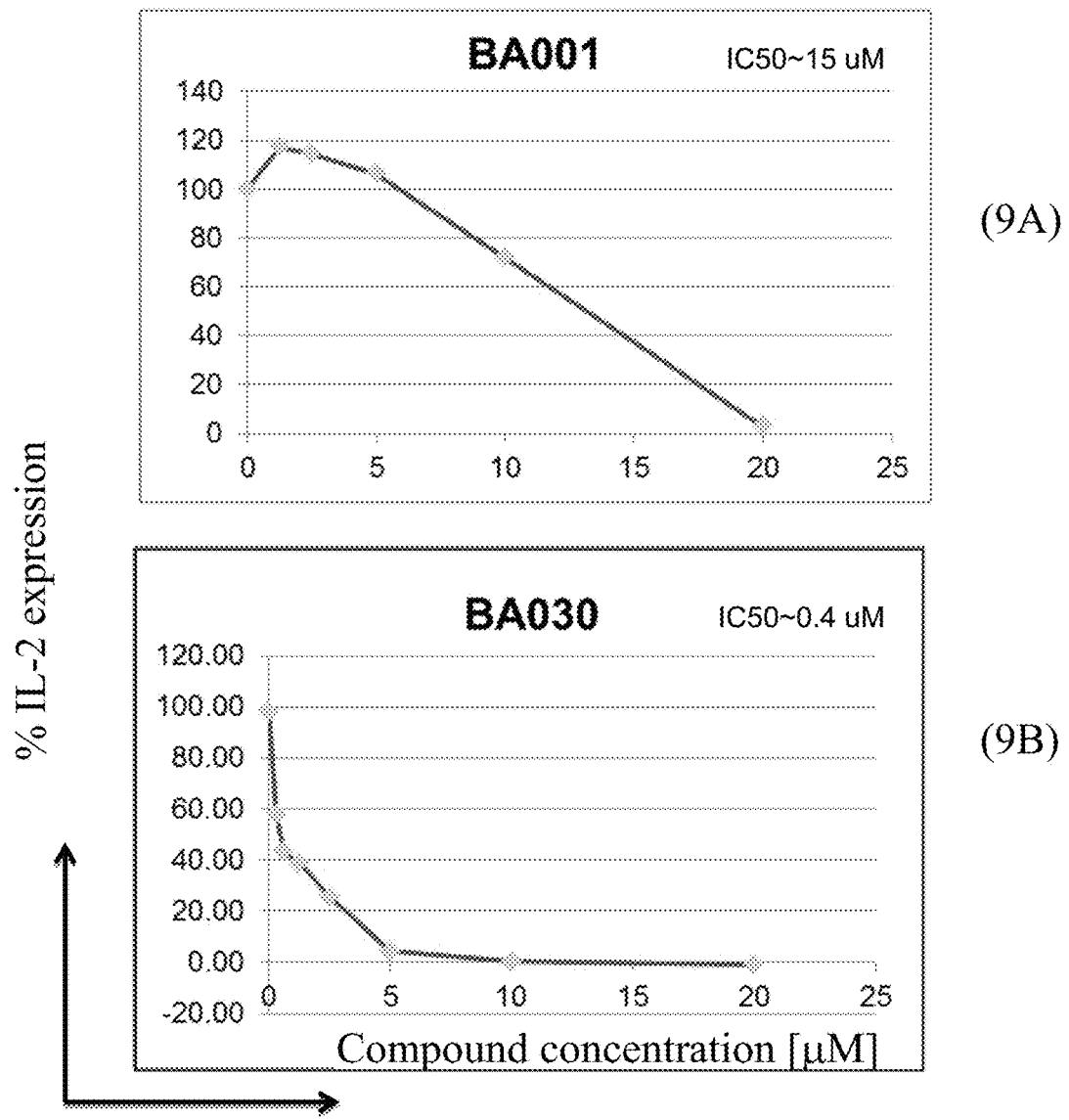

FIGS. 9A, 9B. Charts shows the utilization of IL-2 inhibition to determine $IC_{50}$ of Rel inhibitor compound BA001 (FIG. 9A) and Rel inhibitor compound BA030 (FIG. 9B).

DETAILED DESCRIPTION OF THE DISCLOSURE

For convenience, before further description of the present invention, certain terms employed in the specification, examples, and appended claims are described here. These definitions should be read in light of the entire disclosure and as would be understood by a person skilled in the art.

The terms "a" and "an" are used herein to refer to one or to more than one (i.e., to at least one) of the grammatical object of the article. By way of example, "an element" can mean one or more elements, unless otherwise specified.

The term "about" generally indicates within ±0.5%, 1%, 2%, 5%, or up to ±10% of the indicated value. For example, an amount of "about 10 wt %" generally indicates, in its broadest sense, 10 wt %±10%, which indicates 9.0-11.0 wt %. The term "about" may alternatively indicate a variation or average in a physical characteristic of a group.

The term "hydrocarbon group" or "hydrocarbon linker" (also identified as "R"), as used herein, designates, in a first embodiment, groups or linkers composed solely of carbon and hydrogen. In different embodiments, one or more of the hydrocarbon groups or linkers can contain precisely, or a minimum of, or a maximum of, for example, 1, 2, 3, 4, 5, 6, 7, 8, 9, 10, 11, 12, 13, 14, 15, 16, 17, 18, 20, 25, or 30 carbon atoms, or a number of carbon atoms within a particular range bounded by any two of the foregoing carbon numbers. Hydrocarbon groups or linkers in different compounds described herein, or in different positions of a compound, may possess the same or different number (or a preferred range thereof) of carbon atoms in order to independently adjust or optimize the activity or other characteristics of the compound.

The hydrocarbon groups or linkers (R) can be, for example, saturated and straight-chained (i.e., straight-chained alkyl groups or alkylene linkers). Some examples of straight-chained alkyl groups (or alkylene linkers) include methyl (or methylene linker, i.e., —$CH_2$—, or methine linker), ethyl (or ethylene or dimethylene linker, i.e., —$CH_2CH_2$-linker), n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, and n-eicosyl groups (or their respective linker analogs).

The hydrocarbon groups or linkers (R) can alternatively be saturated and branched (i.e., branched alkyl groups or alkylene linkers). Some examples of branched alkyl groups include isopropyl (2-propyl), isobutyl (2-methylprop-1-yl), sec-butyl(2-butyl), t-butyl, 2-pentyl, 3-pentyl, 2-methylbut-1-yl, isopentyl (3-methylbut-1-yl), 1,2-dimethylprop-1-yl, 1,1-dimethylprop-1-yl, neopentyl (2,2-dimethylprop-1-yl), 2-hexyl, 3-hexyl, 2-methylpent-1-yl, 3-methylpent-1-yl, isohexyl (4-methylpent-1-yl), 1,1-dimethylbut-1-yl, 1,2-dimethylbut-1-yl, 2,2-dimethylbut-1-yl, 2,3-dimethylbut-1-yl, 3,3-dimethylbut-1-yl, 1,1,2-trimethylprop-1-yl, and 1,2,2-trimethylprop-1-yl groups, isoheptyl, isooctyl, and the numerous other branched alkyl groups having up to 30 carbon atoms, wherein the "1-yl" suffix represents the point of attachment of the group. Some examples of branched alkylene linkers are those derived by removal of a hydrogen atom from one of the foregoing exemplary branched alkyl groups (e.g., isopropylene, —$CH(CH_3)CH_2$—).

The hydrocarbon groups or linkers (R) can alternatively be saturated and cyclic (i.e., cycloalkyl groups or cycloalkylene linkers). Some examples of cycloalkyl groups include cyclopropyl, cyclobutyl, cyclopentyl, cyclohexyl, cycloheptyl, and cyclooctyl groups. The cycloalkyl group can also be a polycyclic (e.g., bicyclic) group by either possessing a bond between two ring groups (e.g., dicyclohexyl) or a shared (i.e., fused) side (e.g., decalin and norbornane). Some examples of cycloalkylene linkers are those derived by removal of a hydrogen atom from one of the foregoing exemplary cycloalkyl groups.

The hydrocarbon groups or linkers (R) can alternatively be unsaturated and straight-chained (i.e., straight-chained olefinic or alkenyl groups or linkers). The unsaturation occurs by the presence of one or more carbon-carbon double bonds and/or one or more carbon-carbon triple bonds. Some examples of straight-chained olefinic groups include vinyl, propen-1-yl 3-buten-1-yl (—$CH_2$=CH—$CH_2$—$CH_2$—), 2-buten-1-yl (—$CH_2$—CH=CH—$CH_2$—), butadienyl, 4-penten-1-yl, 3-penten-1-yl, 2-penten-1-yl, 2,4-pentadien-1-yl, 5-hexen-1-yl, 4-hexen-1-yl, 3-hexen-1-yl, 3,5-hexadien-1-yl, 1,3,5-hexatrien-1-yl, 6-hepten-1-yl, ethynyl, propargyl (2-propynyl), and the numerous $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, and higher unsaturated and straight-chained hydrocarbon groups. Some examples of straight-chained olefinic linkers are those derived by removal of a hydrogen atom from one of the foregoing exemplary straight-chained olefinic groups (e.g., vinylene, —CH=CH—, or vinylidene).

The hydrocarbon groups or linkers (R) can alternatively be unsaturated and branched (i.e., branched olefinic or alkenyl groups or linkers). Some examples of branched olefinic groups include propen-2-yl (—$CH_2$=C.—$CH_3$), 1-buten-2-yl (—$CH_2$=C.—$CH_2$—$CH_3$), 1-buten-3-yl (—$CH_2$=CH—CH.—$CH_3$), 1-propen-2-methyl-3-yl (—$CH_2$=C($CH_3$)—$CH_2$.), 1-penten-4-yl, 1-penten-3-yl, 1-penten-2-yl, 2-penten-2-yl, 2-penten-3-yl, 2-penten-4-yl, and 1,4-pentadien-3-yl. Some examples of branched olefinic linkers are those derived by removal of a hydrogen atom from one of the foregoing exemplary branched olefinic groups.

The hydrocarbon groups or linkers (R) can alternatively be unsaturated and cyclic (i.e., cycloalkenyl groups or cycloalkenylene linkers). The unsaturated and cyclic group can be aromatic or aliphatic. Some examples of unsaturated and cyclic hydrocarbon groups include cyclopropenyl, cyclobutenyl, cyclopentenyl, cyclopentadienyl, cyclohexenyl, cyclohexadienyl, phenyl, benzyl, cycloheptenyl, cycloheptadienyl, cyclooctenyl, cyclooctadienyl, and cyclooctatetraenyl groups. The unsaturated cyclic hydrocarbon group can also be a polycyclic group (such as a bicyclic or tricyclic polyaromatic group) by either possessing a bond between two of the ring groups (e.g., biphenyl) or a shared (i.e., fused) side, as in naphthalene, anthracene, phenanthrene, phenalene, or indene fused ring systems. Some examples of cycloalkenylene linkers are those derived by removal of a hydrogen atom from one of the foregoing exemplary cycloalkenyl groups (e.g., phenylene and biphenylene).

One or more of the hydrocarbon groups or linkers (R) may (i.e., optionally) be substituted with (i.e., include) one or more heteroatoms, which are non-carbon non-hydrogen atoms. Some examples of heteroatoms include oxygen (O), nitrogen (N), sulfur (S), and halogen (halide) atoms. Some examples of halogen atoms include fluorine, chlorine, bromine, and iodine. In some embodiments, the heteroatom atom inserts between at least two carbon atoms (as in —C—O—C— ether, —C—S—C— thioether, —C—N(R)—C— tertiary amine, or —C(=NR)C— imine) or between at least one carbon atom and at least one hydrogen atom (as in —C—OH, —C—SH, —C—NH$_2$, —C—NH—C—, or —C(=NH)C—), wherein the shown carbon atom in each case can be considered part of a hydrocarbon group R described above. In other embodiments, the heteroatom replaces one or more hydrogen atoms and/or one or more carbon atoms in the hydrocarbon group, as in halogen-substituted groups (e.g., a —CH$_2$F, —CHF$_2$, and —CF$_3$) and carbonyl-substituted groups, such as ketone and aldehyde groups. In some embodiments, the hydrocarbon is substituted with multiple oxygen atoms to result in a dialkyleneoxide or polyalkyleneoxide group, such as a diethyleneoxide or polyethyleneoxide group. In the case of nitrogen or sulfur substitution, the nitrogen or sulfur atom may be bonded to a sufficient number of groups to make it positively charged, as in an ammonium group (e.g., —NR'$_3^+$) or sulfonium group (e.g., —SR'$_2^+$), in which case the positively charged moiety is necessarily associated with a counteranion (wherein R' independently represents hydrogen atom or any of the hydrocarbon groups described above). Likewise, a heteroatom may bear a negative charge, as in a deprotonated alkoxide or thio group, in which case the negatively charged moiety is necessarily associated with a countercation.

When two or more same or different heteroatoms are bound to each other or located on the same carbon atom, the resulting group containing the heteroatoms is herein referred to as a "heteroatom-containing group". Thus, substitution with one or more heteroatoms also includes heteroatom-containing groups, unless otherwise specified. Some examples of heteroatom-containing groups and linkers include carboxy (—C(O)OR' or —OC(O)R'), thiocarboxy (—C(S)OR' or —OC(S)R'), carboxamide (—C(O)NR'$_2$, —C(O)NR'—, or —N(R')C(O)—), urea (—NR'—C(O)—NR'$_2$ or —NR'—C(O)—NR'—), thiourea (—NR'—C(S)—NR'$_2$ or —NR'—C(S)—NR'—), carbamate (—NR'—C(O)—OR', —OC(O)—NR'$_2$, or —NR'—C(O)—O—), thiocarbamate (—NR'—C(S)—OR', —OC(S)—NR'$_2$, or —NR'—C(S)—O—), nitro (NO$_2$), nitrile (CN), sulfonyl (—S(O)$_2$R' or —S(O)$_2$—), sulfinyl (i.e., sulfoxide, —S(O)R' or —S(O)—), disulfide (—C—S—S—C—), sulfonate (—S(O)$_2$R'), and amine oxide (as typically found in a nitrogen-containing ring), wherein R' independently represents hydrogen atom or any of the hydrocarbon groups (R) described above or R" described below. For example, —C(O)OR' includes carboxylic acid (—C(O)OH) and carboxylic ester (—C(O)OR), where R is any of the hydrocarbon groups described above. The heteroatom-containing group may also either insert between carbon atoms or between a carbon atom and hydrogen atom, if applicable, or replace one or more hydrogen and/or carbon atoms.

In some embodiments, the hydrocarbon group or linker (R) is substituted with one or more halogen atoms to result in a partially halogenated or perhalogenated hydrocarbon group. Some examples of partially halogenated hydrocarbon groups include —CHY$_2$, —CH$_2$Y, —CH$_2$CY$_3$, —CH(CY$_3$)$_2$, or a halo-, dihalo-, trihalo-, or tetrahalo-substituted phenyl group, wherein Y represents any of F, Cl, Br, or I, and more commonly F or Cl. Some examples of perhalogenated hydrocarbon groups include —CY$_3$, —CY$_2$CY$_3$, —CY$_2$CY$_2$CY$_3$, —CY(CY$_3$)$_2$, or perhalophenyl, —C$_6$Y$_5$).

In particular embodiments, the hydrocarbon group (R) is, or includes, a cyclic or polycyclic (i.e., bicyclic, tricyclic, or higher cyclic) saturated or unsaturated (e.g., aliphatic or aromatic) hydrocarbon group that includes at least one ring heteroatom, such as one, two, three, four, or higher number of ring heteroatoms. Such heteroatom-substituted cyclic hydrocarbon groups are referred to herein as "heterocyclic groups". As used herein, a "ring heteroatom" is an atom other than carbon and hydrogen (typically, selected from nitrogen, oxygen, and sulfur) that is inserted into or replaces a ring carbon atom in a hydrocarbon ring structure. In some embodiments, the heterocyclic group is saturated. In other embodiments, the heterocyclic group is unsaturated, i.e., aliphatic or aromatic heterocyclic groups, wherein the aromatic heterocyclic group is also referred to herein as a "heteroaromatic ring", or a "heteroaromatic fused-ring system" in the case of at least two fused rings, at least one of which contains at least one ring heteroatom. The heterocyclic group may be bound via only one or more of its ring carbon atoms to the remainder of the c-Rel inhibiting compound, or bound by only one or more of its ring heteroatoms to the c-Rel inhibiting compound, or bound by both a ring carbon atom and a ring heteroatom.

Some examples of saturated heterocyclic groups containing at least one oxygen atom include oxetane, tetrahydrofuran, tetrahydropyran, 1,4-dioxane, 1,3-dioxane, and 1,3-dioxepane rings. Some examples of saturated heterocyclic groups containing at least one nitrogen atom include pyrrolidine, piperidine, piperazine, imidazolidine, azepane, and decahydroquinoline rings. Some examples of saturated heterocyclic groups containing at least one sulfur atom include tetrahydrothiophene, tetrahydrothiopyran, 1,4-dithiane, 1,3-dithiane, and 1,3-dithiolane rings. Some examples of saturated heterocyclic groups containing at least one oxygen atom and at least one nitrogen atom include morpholine and oxazolidine rings. An example of a saturated heterocyclic group containing at least one oxygen atom and at least one sulfur atom includes 1,4-thioxane. An example of a saturated heterocyclic group containing at least one nitrogen atom and at least one sulfur atom includes thiazolidine and thiamorpholine rings.

Some examples of unsaturated heterocyclic groups containing at least one oxygen atom include furan, pyran, 1,4-dioxin, benzofuran, dibenzofuran, and dibenzodioxin rings. Some examples of unsaturated heterocyclic groups containing at least one nitrogen atom include pyrrole, imidazole, pyrazole, pyridine, pyrazine, pyrimidine, 1,3,5-triazine, azepine, diazepine, indole, purine, benzimidazole, indazole, 2,2'-bipyridine, quinoline, isoquinoline, phenanthroline, 1,4,5,6-tetrahydropyrimidine, 1,2,3,6-tetrahydropyridine, 1,2,3,4-tetrahydroquinoline, quinoxaline, quinazoline, pyridazine, cinnoline, 5,6,7,8-tetrahydroquinoxaline, 1,8-naphthyridine, and 4-azabenzimidazole rings. Some examples of unsaturated heterocyclic groups containing at least one sulfur atom include thiophene, thianaphthene, and benzothiophene rings. Some examples of unsaturated heterocyclic groups containing at least one oxygen atom and at least one nitrogen atom include oxazole, isoxazole, benzoxazole, benzisoxazole, oxazoline, 1,2,5-oxadiazole (furazan), and 1,3,4-oxadiazole rings. Some examples of unsaturated heterocyclic groups containing at least one nitrogen atom and at least one sulfur atom include thiazole, isothiazole, benzothiazole, benzoisothiazole, thiazoline, and 1,3,4-thiadiazole rings.

In some embodiments, any of the generic substituents (e.g., R, $R_1$, $R_2$, $R_3$, $R_4$, and $R_5$, and the like) described below may independently exclude any one or more of the classes, subclasses, or particular hydrocarbon groups described above, or may independently include only specific hydrocarbon groups selected from the hydrocarbon groups (R) described above. Similarly, any of the generic substituents described below may independently exclude any one or more heteroatoms or heteroatom-containing groups.

In a first embodiment, the c-Rel inhibitory compound has the following chemical structure:

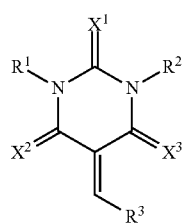

(1)

In Formula (1), the groups $R^1$ and $R^2$ are each independently selected from hydrogen atom and any of the hydrocarbon groups R, as described above, having at least one and up to thirty carbon atoms and optionally substituted with one or more heteroatoms selected from halogen, nitrogen, oxygen, and sulfur. In a first embodiment of Formula (1), $R^1$ and $R^2$ are hydrogen atoms. In a second embodiment, one of $R^1$ and $R^2$ is a hydrogen atom and one of $R^1$ and $R^2$ is a hydrocarbon group R, such as any of the alkyl, alkenyl, alkynyl, cycloalkyl, unsaturated rings (aliphatic or aromatic), polycyclic rings (i.e., connected or fused ring systems), heterocycles, and polycyclic heterocycles described above. In a third embodiment, both of $R^1$ and $R^2$ are independently selected from hydrocarbons group R, such as any of the alkyl, alkenyl, alkynyl, cycloalkyl, unsaturated rings (aliphatic or aromatic), polycyclic rings (i.e., connected or fused ring systems), heterocycles, and polycyclic heterocycles described above. In some embodiments, one or both of $R^1$ and $R^2$ are independently selected from hydrocarbon groups having at least one and up to two, three, four, five, six, seven, eight, nine, ten, eleven, or twelve carbon atoms, and more specifically, straight-chained or branched alkyl groups having any of the foregoing number of carbon atoms. In some embodiments, $R^1$ and $R^2$ are independently selected from hydrogen atom, methyl, ethyl, n-propyl, isopropyl, n-butyl, sec-butyl, t-butyl, n-pentyl, isopentyl, n-hexyl, isohexyl, cyclopropyl, cyclobutyl, cyclopentyl, cyclohexyl, cycloheptyl, vinyl, and allyl, and/or any of the unsubstituted or heteroatom-substituted monocyclic or polycyclic ring systems described above.

The group $R^3$ in Formula (1) is selected from any of the hydrocarbon groups R, as described above, having at least one and up to thirty carbon atoms and optionally substituted with one or more heteroatoms selected from halogen, nitrogen, oxygen, and sulfur. In particular embodiments, $R^3$ is or includes a hydrocarbon ring. The hydrocarbon ring can be, for example, any of the saturated or unsaturated (including aliphatic or aromatic) hydrocarbon rings described above, wherein the hydrocarbon ring may also be carbocyclic or heterocyclic and may also be monocyclic or polycyclic (i.e., two or more rings connected by a bond or fused together as a fused ring system).

In one embodiment, $R^3$ is or includes a monocyclic ring, such as any of the monocyclic rings described above. The monocyclic ring can be carbocyclic, such as cyclopropyl, cyclobutyl, cyclopentyl, cyclohexyl, cycloheptyl, cyclopentenyl, cyclopentadienyl, cyclohexenyl, cyclohexadienyl, phenyl, benzyl, and hydrocarbon-substituted versions thereof. Alternatively, the monocyclic ring can be heterocyclic, such as pyrrolidinyl, piperidinyl, piperazinyl, pyrrolyl, imidazolyl, pyrazolyl, pyridinyl, pyrazinyl, oxazolyl, thiazolyl, 1,3,5-triazinyl, pyrimidinyl, morpholinyl, triazolyl, furanyl, thienyl, tetrahydrofuranyl, pyranyl, and hydrocarbon-substituted versions thereof, particularly those hydrocarbon groups having at least one and up to two, three, four, five, six, seven, eight, nine, or ten carbon atoms optionally substituted with one or more heteroatoms selected from halogen, oxygen, nitrogen, and sulfur.

In other embodiments $R^3$ is or includes a fused ring system, including any of the fused ring systems described above. The fused ring system can be carbocyclic, such as naphthyl, anthracyl, indenyl, phenanthryl, tetracenyl, phenalenyl, chrysenyl, or azulenyl. Alternatively, the fused ring system can be a heteroatom-substituted fused ring system, particularly those containing one or two heteroatoms selected from nitrogen and oxygen atoms, such as indolyl, quinolinyl, isoquinolinyl, bipyridinyl, quinazolinyl, quinoxalinyl, 1,8-naphthyridinyl, purinyl, or benzofuranyl, wherein any of the foregoing fused ring systems may or may not be substituted with one or more hydrocarbon groups R described above, particularly those hydrocarbon groups having at least one and up to two, three, four, five, six, seven, eight, nine, or ten carbon atoms optionally substituted with one or more heteroatoms selected from halogen, oxygen, nitrogen, and sulfur.

In particular embodiments, the monocyclic or fused ring system, whether carbocyclic or heterocyclic, is substituted with one or more (e.g., one, two, three, or four) groups of the formula —OR" and/or —N(R")$_2$, wherein R" is independently selected from hydrogen atom and hydrocarbon groups (R) described above, particularly those hydrocarbon groups having at least one and up to two, three, four, five, six, seven, eight, nine, or ten carbon atoms optionally substituted with one or more heteroatoms selected from halogen, oxygen, nitrogen, and sulfur.

In particular embodiments, $R^3$ is a fused ring system selected from any of the following structures:

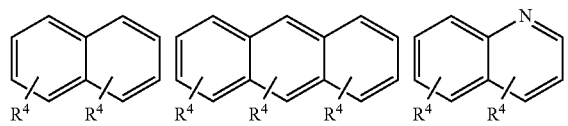

-continued

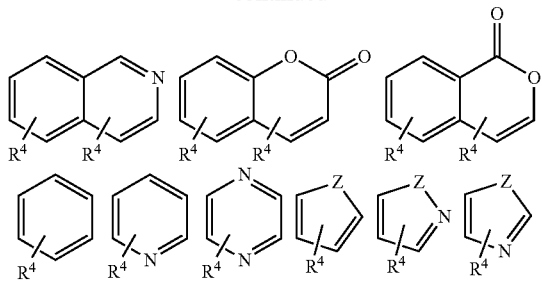

In the above structures for $R^3$, Z is selected from —$CR'_2$—, —$NR'$—, O, or S, wherein R' is independently selected from hydrogen atom and hydrocarbon groups (R) described above, particularly those hydrocarbon groups having at least one and up to two, three, four, five, six, seven, eight, nine, or ten carbon atoms optionally substituted with one or more heteroatoms selected from halogen, oxygen, nitrogen, and sulfur. The group $R^4$ is located on a ring carbon atom and is independently selected from hydrogen atom, halogen atom, and hydrocarbon groups (R) described above, particularly those hydrocarbon groups having at least one and up to two, three, four, five, six, seven, eight, nine, or ten carbon atoms optionally substituted with one or more heteroatoms selected from halogen, oxygen, nitrogen, and sulfur. In particular embodiments, $R^4$ has the formula —$OR''$ or —$N(R'')_2$, wherein R'' is independently selected from hydrogen atom and hydrocarbon groups (R) described above, particularly those hydrocarbon groups having at least one and up to two, three, four, five, six, seven, eight, nine, or ten carbon atoms optionally substituted with one or more heteroatoms selected from halogen, oxygen, nitrogen, and sulfur. The above structures for $R^3$ can be attached to the remainder of the c-Rel inhibiting compound by any of the ring carbon atoms or ring heteroatoms, where applicable, and/or $R^3$ can be attached to the remainder of the c-Rel inhibiting compound by the $R^4$ group, in which case the $R^4$ group functions as a linker, where applicable. In addition, each monocyclic ring or each ring in a fused ring system may be substituted with one or more additional $R^4$ groups than the one shown, wherein the additional $R^4$ groups may function as groups or linkers where applicable.

The groups $X^1$, $X^2$, and $X^3$ in Formula (1) are each independently selected from oxygen and sulfur atoms. In one set of embodiments, $X^1$, $X^2$, and $X^3$ are all oxygen atoms. In other embodiments, at least one of $X^1$, $X^2$, and $X^3$ is a sulfur atom. For example, in a first set of embodiments, one of $X^1$, $X^2$, and $X^3$ is a sulfur atom, with the remaining two of $X^1$, $X^2$, and $X^3$ being oxygen atoms. In a second set of embodiments, two of $X^1$, $X^2$, and $X^3$ are sulfur atoms, one of $X^1$, $X^2$, and $X^3$ being an oxygen atom. In a third set of embodiments, $X^1$, $X^2$, and $X^3$ are all sulfur atoms.

In particular embodiments of Formula (1), $R^3$ is a fused ring system, as described above. Compounds of this subclass can be conveniently expressed by the following chemical structure:

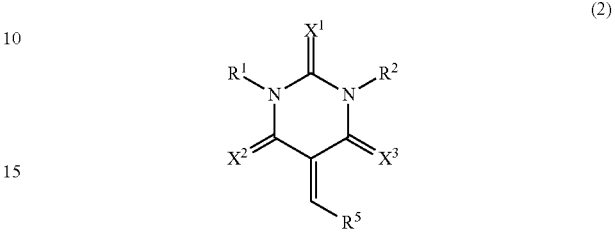

(2)

In Formula (2), $R^1$ and $R^2$ are as defined under Formula (1), including any of the generic or specific exemplary groups or combinations thereof provided therein. The groups $X^1$, $X^2$, and $X^3$ in Formula (2) are each independently selected from oxygen and sulfur atoms, as provided above under Formula (1). The group $R^5$ represents any one of the generic or specific exemplary fused ring systems described above for $R^3$ under Formula (1).

Formulas (1) and (2) are meant to encompass all physical forms of the shown structures. For example, in the case where the compound includes one or more stereocenters, all enantiomeric and diastereomeric forms, as well as mixtures thereof, including racemic mixtures, are encompassed by Formulas (1) and (2). The formulas also encompass any physiologically acceptable salt or solvate of any of the c-Rel inhibiting compounds described above. Acceptable salts and solvates can be made by any of the techniques known in the art. As known in the art, a salt can be produced by reacting a basic portion (e.g., amino) of the active compound with a Bronsted acid, such as HCl or $H_2SO_4$, or with a Lewis acid, such as $CH_3Br$. If desired, the initially introduced anion or cation can be exchanged with another anion or cation. As also known in the art, a solvate can be produced by contacting, dissolving, or otherwise treating the active compound with a solvent under conditions where one, two, or more solvent molecules remain associated with each molecule of the active ingredient. When the solvent is or includes water, the solvate may be a hydrate form of the compound. The formulas also encompass all crystalline, polycrystalline, or amorphous forms of the c-Rel inhibiting compounds.

Some examples of specific c-Rel inhibiting compounds encompassed by Formula (1) or (2) are given in Table 1 below:

TABLE 1

Examples of specific Rel inhibitors of the invention

| Reference | Name | Structure | MW |
|---|---|---|---|
| DHMEQ | Dehydroxymethyl-epoxyquinomycin | 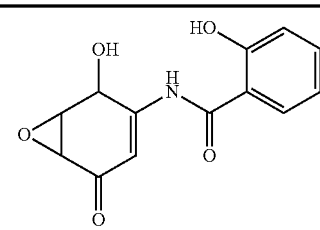 | 216.3 |

TABLE 1-continued

Examples of specific Rel inhibitors of the invention

| Reference | Name | Structure | MW |
|---|---|---|---|
| Plumbagin | Plumbagin | 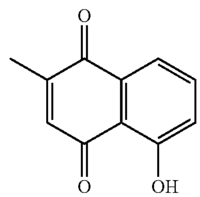 | 174.1 |
| BA-001 | 5-(2,4-dimethoxybenzylidene)-2-thioxodihydro-pyrimidine-4,6(1H,5H)-dione | 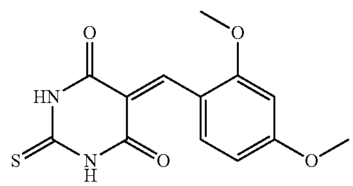 [SMILES: COc1ccc(C=C2C(=O)NC(=S)NC2=O)c(OC)c1] | 292.3 |
| BA-002 | 5,5'-(1,4-phenylenebis(methan-1-yl-1-ylidene)) dipyrimidine-2,4,6 (1H,3H,5H)-trione | 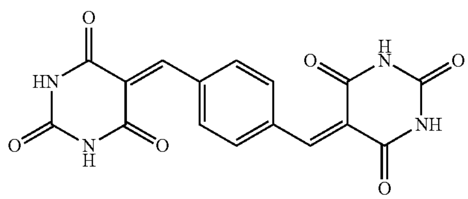 [SMILES: O=C1NC(=O)C(=Cc2ccc(C=C3C(=O)NC(=O)NC3=O)cc2)C(=O)N1] | 354.2 |
| BA-003 | 5-(5-chloro-2-methoxybenzylidene)-1,3-dimethyl-pyrimidine-2,4,6(1H,3H,5H)-trione | 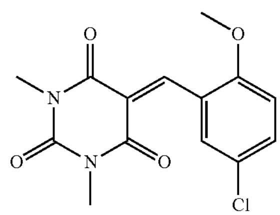 [SMILES: COc1ccc(Cl)cc1C=C1C(=O)N(C)C(=O)N(C)C1=O] | 304.2 |
| BA-004 | 1,3-dimethyl-5-(3-(2-(4-nitrophenoxy)-ethoxy)benzylidene) pyrimidine-2,4,6(1H,3H,5H)-trione | 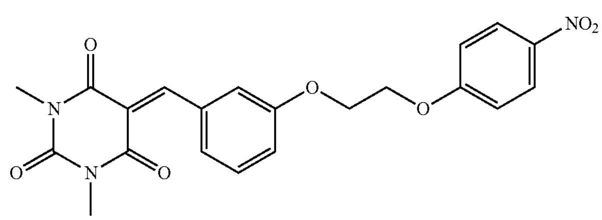 [SMILES: CN1C(=O)C(=Cc2cccc(OCCOc3ccc([N+](=O)[O-])cc3)c2)C(=O)N(C)C1=O] | 425.4 |
| BA-005 | 2-(4-((1,3-dimethyl-2,4,6-trioxotetrahydro-pyrimidin-5(6H)-ylidene)methyl)-2-methoxyphenoxy)-5-nitrobenzonitrile | 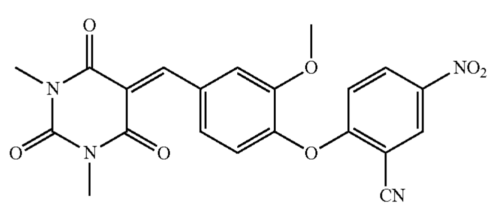 [SMILES: COc1cc(C=C2C(=O)N(C)C(=O)N(C)C2=O)ccc1Oc1ccc([N+](=O)[O-])cc1C#N] | 436.4 |
| BA-006 | 5-(2-(2-chlorobenzyloxy)-benzylidene)-1,3-dimethylpyrimidine-2,4,6(1H,3H,5H)-trione | 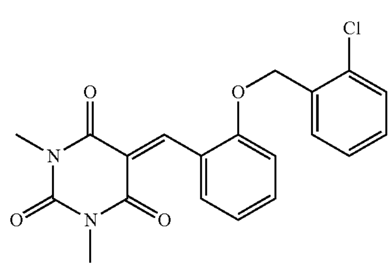 [SMILES: CN1C(=O)C(=Cc2ccccc2OCc2ccccc2Cl)C(=O)N(C)C1=O] | 384.8 |

TABLE 1-continued

Examples of specific Rel inhibitors of the invention

| Reference | Name | Structure | MW |
|---|---|---|---|
| BA-007 | 5-(3-(2-chlorobenzyloxy)benzylidene)-1,3-dimethylpyrimidine-2,4,6(1H,3H,5H)-trione | 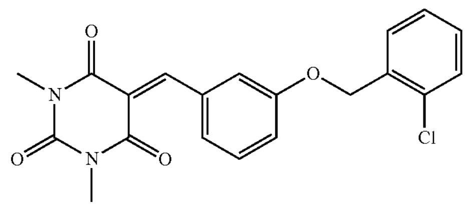 [SMILES: CN1C(=O)C(=Cc2cccc(OCc3ccccc3Cl)c2)C(=O)N(C)C1=O] | 384.8 |
| BA-008 | 5-(2-(4-chlorobenzyloxy)benzylidene)pyrimidine-2,4,6(1H,3H,5H)-trione | 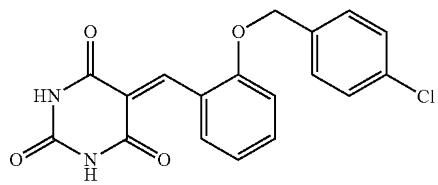 [SMILES: O=C1NC(=O)C(=Cc2ccccc2OCc2ccc(Cl)cc2)C(=O)N1] | 356.7 |
| BA-009 | 5-((4-methoxynaphthalen-1-yl)methylene)pyrimidine-2,4,6(1H,3H,5H)-trione | 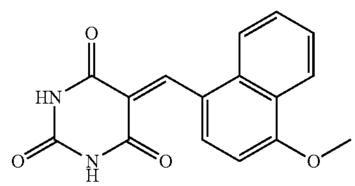 [SMILES: COc1ccc(C=C2C(=O)NC(=O)NC2=O)c2ccccc12] | 296.3 |
| BA-010 | 5-(2,4-dihydroxybenzylidene)2-thioxodihydro-pyrimidine-4,6(1H,5H)-dione | 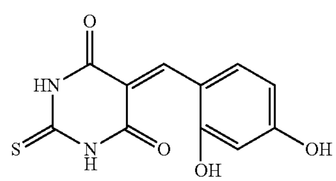 [SMILES: O=C1NC(=S)NC(=O)C1=Cc1ccc(O)cc1O] | 264.3 |
| BA-011 | 5-((6-bromo-2-hydroxynaphthalen-1-yl)methylene)-2-thioxodihydro-pyrimidine-4,6(1H,5H)-dione | 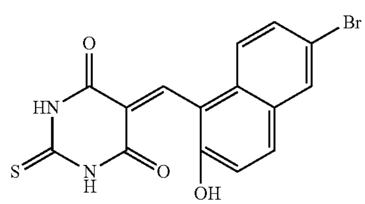 [SMILES: O=C1NC(=S)NC(=O)C1=Cc1c(O)ccc2cc(Br)ccc12] | 377.2 |
| BA-012 | 5-(2,4-dimethoxybenzylidene)-6-thioxohydropyrimidine-2,4(1H,3H)-dione | 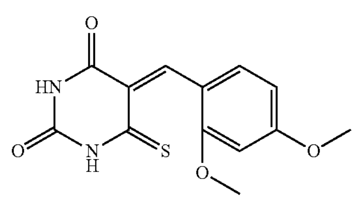 [SMILES: COc1ccc(/C=C2/C(=O)NC(=O)NC2=S)c(OC)c1] | 292.3 |
| BA-013 | 5-((2-methoxynaphthalen-1-yl)methylene)-2-thioxo-1-(m-tolyl)dihydropyrimidine-4,6(1H,5H)-dione | 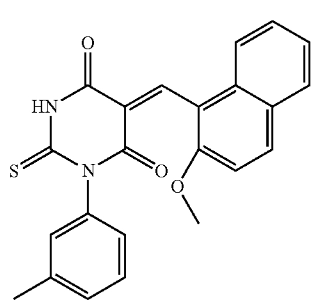 [SMILES: COc1ccc2ccccc2c1/C=C1/C(=O)NC(=S)N(c2cccc(C)c2)C1=O] | 402.5 |

TABLE 1-continued

Examples of specific Rel inhibitors of the invention

| Reference | Name | Structure | MW |
|---|---|---|---|
| BA-014 | 5-((2-methoxynaphthalen-1-yl)methylene)-1-phenyl-2-thioxo-dihydropyrimidine-4,6(1H,5H)-dione | 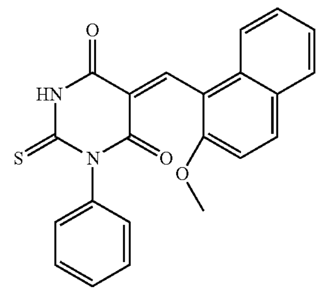 [SMILES: COc1ccc2ccccc2c1/C=C1/C(=O)NC(=S)N(c2ccccc2)C1=O] | 388.4 |
| BA-015 | 5-((2-ethoxynaphthalen-1-yl)methylene)-1-(4-methoxyphenyl)-2-thioxodihydropyrimidine-4,6(1H,5H)-dione | 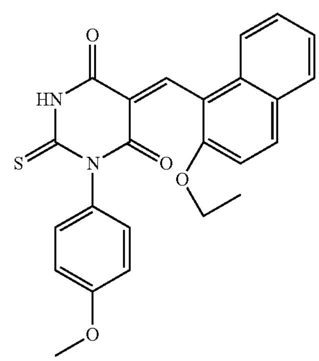 [SMILES: CCOc1ccc2ccccc2c1/C=C1/C(=O)NC(=S)N(c2ccc(OC)cc2)C1=O] | 432.5 |
| BA-016 | 5-((2-methoxynaphthalen-1-yl)methylene)-2-thioxo-1-(o-tolyl)dihydropyrimidine-4,6(1H,5H)-dione | 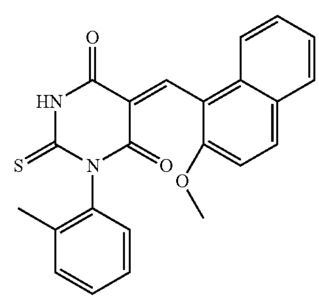 [SMILES: COc1ccc2ccccc2c1/C=C1/C(=O)NC(=S)N(c2ccccc2C)C1=O] | 402.5 |
| BA-017 | 1-ethyl-2-thioxo-5-(2,4,6-trimethoxybenzylidene)dihydropyrimidine-4,6(1H,5H)-dione | 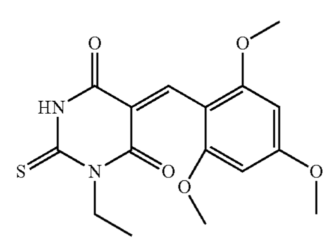 [SMILES: CCN1C(=O)/C(=C\c2c(OC)cc(OC)cc2OC)C(=O)NC1=S] | 350.4 |
| BA-018 | 1,3-dimethyl-2-thioxo-5-(2,4,6-trimethoxybenzylidene)dihydropyrimidine-4,6(1H,5H)-dione | 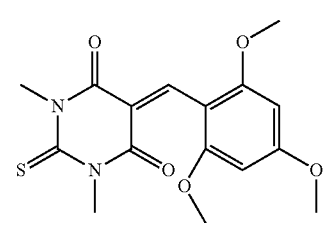 [SMILES: COc1cc(OC)c(C=C2C(=O)N(C)C(=S)N(C)C2=O)c(OC)c1] | 350.4 |

TABLE 1-continued

Examples of specific Rel inhibitors of the invention

| Reference | Name | Structure | MW |
|---|---|---|---|
| BA-019 | 2-thioxo-5-(2,4,6-trimethoxybenzylidene)dihydropyrimidine-4,6(1H,5H)-dione | 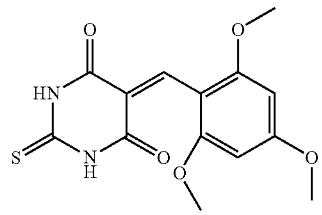 [SMILES: COc1cc(OC)c(C=C2C(=O)NC(=S)NC2=O)c(OC)c1] | 322.3 |
| BA-020 | 5-((2-ethoxynaphthalen-1-yl)methylene)-1-phenyl-2-thioxodihydropyrimidine-4,6(1H,5H)-dione | 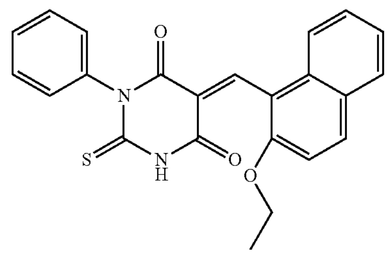 [SMILES: CCOc1ccc2ccccc2c1/C=C1\C(=O)NC(=S)N(c2ccccc2)C1=O] | 442.5 |
| BA-021 | 5-((2,7-dimethoxynaphthalen-1-yl)methylene)-1,3-dimethyl-2-thioxodihydropyrimidine-4,6(1H,5H)-dione | 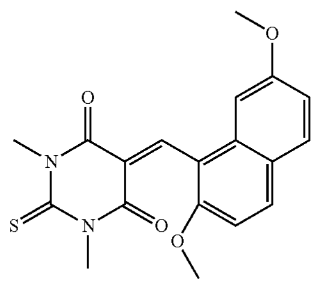 [SMILES: COc1ccc2ccc(OC)c(C=C3C(=O)N(C)C(=S)N(C)C3=O)c2c1] | 370.4 |
| BA-022 | 5-((2-methoxynaphthalen-1-yl)methylene)-2-thioxodihydropyrimidine-4,6(1H,5H)-dione | 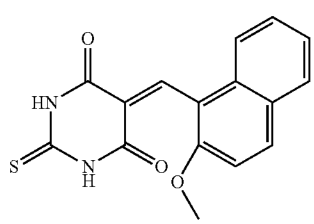 [SMILES: COc1ccc2ccccc2c1C=C1C(=O)NC(=S)NC1=O] | 312.3 |
| BA-023 | 5-((4-methoxynaphthalen-1-yl)methylene)-2-thioxodihydropyrimidine-4,6(1H,5H)-dione | 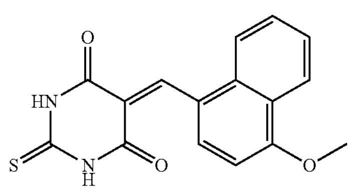 [SMILES: COc1ccc(C=C2C(=O)NC(=S)NC2=O)c2ccccc12] | 312.3 |
| BA-024 | 5-((2-((4-chlorobenzyl)oxy)naphthalen-1-yl)methylene)-2-thioxodihydropyrimidine-4,6(1H,5H)-dione | 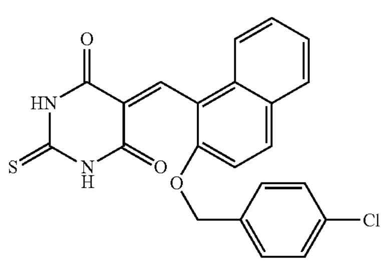 [SMILES: O=C1NC(=S)NC(=O)C1=Cc1c(OCc2ccc(Cl)cc2)ccc2ccccc12] | 422.9 |

TABLE 1-continued

Examples of specific Rel inhibitors of the invention

| Reference | Name | Structure | MW |
|---|---|---|---|
| BA-025 | 5-((2-methoxynaphthalen-1-yl)methylene)-1-methylpyrimidine-2,4,6(1H,3H,5H)-trione | 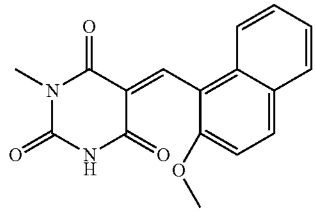 [SMILES: COc1ccc2ccccc2c1/C=C1\C(=O)NC(=O)N(C)C1=O] | 310.3 |
| BA-026 | 5-((2-ethoxynaphthalen-1-yl)methyl)-1-(4-methoxyphenyl)-2-thioxodihydropyrimidine-4,6(1H,5H)-dione | 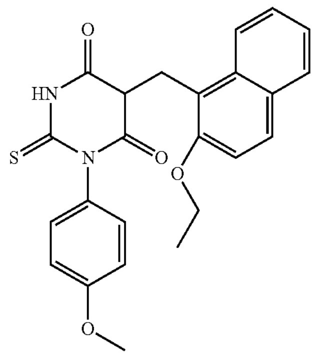 [SMILES: CCOc1ccc2ccccc2c1CC1C(=O)NC(=S)N(c2ccc(OC)cc2)C1=O] | 434.5 |
| BA-027 | 1-(4-chlorophenyl)-5-((2-ethoxynaphthalen-1-yl)methyl)-2-thioxodihydropyrimidine-4,6(1H,5H)-dione | 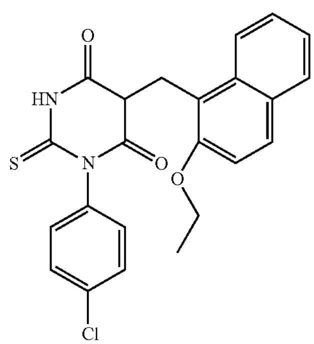 [SMILES: CCOc1ccc2ccccc2c1CC1C(=O)NC(=S)N(c2ccc(Cl)cc2)C1=O] | 438.9 |
| BA-028 | 5-((2-methoxynaphthalen-1-yl)methylene)-2-thioxo-1-(p-tolyl)dihydropyrimidine-4,6(1H,5H)-dione | 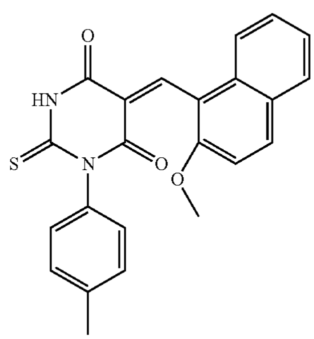 [SMILES: COc1ccc2ccccc2c1/C=C1/C(=O)NC(=S)N(c2ccc(C)cc2)C1=O] | 402.5 |
| BA-029 | 5-((2-methoxynaphthalen-1-yl)methylene)-1-(naphthalen-1-yl)-2-thioxodihydropyrimidin-4,6(1H,5H)-dione | 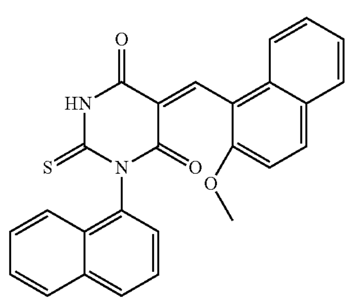 [SMILES: COc1ccc2ccccc2c1/C=C1/C(=O)NC(=S)N(c2cccc3ccccc23)C1=O] | 438.5 |

TABLE 1-continued

Examples of specific Rel inhibitors of the invention

| Reference | Name | Structure | MW |
|---|---|---|---|
| BA-030 | 5-((2-methoxynaphthalen-1-yl)methylene)-1-(4-methoxyphenyl)-2-thioxodihydro-pyrimidine-4,6(1H,5H)-dione | 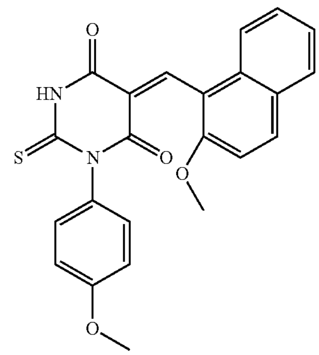 [SMILES: COc1ccc(N2C(=O)/C(=C\c3c(OC)ccc4ccccc34)C(=O)NC2=S)cc1] | 418.5 |
| BA-031 | 5-((2-methoxynaphthalen-1-yl)methylene)-1-(3-methoxyphenyl)-2-thioxodihydropyrimidine-4,6(1H,5H)-dione | 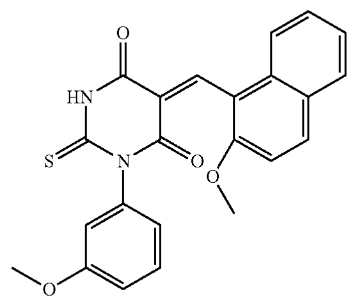 [SMILES: COc1cccc(N2C(=O)/C(=C\c3c(OC)ccc4ccccc34)C(=O)NC2=S)c1] | 418.5 |
| BA-032 | 1-(4-chlorophenyl)-5-((2-methoxynaphthalen-1-yl)methylene)-2-thioxodihydropyrimidine-4,6(1H,5H)-dione | 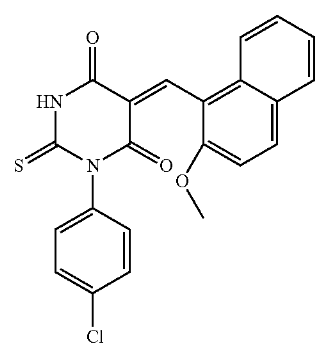 [SMILES: COc1ccc2ccccc2c1/C=C1/C(=O)NC(=S)N(c2ccc(Cl)cc2)C1=O] | 422.9 |
| BA-033 | 5-((2-((4-fluorobenzyl)oxy)naphthalen-1-yl)methylene)-1-phenyl-2-thioxo-dihydropyrimidine-4,6(1H,5H)-dione | 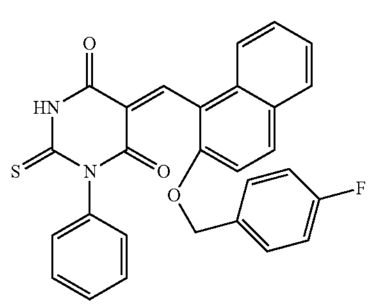 [SMILES: O=C1NC(=S)N(c2ccccc2)C(=O)/C1=C\c1c(OCc2ccc(F)cc2)ccc2ccccc12] | 482.5 |

TABLE 1-continued

Examples of specific Rel inhibitors of the invention

| Reference | Name | Structure | MW |
|---|---|---|---|
| BA-034 | 5-((2,7-dimethoxynaphthalen-1-yl)methylene)-1-(3-fluorophenyl)-2-thioxodihydropyrimidine-4,6(1H,5H)-dione | 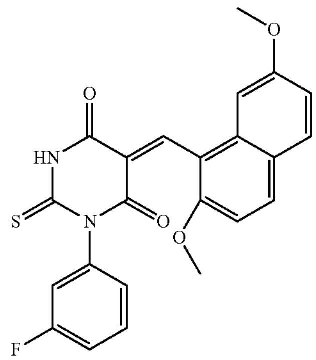 [SMILES: COc1ccc2ccc(OC)c(/C=C3/C(=O)NC(=S)N(c4cccc(F)c4)C3=O)c2c1] | 436.5 |
| BA-035 | 5-((2,7-dimethoxynaphthalen-1-yl)methylene)-2-(2-fluorophenyl)-2-thioxodihydropyrimidine-4,6(1H,5H)-dione | 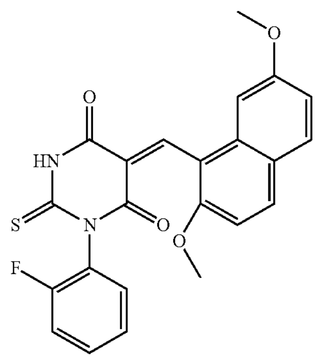 [SMILES: COc1ccc2ccc(OC)c(/C=C3/C(=O)NC(=S)N(c4ccccc4F)C3=O)c2c1] | 436.5 |
| BA-036 | 5-(anthracen-9-ylmethylene)-1-(2-fluorophenyl)-2-thioxodihydropyrimidine-4,6(1H,5H)-dione | 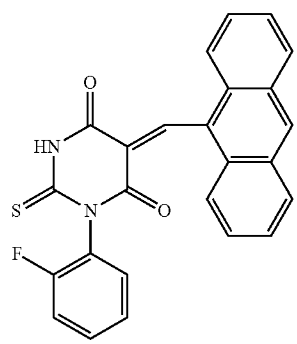 [SMILES: O=C1NC(=S)N(c2ccccc2F)C(=O)/C1=C\c1c2ccccc2cc2ccccc12] | 426.5 |
| BA-037 | 1-(3,5-dimethylphenyl)-2-thioxo-5-(2,4,6-trimethoxybenzylidene)dihydropyrimidine-4,6(1H,5H)-dione | 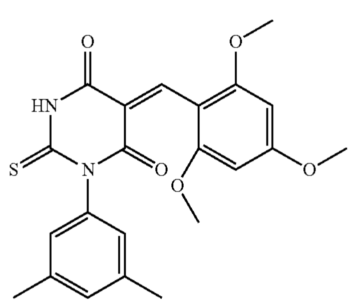 [SMILES: COc1cc(OC)c(/C=C2/C(=O)NC(=S)N(c3cc(C)cc(C)c3)C2=O)c(OC)c1] | 426.5 |

TABLE 1-continued

Examples of specific Rel inhibitors of the invention

| Reference | Name | Structure | MW |
|---|---|---|---|
| BA-038 | 1-(4-chlorophenyl)-2-thioxo-5-(2,4,6-trimethoxybenzylidene)dihydropyrimidine-4,6(1H,5H)-dione | 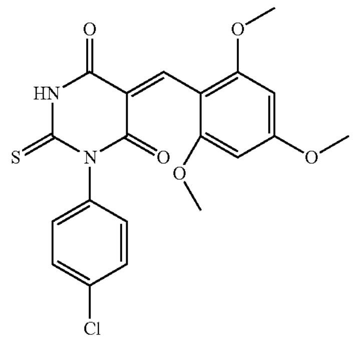 [SMILES: COc1cc(OC)c(/C=C2/C(=O)NC(=S)N(c3ccc(Cl)cc3)C2=O)c(OC)c1] | 432.9 |
| BA-039 | 5-((2,4-dimethoxynaphthalen-1-yl)methylene)-2-thioxodihydropyrimidine-4,6(1H,5H)-dione | 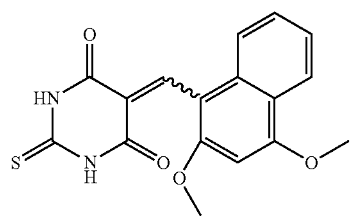 [SMILES: COc1cc(OC)c2ccccc2c1C=C1C(=O)NC(=S)NC1=O] | 342.4 |
| BA-040 | 5-((2,4-dimethoxy-naphthalen-1-yl)methylene)-1-methyl-2-thioxo-dihydropyrimidine-4,6(1H,5H)-dione | 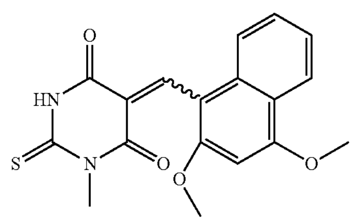 [SMILES: COc1cc(OC)c2ccccc2c1C=C1C(=O)NC(=S)N(C)C1=O] | 356.4 |
| BA-041 | 5-((2,4-dimethoxynaphthalen-1-yl)methylene)-1-phenyl-2-thioxodihydropyrimidine-4,6(1H,5H)-dione | 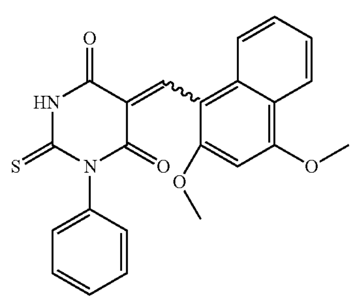 [SMILES: COc1cc(OC)c2ccccc2c1C=C1C(=O)NC(=S)N(c2ccccc2)C1=O] | 418.5 |

The invention is also directed to pharmaceutical compositions containing any one or more of the above-described c-Rel inhibiting compounds in a pharmaceutically acceptable carrier or excipient. The phrase "pharmaceutically acceptable excipient" or "pharmaceutically acceptable carrier", as used herein, refers to a pharmaceutically acceptable material, composition or vehicle, such as a liquid (diluent or excipient) or solid filler. In the pharmaceutical composition, the compound is generally dispersed in the physiologically acceptable carrier, by either being mixed (e.g., in solid form with a solid carrier) or dissolved or emulsified in a liquid carrier. The carrier should be compatible with the other ingredients of the formulation and physiologically safe to the subject. Any of the carriers known in the art can be suitable herein depending on the mode of administration. Some examples of suitable carriers include gelatin, fatty acids (e.g., stearic acid) and salts thereof, talc, vegetable fats or oils, gums and glycols, starches, dextrans, and the like.

The pharmaceutical composition can also include one or more auxiliary agents, such as stabilizers, surfactants, salts, buffering agents, additives, or a combination thereof. The stabilizer can be, for example, an oligosaccharide (e.g., sucrose, trehalose, lactose, or a dextran), a sugar alcohol (e.g., mannitol), or a combination thereof. The surfactant can be any suitable surfactant including, for example, those containing polyalkylene oxide units (e.g., Tween 20, Tween 80, Pluronic F-68), which are typically included in amounts of from about 0.001% (w/v) to about 10% (w/v). The salt or buffering agent can be any suitable salt or buffering agent, such as, for example, sodium chloride, or sodium or potassium phosphate, respectively. Some examples of additives include, for example, glycerol, benzyl alcohol, and 1,1,1-trichloro-2-methyl-2-propanol (e.g., chloretone or chlorobutanol). If required, the pH of the solutions can be suitably adjusted by inclusion of a pH adjusting agent.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Compositions and formulations for oral administration include powders or granules, suspensions or solutions in water or non-aqueous media, capsules, sachets or tablets. Thickeners, flavoring agents, diluents, emulsifiers, dispersing aids or binders may be desirable.

Compositions and formulations for parenteral, intrathecal, or intraventricular administration may include sterile aqueous solutions that may also contain buffers, diluents, and other suitable additives such as, but not limited to, penetration enhancers, carrier compounds, and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, liquid syrups, soft gels, suppositories, and enemas. The compositions of the present invention may also be formulated as suspensions in aqueous, non-aqueous or mixed media. Aqueous suspensions may further contain substances that increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature, these formulations vary in the components and the consistency of the final product.

The pharmaceutical composition may or may not also include one or more additional pharmaceutically active or auxiliary compounds outside the scope of Formulas (1) and (2). The additional active compound may, for example, suitably improve, augment, or otherwise suitably adjust the c-Rel inhibiting action of the compound of Formula (1) or (2), or suitably adjust or diminish an undesired aspect of the c-Rel inhibiting compound, such as a side effect. In some embodiments, the one or more additional pharmaceutically active compounds may serve to treat any of the diseases described herein and as provided in more detail in Table 2. In particular embodiments, the pharmaceutical composition includes one or more agents that enhance uptake of oligonucleotides at the cellular level. For example, cationic lipids, such as lipofectin (U.S. Pat. No. 5,705,188), cationic glycerol derivatives, and polycationic molecules, such as polylysine (WO 97/30731), can enhance the cellular uptake of oligonucleotides.

The pharmaceutical compositions of the present invention may additionally contain other adjunct or therapeutic components or agents conventionally found in pharmaceutical compositions. Thus, for example, the compositions may contain additional compatible pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, or salts for influencing osmotic pressure, buffers, colorings, flavorings and/or aromatic substances and the like, as long as they do not deleteriously interact with components of the formulation.

The invention further provides a kit comprising a c-Rel inhibitor in a pharmaceutically acceptable carrier. The kit can include any of the components typically used in the administration and use of a pharmaceutical. Thus, the kit may include any apparatus components necessary in the administration of the pharmaceutical, such as, for example, a packaged pharmaceutically acceptable dose of the pharmaceutical, instructions for use of the pharmaceutical, and accessories for administration, such as a needle or pad, if applicable, and optionally, any additional therapeutic agents to be co-administered to a subject.

The c-Rel inhibiting compounds described above can be synthesized by any of the suitable methods known in the art, or as further described below. For example, compounds described above having a thiopyrimidinedione (one of $X^1$, $X^2$, and $X^3$ is S and two are O) or pyrimidinetrione (all of $X^1$, $X^2$, and $X^3$ are O) moiety can be prepared according to the following generic scheme:

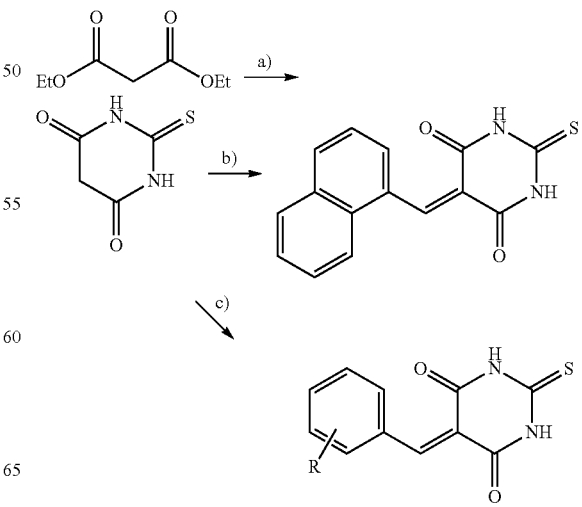

a) NaOEt, 2 eq./EtOH/thiourea; b) 1-naphthylaldehyde, which may be optionally substituted with one or more heteroatoms or functionalized with one or more hydrocarbon groups R, 1 eq./EtOH; c) relevant aldehyde (R-substituted benzaldehyde), 1 eq./EtOH, where R can be any of the hydrocarbon groups described above.

Synthetic Route 2

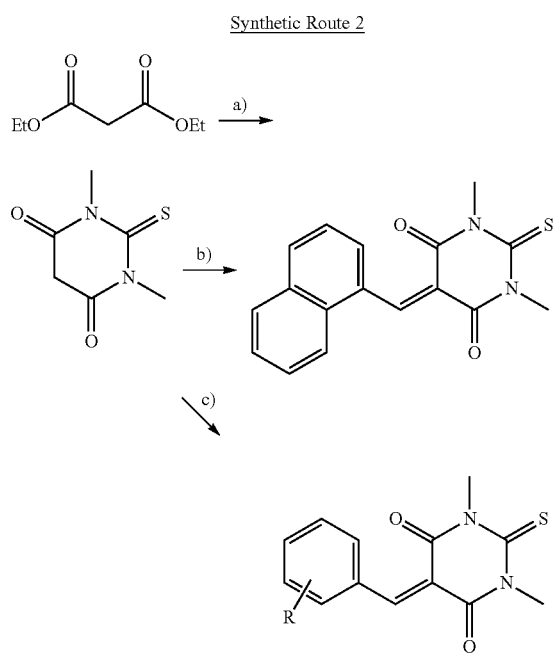

a) NaOEt, 2 eq./EtOH/dimethylthiourea; b) 1-naphthylaldehyde, which may be optionally substituted with one or more heteroatoms or functionalized with one or more hydrocarbon groups R, 1 eq./EtOH; c) relevant aldehyde (R-substituted benzaldehyde), 1 eq./EtOH, where R can be any of the hydrocarbon groups described above.

Synthetic Route 3

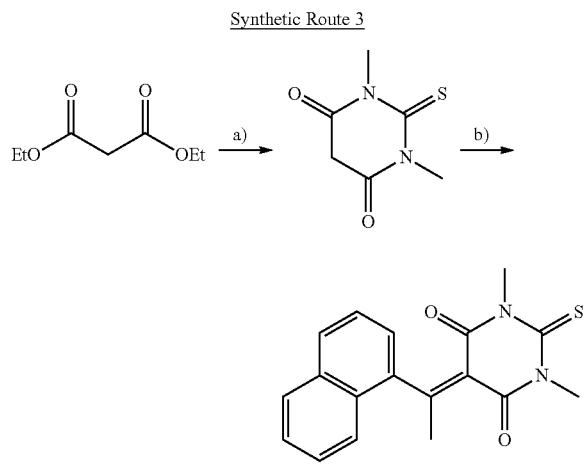

a) NaOEt, 2 eq./EtOH/dimethylthiourea; b) 1-naphthylaldehyde (i.e., 1-acetylnaphthalene or methyl 1-naphthyl ketone), which may be optionally substituted with one or more heteroatoms or functionalized with one or more hydrocarbon groups R, 2 eq./EtOH.

Synthetic Route 4

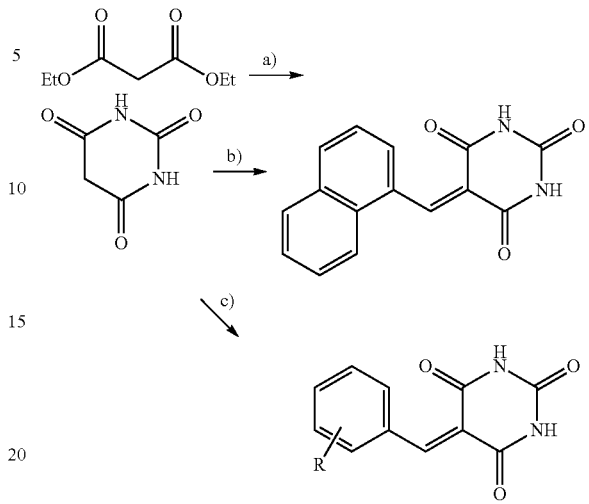

a) NaOEt, 2 eq./EtOH/urea; b) 1-naphthylaldehyde, which may be optionally substituted with one or more heteroatoms or functionalized with one or more hydrocarbon groups R, 1 eq./EtOH; c) relevant aldehyde (R-substituted benzaldehyde), 1 eq./EtOH, where R can be any of the hydrocarbon groups described above.

Compounds having a dithiopyrimidinone (two of $X^1$, $X^2$, and $X^3$ are S and one is O) or pyrimidinetrithione (all of $X^1$, $X^2$, and $X^3$ are S) moiety can be synthesized by analogous means, such as by starting with a thiomalonate or dithiomalonate ester, respectively. Alternatively, a thiopyrimidinedione compound, such as any of the above, may function as an intermediate compound by reacting the thiopyrimidinedione with a substance that converts one or both carbonyl groups to thiocarbonyl groups, such as by reaction with Lawensson reagent by methods well known in the art. Alternatively, thiopyrimidinedione can be converted into chloropyrimidinethiol or dichloropyrimidinethiol intermediate with a chlorinating agent such as $POCl_2$ prior to the conversion to dithiopyrimidinone or pyrimidinetrithione by reacting intermediate with ammonium sulfide ($(NH_4)_2S$) or sodium sulfide.

In another aspect, the invention is directed to treating a subject (patient) having a disease or condition associated with excessive c-Rel activity, i.e., c-Rel overexpression or c-Rel hyperactivity, since the compounds described above according to Formulas (1) and (2) target c-Rel or associated proteins. The subject may have or be afflicted with the disease or condition with or without observable symptoms. In the method, the patient is administered an effective amount (dosage) of any of the c-Rel inhibitor compounds described above to treat or prevent a disease or condition resulting from excessive c-Rel activity, such as any of the diseases or conditions provided in Table 2. More generally, the method involves contacting or targeting a cell or cell population expressing a c-Rel gene with a c-Rel activity inhibitor, wherein the cell or cell population is in the patient. In some embodiments, the cell is a human cell, a cancer cell, B-lymphocyte, a T-lymphocyte, an antigen presenting cell, or an inflamed cell. In some embodiments, the cell is in an organism (e.g., a human or a non-human mammal). In some embodiments, the subject exhibits symptoms of cancer (e.g., those described in Table 2). In other embodiments, the subject exhibits symptoms of an allergy, asthma, inflammatory, or autoimmune disease (e.g., those described in Table 2). In yet other embodiments, the subject has undergone an organ transplant or bone marrow transfer, and experienced organ rejection or graft-versus-host disease (e.g., those described in Table 2). In still other embodiments, the subject has experienced bone loss or sepsis.

In some embodiments, inhibition of c-Rel results in a phenotype selected from the group including, but not limited to, cell growth arrest, apoptosis, immune suppression, T-regulatory cell induction, and immune tolerance induction. In some embodiments, inhibiting c-Rel activity comprises reducing binding of c-Rel to c-Rel recognition sites on c-Rel target genes. In other embodiments, inhibiting c-Rel activity comprises interrupting the interaction of c-Rel with a c-Rel transcription co-activator, transcription mediator, or other transcription factors. In yet other embodiments, inhibiting c-Rel activity comprises altering c-Rel structural conformation to an inactive state.

In some embodiments, the disease is an inflammatory disease (e.g., asthma, acute respiratory distress, sepsis, hepatitis, colitis, inflammatory bowel disease, ischemia-reperfusion injury, or atherosclerosis), an autoimmune disease (e.g., lymphoproliferative disease, systemic lupus erythematosus, rheumatoid arthritis, multiple sclerosis, or ankylosing spondylitis), bone loss (e.g., bone loss resulting from osteoporosis, arthritis, inflammation, or autoimmune disease), organ transplant rejection (e.g., graft vs. host disease or bone marrow transplant rejection), immune therapy (e.g., induction of immune tolerance), or cancer (e.g., B cell lymphoma, Burkitt's lymphoma, chronic lymphocytic leukemia, multiple myeloma, lymphoma with Pten mutation, leukemia with Pten mutation, Cowden's syndrome, tumors with Pten mutation, prostate cancer, breast cancer, metastatic tumor hepatocellular carcinoma, colon cancer, gastrointestinal cancer, melanoma, non-small cell lung cancer, pancreatic cancer). In the particular case of cancer, the cancerous or pre-cancerous condition (neoplastic condition) can be located in any internal organ of the body. Some examples of applicable body parts containing cancer cells include the heart, lungs, stomach, intestines, breasts, prostate, ovaries, pancreas, kidney, liver, bladder, uterus, colon, or rectum. The cancer or neoplasm may include the presence of one or more carcinomas, sarcomas, lymphomas, blastomas, or teratomas (germ cell tumors). The cancer can also be a form of leukemia.

The aforementioned diverse roles of c-Rel in many aspects of immune cell functions indicates that c-Rel is a key culprit in many inflammatory and autoimmune diseases and that blocking c-Rel protects or prevents the onset of those diseases. Indeed, c-Rel blockade has been shown to be beneficial in preventing the onset of several disease models in animals (e.g., asthma, experimental autoimmune encephalomyelitis, collagen induced arthritis, diabetes, pancreatic islet transplantation, and heart transplantation). Based on the fundamental function of c-Rel in immune cells, it is contemplated that c-Rel blockade is also beneficial for treating the following pathological conditions (see Table 2). The effectiveness of some direct inhibitors of c-Rel of this invention for some of these conditions is described in the Examples.

Acute and chronic inflammation: Inflammation in the lung and respiratory system induced by allergens or viral and bacterial infection is caused by the infiltration of immune cells to the lung that produce inflammatory cytokines or allergic mediators (e.g. IgE). In the situation of acute respiratory distress syndrome (ARDS) caused by viral (e.g. influenza virus, bird flu virus H5N1, SARS virus) and bacterial infection can be deadly, as the "cytokine storm" produced by infiltrating immune cells can lead to lung edema and impair gas exchange of the lungs. Sepsis is yet another acute response manifested by systemic release of inflammatory cytokines and mediators due to severe bacterial invasion into the bloodstream. At present, there is no effective therapy for ARDS and sepsis. Hepatitis, colitis, inflammatory bowel diseases, and atherosclerosis are other examples of unresolved chronic inflammation in specific tissues. In each of these cases, NF-kB has been shown to play a pathological role, and therapeutic agents (commercial or experimental) that are effective in treating these disorders have been shown to block NF-kB activation. Many studies have shown that Rel family member activation is activated during ischemia and that Rel family activation is responsible for ischemia reperfusion injury of multiple organs including brain, heart, and kidney. Most studies only focus on the role of NF-kB (p50, p65) in the aforementioned pathological conditions, without addressing the role of c-Rel. The present invention considers c-Rel as an important inflammatory mediator for these organ-specific inflammatory diseases as well as reperfusion tissue injury. Taken together, the present invention provides methods and compositions for inhibiting c-Rel as a therapy for ARDS, respiratory inflammatory disorders, sepsis, organ-specific inflammation, and ischemic injury.

Autoimmune diseases: Autoimmune diseases arise from the host immune system attacking its own tissues. There are at least 80 autoimmune diseases afflicting various tissues such as joints (rheumatoid arthritis), central nervous system (multiple sclerosis), intestine (Crohn's disease), and skin (psoriasis). It is estimated that autoimmune diseases affect 5 to 8 percent of the American population, or up to 23.5 million people. Previous studies on c-Rel knockout mice have demonstrated that blocking c-Rel activity protects the animals from developing autoimmune encephalomyelitis, type I diabetes, and collagen-induced arthritis. The present invention provides methods and compositions for blocking c-Rel in the treatment of autoimmune diseases. Recent success of anti-TNF therapy in treating patients with rheumatoid arthritis and ankylosing spondylitis suggest that inflammatory cytokines play important pathological roles in these diseases. Since c-Rel is involved in the expression of many of the inflammatory cytokines including IL-2, TNF and IL-6, the present invention provides methods and compositions for blocking c-Rel as a therapeutic in these diseases. Autoimmune diseases arise from the breakdown of immune tolerance to self-tissues or self-antigens. If the antigen is widely expressed (e.g. nuclear DNA), then the disease is systemic. By contrast, if the self-antigen is only expressed in a particular tissue (e.g. insulin), then the disease is tissue-specific (e.g. pancreatic cells in the case of diabetes). Recent advances in immunology have identified many genes whose expression or alteration is associated with the onset of tissue-specific or systemic autoimmune diseases. Most of these genes have functions in modulating antigen receptor (TCR/BCR) activation threshold, in which c-Rel is a key effector of the antigen-receptor signaling pathway. Therefore, the present invention provides methods and compositions for specific inhibition of c-Rel activity in autoreactive immune cells as a therapeutic for tissue-specific and systemic autoimmune diseases, including, but not limited to, rheumatoid arthritis, multiple sclerosis, diabetes, Crohn's disease, Grave's diseases, Hashimoto's thyroiditis, myasthenia gravis, Psoriasis, systemic lupus erythematosus (SLE), lymphoproliferative disease (ALPS), and Sjogren's syndrome.

Organ transplantation rejection and graft-versus-host disease: It has been well documented that host T cells are primarily responsible for the rejection of allografts provided by HLA-mismatched donors. Such activation of host T cells is mediated via TCR-interaction with allo-MHC molecules on the graft. Since c-Rel is responsible for TCR-mediated T cell proliferation and effector function, the present invention provides methods and compositions for blocking c-Rel in host immune cells as an immunosuppressive agent and treatment and prevention of allograft rejection. c-Rel inhibitors find use as immunosuppressive agents in the transplantation of a number of tissues, including, but not limited to, bone marrow, major organs (heart, lung, kidney, liver), as well as soft tissues (skin, cartilage, bone). In other embodiments, c-Rel suppression is used in the prevention of graft vs. host disease.

Bone loss: C-Rel and NF-kB have been shown to be involved in bone loss and the osteoporosis process. Several studies have shown that IKK-beta leads to the activation of c-Rel, RelB, and RelA (p65) in osteoclasts, which leads to osteoclast survival and inflammation-induced bone loss. Indeed, knockout of p50/p52 of the NF-kB members led to osteoporosis, due to overactivation of the remaining NF-kB members. By contrast, inhibiting IKK activity blocks osteoclastogenesis and prevents arthritic bone destruction. Thus, in some embodiments, the present invention provides methods and compositions for inhibiting conventional NF-kB or c-Rel for the prevention and treatment of osteoporosis, as well as of arthritic or inflammation-mediated bone destruction.

Taken together, c-Rel is a therapeutic target for cancer, autoimmune diseases, inflammation, diabetes, organ transplantation, graft-versus-host disease, and bone loss. Accordingly, in some embodiments, the present invention provides c-Rel inhibitors that reduce the production of multiple inflammatory cytokines, the expression of costimulatory molecules, and the expression of cell survival and cell cycle regulators in lymphocytes (e.g., Example 6). As a result, c-Rel inhibitors dampen the activation of major types of immune cells, such as T-lymphocytes, B-lymphocytes, dendritic cells, macrophages, and antigen presenting cells at the core of the immunopathological conditions. The present invention also provides c-Rel inhibitors as adjuvant agents for inducing immune tolerance or the development of T-regulatory cells as novel therapies for autoimmune diseases and transplant rejection.

In some embodiments, the present invention provides evidence that blocking Rel prevents the development of EAE (an animal model of multiple sclerosis) (e.g., Example 7). In yet another embodiment, the present invention shows that inhibiting Rel activity in ex vivo bone marrow significantly reduced the incidence of graft-versus-host disease during bone marrow transfer (Example 8). Example 8 provides further evidence that blocking c-Rel with the inhibitors described herein significantly reduced the risk of graft-versus-host disease, while preserving anti-tumor activities in animal models mimicking bone marrow transfer in leukemia case.

Another important feature relevant to drug safety/toxicity profile is that the lack of c-Rel activity in c-Rel knockout mice does not have a serious impact on their systemic development, metabolism, or reproduction, nor does it cause cardiac fibrosis as seen in Cox2 knockout mice. This unique safety property is desirable, as it suggests that c-Rel inhibitors will not cause adverse effects as reported with the Cox2 inhibitors. In addition, targeting c-Rel avoids the systemic toxicities of corticosteroids and Cyclosporin/FK506.

C-Rel was initially identified as a proto-oncogene. Its viral counterpart v-Rel oncogene primarily transforms and immortalizes immature and mature T and B lymphoid, myeloid and dendritic cells from spleen and bone marrow and induces aggressive fatal lymphoma in infected young birds. The oncogenic potential of v-Rel was further demonstrated by experiments that demonstrated that transgenic mice expressing v-Rel under the control of T-cell tropic promoter developed aggressive T-cell leukemia/lymphoma in mice. By generating the c-Rel knockout mice, it has herein been shown that c-Rel regulates cell cycle proteins (E2F, cyclin E), anti-apoptotic molecules (Bcl-X, Bfl-1, Mcl-1), as well as several inflammatory cytokines (IL-2, IL-6, IL-12/IL23, IFN-γ, TNF), thus highlighting its tumorigenic potential in lymphoid cells. The role of c-Rel in tumorigenesis is consistent with the observation that c-Rel is the most oncogenic member among the Rel family by genetic approaches.

c-Rel is also associated with many cancers in human, due to its ability to prevent apoptosis (by inducing anti-apoptotic proteins) and to induce proliferation (via induction of cell cycle regulators). The fact that c-Rel is predominantly expressed in hematopoietic cells makes it one of the most prevalent oncoprotein in many B cell leukemias and lymphomas (Table 2). Several studies have reported the association of hyperactive Rel with B cell tumors, including CLL, primary effusion lymphoma (PEL), multiple myeloma (MM), and diffuse large B cell lymphoma (DLBCL). For example, the human c-Rel locus is amplified in a significant proportion of diffuse large cell lymphoma (23%), primary mediastinal B-cell lymphoma, follicular B-cell lymphoma, and Hodgkin's lymphoma. C-Rel gene rearrangement or over-expression is also detected in diffuse large cell lymphoma, follicular lymphoma, and non-small cell lung carcinoma. Additionally, constitutive or hyperactivate NF-kB/Rel has been detected in human B cell tumors including chronic lymphocytic leukemia (CLL). Freshly isolated unstimulated CLL B cells contain high levels of nuclear NF-kB/Rel activity consisting of c-Rel, p50, and p65. NF-kB/Rel activity can be further induced by CD40, which correlates with prolonged survival of the CLL cells in vitro. Other examples of B cell tumors that exhibit aberrant c-Rel activation include multiple myeloma, Burkitt's lymphoma, and mantle cell lymphoma.

For multiple myeloma, multiple mutations are known to be responsible for persistent activation of the "classical" and/or "alternative" Rel pathways. From this, it has been found that some multiple myeloma (MM) cells have over-expression of the positive regulators of the NF-kB pathway (e.g. CD40, TACI, NIK, NFKB1, NFKB2), whereas others have deletions or mutations in the negative regulators of the Rel signaling components (e.g. TRAF3, CYLD, cIAP1/2).

Similar findings were also reported in DLBCL in that mutations in multiple Rel upstream regulators were detected (e.g. A20, CARD11, TRAF2, TRAF3, TAK1, RANK). DLBCL were grouped into the activated B cell (ABC) and germinal center (GC) subtypes, based on distinct gene signatures. It was subsequently shown that a large fraction (~95%) of ABC type exhibited constitutive Rel transcription activity, as compared to smaller fraction (~47%) of GC type with Rel gene signature. When immunohistochemical staining was used to identify nuclear Rel activity, it was found that about 30% of DLBLC (for ABC and GC subtypes) have nuclear activity of both "classical" and "alternative" Rel activity.

In some embodiments, the present invention provides evidence that blocking Rel reduces the proliferation and growth of B cell tumors ex vivo and in xenograft animal models (e.g., Examples 4 and 5). The present invention is not limited to a particular mechanism. Indeed, an understanding of the mechanism is not necessary to practice the present invention. Nonetheless, it is contemplated that based on the observation that tumor B cells have acquired survival advantage in vivo, it is contemplated that constitutive c-Rel and/or NF-kB activity contributes to tumor cell survival. Rel transcription factors are known to regulate multiple anti-apoptotic molecules including Bcl-x, Bcl-2, Mcl-2, IAP, and FLIPs. It has herein been shown that c-Rel regulates cell cycle proteins (E2F, cyclin E), anti-apoptotic molecules (Bcl-X, Bfl-1, Mcl-1), as well as several inflammatory cytokines (IL-2, IL-6, IL-12/IL23, IFN-γ, TNF), thus highlighting its tumorigenic potential in lymphoid cells as well as epithelial derived solid tumors.

These observations make Rel family attractive therapeutic targets for treating B cell tumors, T cell leukemia, as well as Hodgkin and non-Hodgkin's diseases. In addition to lymphoid tumors, aberrant constitutive Rel activity has been found in many non-hematopoietic tumors and solid carcinoma, including breast cancer, prostate cancer, melanoma, colon cancer, ovarian cancer, and non-small cell lung cancer. For example, transgenic mice with human c-Rel gene under the control of the mouse mammary tumor virus (MMTV) long terminal repeat promoter develop mammary tumors with an average latency of 19.9 months. A high percentage of human breast tumors and tumor-derived cell lines have increased levels of constitutive nuclear NF-kB activity consisting of c-Rel, p50, Rel-B, and Bcl-3, and inhibiting NF-kB activity leads to cytotoxicity of the breast tumor cell lines. In some cases, activation of the Rel/NF-kB activity is coincident with malignant progression into metastasis or resistance to chemotherapy. Such progression may be attributed to the role of Rel/NF-kB in inducing genes involved in survival, proliferation, migration, and angiogenesis.

It has previously been demonstrated that suppression of c-Rel activity attenuates hyper-proliferation and lymphoma resulting from mutations in the Pten gene. The Pten gene is a tumor suppressor frequently mutated in a variety of solid tumors including metastatic prostate cancers, endometrial cancers, metastatic melanoma, and glioblastomas. Mutations of the Pten gene have also been documented in over 80% of individuals with Cowden's disease (CD). Pten mutations were also found in a variety of B cell lymphomas. Thus, blocking Rel activity, by pharmacological inhibitors, can be utilized for the treatment of cancers with Pten mutations.

Epidemiological studies have shown that ~15% of human deaths from cancer are associated with chronic viral or bacterial infections, suggesting a link between infection, inflammation, and cancer. For example, HCV infection is an important risk factor for hepatocellular carcinoma (HCC). A bacterium, *Helicobacter pylori* (*H. pylori*), is one of the main contributors to gastric cancer, the second most common cancer worldwide. It has been hypothesized that activation of Rel by the classical IKK-dependent pathway is a crucial mediator of inflammation-induced tumor growth and progression. Indeed, the hypothesis has been supported by two animal models: inflammation-associated liver cancer (a model for hepatoma) and inflammation-associated colon cancer (a model for colitis-associated cancer). These models suggest that Rel may promote tumor progression through inducing the expression of genes that encode secreted cytokines, growth factors, survival proteins, proteases, as well as factors for chemotaxis, migration, and angiogenesis.

Accordingly, in some embodiments, the present invention provides methods and compositions for targeting c-Rel in inflammation-associated cancers. In some embodiments, the present invention provides c-Rel activity inhibitors for the treatment of infection or chemical-induced malignancies including, but not limited to, HCC, colon cancer, gastrointestinal cancer, lung cancer, pancreatic cancer, bladder cancer, and esophageal cancer.

Experiments conducted during the course of development of the present invention identified a series of small molecules that inhibit c-Rel activity (see e.g., Examples 1 to 8). In some embodiments, the present invention provides therapies for treating and/or analyzing cancer, inflammatory, organ transplant rejection and autoimmune disease. In some embodiments, the methods inhibit c-Rel activity or biological functions (e.g., by inhibiting the interaction of c-Rel with binding partners). In other embodiments, the methods inhibit function by modulating c-Rel signaling regulators, c-Rel transcriptional activity, or c-Rel target gene expression. The present invention is not limited to the treatment of a specific condition or disease. An exemplary, non-limiting list of specific cancer inflammatory, and autoimmune disease and conditions are provided in Table 2 below.

TABLE 2

Disease indications applicable for c-Rel specific therapies

| Generic Disease | Specific disease indications benefited from c-Rel inhibition |
|---|---|
| Inflammatory diseases (acute and chronic) | Asthma and allergy |
| | Inflammatory pulmonary syndrome |
| | Acute respiratory distress syndrome (ARDS) |
| | Neonatal chronic lung disease |
| | Chronic obstructive pulmonary disease (COPD) |
| | Gram positive sepsis |
| | Gram negative sepsis |
| | Culture negative sepsis |
| | Fungal sepsis |
| | Systemic inflammatory response syndrome |
| | Hepatitis |
| | Colitis |
| | Inflammatory bowel disease (IBD) |
| | Ischemia-reperfusion injury |
| | Atherosclerosis |
| | Glomerulonephritis |
| | Pemphigus vulgaris |
| | Idiopathic thrombocytopenic purpura |
| | Aphthous ulcer |
| | Irtis |
| | Conjunctivitis |
| | Keratoconjunctivitis |
| | Cutaneous lupus erythematosus |
| | Vaginitis |
| | Proctitis |
| | Drug eruptions |
| | Leprosy reversal reaction |
| | Erythema nodosum leprosum |
| | Polychronditis |
| | Endotoxemia |
| | Lyme arthritis |
| | Infectious meningitis |
| | Rubella arthritis |
| | Eczema |
| | Allergic contact dermatitis |
| | Hypersensitivity pnemonitis |
| | Encephalomyelitis |
| | Type IV hypersensitivity |
| | Drug sensitivity |
| | Cachexia |
| | Cystic fibrosis |
| | Neutropenic fever |
| | Urosepsis |
| | Meningococcemia |
| | Trauma/hemorrhage |

TABLE 2-continued

Disease indications applicable for c-Rel specific therapies

| Generic Disease | Specific disease indications benefited from c-Rel inhibition |
|---|---|
| Autoimmune diseases: | Burns
Ionizing radiation exposure
Acute pancreatitis
Alcohol-induced hepatitis
Chronic inflammatory pathologies
Sickle cell anemia
Nephrosis
Atopic diseases
Hypersensitivity reactions
Allergic rhinitis
Hay fever
Perennial rhinitis
Endometriosis
Urticaria
Systemic
Anaphalaxis
Anti-receptor hypersensitivity reactions
Immune tolerance therapy via co-administration of allergens
Multiple Sclerosis (autoimmune encephalomyelitis)
Type I diabetes
Rheumatoid arthritis
Ankylosing spondylitis
Spondyloarthropathies
Crohn's disease (inflammatory bowel disease)
Grave's disease
Hashimoto's thyroiditis
Myasthenia gravis
Psoriasis
Systemic lupus erythematosus (SLE)
Lymphoproliferative disease (ALPS)
Sjogren's syndrome
Autoimmune neuropathies
Gullian-Barre syndrome
Autoimmune uveitis
Autoimmune hemolytic anemia
Pernicious anemia
Aplastic anemia
Pure red cell anemia
Autoimmune thrombocytopenia,
Temporal arteritis
Anti-phospholipid syndrome
Vasculitides
Wegener's granulomatosis
Behcet's disease
Dermatitis herpetiformis
Pemphigus vulgaris
Vitiligo
Primary biliary cirrhosis
Autoimmune hepatitis
Autoimmune oophoritis and orchitis
Autoimmune disease of the adrenal gland
Scleroderma
Polymyositis
Dermatomyositis
Autoimmune menagitis
Autoimmune dermatitis
Alopecia areata
Autoimmune uveitis
Allergic encephalomyelitis
Interstitial lung fibrosis
Seronegative arthropathies
Sarcoidosis
Orchitis/vasectomy reversal procedure
Raynoud's disease
Type B insulin-resistant diabetes
Antibody-mediated cytotoxicity
Type III hypersensitivity reactions
POEMS syndrome
Polyneuropathy
Organomegaly
Endocrinopathy
Monoclonal gammopathy
Skin changes syndrome
Pemphigus |

TABLE 2-continued

Disease indications applicable for c-Rel specific therapies

| Generic Disease | Specific disease indications benefited from c-Rel inhibition |
|---|---|
| Transplantation rejection | Mixed connective tissue diseases
Idiopathic Addison's disease
Post-MI cardiotomy syndrome
Wilson's disease
Hemachromatosis
Alpha-1-antitrypsin deficiency
Osteoporosis
Hypothalamic-pituitary-adrenal axis evaluation
Familial hematophagocytic lymphohistiocytosis
Pre eclampsia
Okt3 therapy
Anti-cd3 therapy
Cytokine therapy
Chemotherapy
Radiation therapy
Immune tolerance therapy via co-administration of self-antigens or self-tissues
Graft vs. host disease
Organ transplantation:
kidney
heart
liver
pancreas
Islet cells
lung
bone marrow
skin allograft
cartilage
bone graft
small bowel
fetal thymus implant
parathyroid
Xenograft rejection
Allograft rejection
Immune tolerance therapy via co-administration of allo-antigens or allo-tissues |
| Cancers: | Diffuse large cell lymphoma
Follicular B cell lymphoma
Chronic lymphocytic leukemia
Multiple myeloma
Burkitt's lymphoma
Primary mediastinal B-cell lymphoma
Hodgkin's lymphoma
Non-Hodgkin's lymphoma
Mantle cell lymphoma
Mucosa-associated lymphoid tissue (MALT) lymphoma
Childhood acute lymphoblastic leukemia
Adult T-cell leukemia
Acute lymphoblastic leukemia
Chronic myelogenous leukemia
Immunoblastic lymphoma
Kaposi's sarcoma
Cowden's syndrome (intestinal polyposis, thyroid cancer, breast cancer)
Breast cancers
Breast carcinoma
Colon carcinoma
Prostate carcinoma
Ovarian carcinoma
Endometrial cancers
Non-small cell lung carcinoma
Metastatic prostate cancers
Metastatic melanoma
Pancreatic carcinoma
Thyroid carcinoma
Bladder carcinoma
Renal cell carcinoma
Squamous cell carcinoma
Nasopharyngeal carcinoma
Glioblastoma
Hepatocellular carcinoma (HCC)
Head-and-neck cancer
Colon cancer
Colitis-associated cancer |

TABLE 2-continued

Disease indications applicable for c-Rel specific therapies

| Generic Disease | Specific disease indications benefited from c-Rel inhibition |
|---|---|
| | Gastrointestinal cancer |
| | Lung cancer |
| | Pancreatic cancer |
| | Bladder cancer |
| | Esophageal cancer |
| | Skin cancer |
| Other: | AIDS |
| | Diabetes mellitus, |
| | Cardiovascular diseases |
| | Atherosclerosis |
| | Viral diseases |
| | Osteoporosis |
| | Bone loss |
| | Neurodegenerative disorders |
| | Ataxia telangiectasis |
| | Type 1 diabetes |
| | Type 2 diabetes |
| | Metabolic diseases |
| | Aging |

The c-Rel inhibiting compound or pharmaceutical composition thereof of the present invention may be administered in a number of ways depending upon whether local or systemic treatment is desired and upon the area to be treated. Administration may be enteral (i.e., oral), topical (i.e., on the skin, including ophthalmic and to mucous membranes, including vaginal and rectal delivery), pulmonary (e.g., by inhalation or insufflation of powders or aerosols, including by nebulizer; intratracheal, intranasal, epidermal and transdermal), parenteral (i.e., by infusion through the skin), or by injection (e.g., intravenously or intramuscularly). Parenteral administration includes intravenous, intraarterial, subcutaneous, intraperitoneal or intramuscular injection or infusion; or intracranial, e.g., intrathecal or intraventricular, administration. For oral administration, liquid or solid oral formulations can be given. These include, for example, tablets, capsules, pills, troches, elixirs, suspensions, and syrups.

Dosing is dependent on the severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. The administering physician can easily determine optimum dosages, dosing methodologies and repetition rates.

The c-Rel inhibiting compound is administered in a pharmaceutically effective (i.e., treatment-effective) amount, which is an amount suitable for effecting an observable favorable change in the course of the disease or condition, or an amount that mitigates or prevents a progression of the disease or condition. Optimum dosages may vary depending on the relative potency of individual compounds, and can generally be estimated based on $EC_{50}$ or $IC_{50}$ values found to be effective in in vitro and in vivo animal models or based on the examples described herein. In general, dosage is from 0.01 µg to 100 g per kg of body weight, and may be given once or more daily, weekly, monthly, or yearly. In different embodiments, the c-Rel inhibiting compound is administered at a dosage of precisely, about, at least, above, up to, or less than, for example, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 600 mg, 700 mg, 800 mg, 900 mg, 1000 mg, 1200 mg, or 1500 mg per administration, wherein the compound can be administered by any suitable schedule, e.g., once daily, once weekly, twice daily, or twice weekly. The c-Rel inhibiting compound can also be administered in a way which releases the compound into the subject in a controlled manner over time (i.e., as a controlled release formulation), by means well known in the art, such as by use of a time release capsule or time-releasing (e.g., slow dissolving) physical form of the compound. The treating physician can estimate repetition rates for dosing based on measured residence times and concentrations of the drug in bodily fluids or tissues. Following successful treatment, it may be desirable to have the subject undergo maintenance therapy to prevent the recurrence of the disease state, wherein the therapy is administered in maintenance doses, ranging from 0.01 µg to 100 g per kg of body weight, once or more daily, for a suitable time period.

The c-Rel inhibiting compound can be co-administered with one or more other therapeutic agents outside the scope of Formulas (1) and (2), including those that target c-Rel or associated proteins outside the scope of Formulas (1) and (2). In particular, various classes of antineoplastic (e.g., anticancer) agents are contemplated for use in certain embodiments of the present invention. Anticancer agents suitable for use with the present invention include, but are not limited to, agents that induce apoptosis, agents that inhibit adenosine deaminase function, inhibit pyrimidine biosynthesis, inhibit purine ring biosynthesis, inhibit nucleotide interconversions, inhibit ribonucleotide reductase, inhibit thymidine monophosphate (TMP) synthesis, inhibit dihydrofolate reduction, inhibit DNA synthesis, form adducts with DNA, damage DNA, inhibit DNA repair, intercalate with DNA, deaminate asparagines, inhibit RNA synthesis, inhibit protein synthesis or stability, inhibit microtubule synthesis or function, inhibit protein kinase activity, block receptors for growth factors, cytokines, activating ligands, and the like.

In some embodiments, exemplary anticancer agents suitable for use in compositions and methods of the present invention include, but are not limited to: 1) alkaloids, including microtubule inhibitors (e.g., vincristine, vinblastine, and vindesine, etc.), microtubule stabilizers (e.g., paclitaxel (TAXOL®), and docetaxel, etc.), and chromatin function inhibitors, including topoisomerase inhibitors, such as epipodophyllotoxins (e.g., etoposide (VP-16), and teniposide (VM-26), etc.), and agents that target topoisomerase I (e.g., camptothecin and isirinotecan (CPT-11), etc.); 2) covalent DNA-binding agents (alkylating agents), including nitrogen mustards (e.g., mechlorethamine, chlorambucil, cyclophosphamide, ifosfamide, and busulfan (MYLERAN®), etc.), nitrosoureas (e.g., carmustine, lomustine, and semustine, etc.), and other alkylating agents (e.g., dacarbazine, hydroxymethylmelamine, thiotepa, and mitomycin, etc.); 3) noncovalent DNA-binding agents (antitumor antibiotics), including nucleic acid inhibitors (e.g., dactinomycin (actinomycin D), etc.), anthracyclines (e.g., daunorubicin (daunomycin, and cerubidine), doxorubicin (adriamycin), and idarubicin (idamycin), etc.), anthracenediones (e.g., anthracycline analogues, such as mitoxantrone, etc.), bleomycins (BLENOXANE®), etc., and plicamycin (mithramycin), etc.; 4) antimetabolites, including antifolates (e.g., methotrexate, FOLEX®, and MEXATE®, etc.), purine antimetabolites (e.g., 6-mercaptopurine (6-MP, PURINETHOL®), 6-thioguanine (6-TG), azathioprine, acyclovir, ganciclovir, chlorodeoxyadenosine, 2-chlorodeoxyadenosine (CdA), and 2'-deoxycoformycin (pentostatin), etc.), pyrimidine antagonists (e.g., fluoropyrimidines (e.g., 5-fluorouracil (ADRUCIL®), 5-fluorodeoxyuridine (FdUrd)

(floxuridine)) etc.), and cytosine arabinosides (e.g., CYTOSAR® (ara-C) and fludarabine, etc.); 5) enzymes, including L-asparaginase, and hydroxyurea, etc.; 6) hormones, including glucocorticoids, antiestrogens (e.g., tamoxifen, etc.), nonsteroidal antiandrogens (e.g., flutamide, etc.), nonsteroidal anti-estrogens (e.g. tamoxifen), and aromatase inhibitors (e.g., anastrozole (ARIMIDEX®), etc.); 7) platinum compounds (e.g., cisplatin and carboplatin, etc.); 8) monoclonal antibodies conjugated with anticancer drugs, toxins, and/or radionuclides, (e.g. Erbitux®, Rituxin®, Avastin® etc.); 9) biological response modifiers (e.g., interferons (e.g., IFN-α, etc.) and interleukins (e.g., IL-2, etc.), etc.); 10) adoptive immunotherapy; 11) hematopoietic growth factors; 12) agents that induce tumor cell differentiation (e.g., all-trans-retinoic acid, etc.); 13) gene therapy techniques; 14) antisense therapy techniques; 15) tumor vaccines; 16) therapies directed against tumor metastases (e.g., batimastat, etc.); 17) angiogenesis inhibitors; 18) proteosome inhibitors (e.g., VELCADE®); 19) inhibitors of acetylation and/or methylation (e.g., HDAC inhibitors); 20) modulators of NF kappa B; 21) inhibitors of cell cycle regulation (e.g., CDK inhibitors); 22) modulators of p53 protein function; 23) inhibitors of protein kinases (e.g. Gleevec), and 23) radiation.

Any oncolytic agent that is routinely used in a cancer therapy context may find use in the compositions and methods of the present invention. For example, the U.S. Food and Drug Administration maintains a formulary of oncolytic agents approved for use in the United States. International counterpart agencies to the U.S.F.D.A. maintain similar formularies. Table 3 below provides a list of exemplary antineoplastic agents approved for use in the U.S. Those skilled in the art will appreciate that the "product labels" required on all U.S. approved chemotherapeutics describe approved indications, dosing information, toxicity data, and the like, for the exemplary agents.

TABLE 3

List of exemplary antineoplastic agents

| | | |
|---|---|---|
| Aldesleukin (des-alanyl-1, serine-125 human interleukin-2) | Proleukin | Chiron Corp., Emeryville, CA |
| Alemtuzumab (IgG1κ anti CD52 antibody) | Campath | Millennium and ILEX Partners, LP, Cambridge, MA |
| Alitretinoin (9-cis-retinoic acid) | Panretin | Ligand Pharmaceuticals, Inc., San Diego CA |
| Allopurinol (1,5-dihydro-4 H-pyrazolo[3,4-d]pyrimidin-4-one monosodium salt) | Zyloprim | GlaxoSmithKline, Research Triangle Park, NC |
| Altretamine (N,N,N',N',N",N",-hexamethyl-1,3,5-triazine-2,4,6-triamine) | Hexalen | US Bioscience, West Conshohocken, PA |
| Amifostine (ethanethiol, 2-[(3-aminopropyl)amino]-, dihydrogen phosphate (ester)) | Ethyol | US Bioscience |
| Anastrozole (1,3-Benzenediacetonitrile, a,a,a',a'-tetramethyl-5-(1H-1,2,4-triazol-1-ylmethyl)) | Arimidex | AstraZeneca Pharmaceuticals, LP, Wilmington, DE |
| Arsenic trioxide | Trisenox | Cell Therapeutic, Inc., Seattle, WA |
| Asparaginase (L-asparagine amidohydrolase, type EC-2) | Elspar | Merck & Co., Inc., Whitehouse Station, NJ |
| BCG Live (lyophilized preparation of an attenuated strain of *Mycobacterium bovis* (*Bacillus* Calmette-Gukin [BCG], substrain Montreal) | TICE BCG | Organon Teknika, Corp., Durham, NC |
| bexarotene capsules (4-[1-(5,6,7,8-tetrahydro-3,5,5,8,8-pentamethyl-2-napthalenyl) ethenyl] benzoic acid) | Targretin | Ligand Pharmaceuticals |
| bexarotene gel | Targretin | Ligand Pharmaceuticals |
| Bleomycin (cytotoxic glycopeptide antibiotics produced by *Streptomyces verticillus*; bleomycin A$_2$ and bleomycin B$_2$) | Blenoxane | Bristol-Myers Squibb Co., NY, NY |
| Capecitabine (5'-deoxy-5-fluoro-N-[(pentyloxy)carbonyl]-cytidine) | Xeloda | Roche |
| Carboplatin (platinum, diammine [1,1-cyclobutanedicarboxylato(2-)-0,0']-,(SP-4-2)) | Paraplatin | Bristol-Myers Squibb |
| Carmustine (1,3-bis(2-chloroethyl)-1-nitrosourea) | BCNU, BiCNU | Bristol-Myers Squibb |
| Carmustine with Polifeprosan 20 Implant | Gliadel Wafer | Guilford Pharmaceuticals, Inc., Baltimore, MD |
| Celecoxib (as 4-[5-(4-methylphenyl)-3-(trifluoromethyl)-1H-pyrazol-1-yl] benzenesulfonamide) | Celebrex | Searle Pharmaceuticals, England |
| Chlorambucil (4-[bis(2chlorethyl)amino]benzenebutanoic acid) | Leukeran | GlaxoSmithKline |

TABLE 3-continued

| List of exemplary antineoplastic agents | | |
|---|---|---|
| Cisplatin ($PtCl_2H_6N_2$) | Platinol | Bristol-Myers Squibb |
| Cladribine (2-chloro-2'-deoxy-b-D-adenosine) | Leustatin, 2-CdA | R. W. Johnson Pharmaceutical Research Institute, Raritan, NJ |
| Cyclophosphamide (2-[bis(2-chloroethyl)amino] tetrahydro-2H-13,2-oxazaphosphorine 2-oxide monohydrate) | Cytoxan, Neosar | Bristol-Myers Squibb |
| Cytarabine (1-b-D-Arabinofuranosylcytosine, $C_9H_{13}N_3O_5$) | Cytosar-U | Pharmacia & Upjohn Company |
| cytarabine liposomal | DepoCyt | Skye Pharmaceuticals, Inc., San Diego, CA |
| Dacarbazine (5-(3,3-dimethyl-1-triazeno)-imidazole-4-carboxamide (DTIC)) | DTIC-Dome | Bayer AG, Leverkusen, Germany |
| Dactinomycin, actinomycin D (actinomycin produced by *Streptomyces parvullus*, $C_{62}H_{86}N_{12}O_{16}$) | Cosmegen | Merck |
| Darbepoetin alfa (recombinant peptide) | Aranesp | Amgen, Inc., Thousand Oaks, CA |
| daunorubicin liposomal ((8S-cis)-8-acetyl-10-[(3-amino-2,3,6-trideoxy-á-L-lyxo-hexopyranosyl)oxy]-7,8,9,10-tetrahydro-6,8,11-trihydroxy-1-methoxy-5,12-naphthacenedione hydrochloride) | DanuoXome | Nexstar Pharmaceuticals, Inc., Boulder, CO |
| Daunorubicin HCl, daunomycin ((1 S,3 S)-3-Acetyl-1,2,3,4,6,11-hexahydro-3,5,12-trihydroxy-10-methoxy-6,11-dioxo-1-naphthacenyl 3-amino-2,3,6-trideoxy-(alpha)-L-lyxo-hexopyranoside hydrochloride) | Cerubidine | Wyeth Ayerst, Madison, NJ |
| Denileukin diftitox (recombinant peptide) | Ontak | Seragen, Inc., Hopkinton, MA |
| Dexrazoxane ((S)-4,4'-(1-methyl-1,2-ethanediyl)bis-2,6-piperazinedione) | Zinecard | Pharmacia & Upjohn Company |
| Docetaxel ((2R,3S)-N-carboxy-3-phenylisoserine, N-tert-butyl ester, 13-ester with 5b-20-epoxy-12a,4,7b,10b,13a-hexahydroxytax-11-en-9-one 4-acetate 2-benzoate, trihydrate) | Taxotere | Aventis Pharmaceuticals, Inc., Bridgewater, NJ |
| Doxorubicin HCl (8S,10S)-10-[(3-amino-2,3,6-trideoxy-a-L-lyxo-hexopyranosyl)oxy]-8-glycolyl-7,8,9,10-tetrahydro-6,8,11-trihydroxy-1-methoxy-5,12-naphthacenedione hydrochloride) | Adriamycin, Rubex | Pharmacia & Upjohn Company |
| doxorubicin | Adriamycin PFS Intravenous injection | Pharmacia & Upjohn Company |
| doxorubicin liposomal | Doxil | Sequus Pharmaceuticals, Inc., Menlo park, CA |
| dromostanolone propionate (17b-Hydroxy-2a-methyl-5a-androstan-3-one propionate) | Dromostanolone | Eli Lilly & Company, Indianapolis, IN |
| dromostanolone propionate | Masterone injection | Syntex, Corp., Palo Alto, CA |
| Elliott's B Solution | Elliott's B Solution | Orphan Medical, Inc |
| Epirubicin ((8S-cis)-10-[(3-amino-2,3,6-trideoxy-a-L-arabino-hexopyranosyl)oxy]-7,8,9,10-tetrahydro-6,8,11-trihydroxy-8-(hydroxyacetyl)-1-methoxy-5,12-naphthacenedione hydrochloride) | Ellence | Pharmacia & Upjohn Company |
| Epoetin alfa (recombinant peptide) | Epogen | Amgen, Inc |
| Estramustine (estra-1,3,5(10)-triene-3,17-diol(17(beta))-, 3-[bis(2-chloroethyl)carbamate] 17-(dihydrogen phosphate), disodium salt, monohydrate, or estradiol 3-[bis(2-chloroethyl)carbamate] 17-(dihydrogen phosphate), disodium salt, monohydrate) | Emcyt | Pharmacia & Upjohn Company |
| Etoposide phosphate (4'-Demethylepipodophyllotoxin 9-[4,6-O-(R)-ethylidene-(beta)-D-glucopyranoside], 4'-(dihydrogen phosphate)) | Etopophos | Bristol-Myers Squibb |

TABLE 3-continued

List of exemplary antineoplastic agents

| | | |
|---|---|---|
| etoposide, VP-16 (4'-demethylepipodophyllotoxin 9-[4,6-0-(R)-ethylidene-(beta)-D-glucopyranoside]) | Vepesid | Bristol-Myers Squibb |
| Exemestane (6-methylenandrosta-1,4-diene-3,17-dione) | Aromasin | Pharmacia & Upjohn Company |
| Filgrastim (r-metHuG-CSF) | Neupogen | Amgen, Inc |
| floxuridine (intraarterial) (2'-deoxy-5-fluorouridine) | FUDR | Roche |
| Fludarabine (fluorinated nucleotide analog of the antiviral agent vidarabine, 9-b-D-arabinofuranosyladenine (ara-A)) | Fludara | Berlex Laboratories, Inc., Cedar Knolls, NJ |
| Fluorouracil, 5-FU (5-fluoro-2,4(1H,3H)-pyrimidinedione) | Adrucil | ICN Pharmaceuticals, Inc., Humacao, Puerto Rico |
| Fulvestrant (7-alpha-[9-(4,4,5,5,5-penta fluoropentylsulphinyl) nonyl]estra-1,3,5-(10)-triene-3,17-beta-diol) | Faslodex | IPR Pharmaceuticals, Guayama, Puerto Rico |
| Gemcitabine (2'-deoxy-2',2'-difluorocytidine monohydrochloride (b-isomer)) | Gemzar | Eli Lilly |
| Gemtuzumab Ozogamicin (anti-CD33 hP67.6) | Mylotarg | Wyeth Ayerst |
| Goserelin acetate (acetate salt of [D-Ser(But)$^6$,Azgly$^{10}$]LHRH; pyro-Glu-His-Trp-Ser-Tyr-D-Ser(But)-Leu-Arg-Pro-Azgly-NH2 acetate [$C_{59}H_{84}N_{18}O_{14}$ ($C_2H_4O_2$)$_x$ | Zoladex Implant | AstraZeneca Pharmaceuticals |
| Hydroxyurea | Hydrea | Bristol-Myers Squibb |
| Ibritumomab Tiuxetan (immunoconjugate resulting from a thiourea covalent bond between the monoclonal antibody Ibritumomab and the linker-chelator tiuxetan [N-[2-bis(carboxymethyl)amino]-3-(p-isothiocyanatophenyl)-propyl]-[N-[2-bis(carboxymethyl)amino]-2-(methyl)-ethyl]glycine) | Zevalin | Biogen IDEC, Inc., Cambridge MA |
| Idarubicin (5,12-Naphthacenedione, 9-acetyl-7-[(3-amino-2,3,6-trideoxy-(alpha)-L-lyxo-hexopyranosyl)oxy]-7,8,9,10-tetrahydro-6,9,11-trihydroxyhydrochloride, (7S-cis)) | Idamycin | Pharmacia & Upjohn Company |
| Ifosfamide (3-(2-chloroethyl)-2-[(2-chloroethyl)amino]tetrahydro-2H-1,3,2-oxazaphosphorine 2-oxide) | IFEX | Bristol-Myers Squibb |
| Imatinib Mesilate (4-[(4-Methyl-1-piperazinyl)methyl]-N-[4-methyl-3-[[4-(3-pyridinyl)-2-pyrimidinyl]amino]-phenyl]benzamide methanesulfonate) | Gleevec | Novartis AG, Basel, Switzerland |
| Interferon alfa-2a (recombinant peptide) | Roferon-A | Hoffmann-La Roche, Inc., Nutley, NJ |
| Interferon alfa-2b (recombinant peptide) | Intron A (Lyophilized Betaseron) | Schering AG, Berlin, Germany |
| Irinotecan HCl ((4S)-4,11-diethyl-4-hydroxy-9-[(4-piperi-dinopiperidino)carbonyloxy]-1H-pyrano[3',4':6,7] indolizino[1,2-b] quinoline-3,14(4H,12H) dione hydrochloride trihydrate) | Camptosar | Pharmacia & Upjohn Company |
| Letrozole (4,4'-(1H-1,2,4-Triazol-1-ylmethylene) dibenzonitrile) | Femara | Novartis |
| Leucovorin (L-Glutamic acid, N[4[[(2amino-5-formyl1,4,5,6,7,8 hexahydro4oxo6-pteridinyl)methyl]amino]benzoyl], calcium salt (1:1)) | Wellcovorin, Leucovorin | Immunex, Corp., Seattle, WA |
| Levamisole HCl ((−)-(S)-2,3,5,6-tetrahydro-6-phenylimidazo [2,1-b] thiazole monohydrochloride $C_{11}H_{12}N_2S \cdot HCl$) | Ergamisol | Janssen Research Foundation, Titusville, NJ |
| Lomustine (1-(2-chloro-ethyl)-3-cyclohexyl-1-nitrosourea) | CeeNU | Bristol-Myers Squibb |
| Meclorethamine, nitrogen mustard (2-chloro-N-(2-chloroethyl)-N-methylethanamine hydrochloride) | Mustargen | Merck |

TABLE 3-continued

List of exemplary antineoplastic agents

| | | |
|---|---|---|
| Megestrol acetate<br>17α(acetyloxy)-6-methylpregna-4,6-diene-<br>3,20-dione | Megace | Bristol-Myers Squibb |
| Melphalan, L-PAM<br>(4-[bis(2-chloroethyl) amino]-L-phenylalanine) | Alkeran | GlaxoSmithKline |
| Mercaptopurine, 6-MP<br>(1,7-dihydro-6 H-purine-6-thione monohydrate) | Purinethol | GlaxoSmithKline |
| Mesna<br>(sodium 2-mercaptoethane sulfonate) | Mesnex | Asta Medica |
| Methotrexate<br>(N-[4-[[(2,4-diamino-6-<br>pteridinyl)methyl]methylamino]benzoyl]-L-<br>glutamic acid) | Methotrexate | Lederle Laboratories |
| Methoxsalen<br>(9-methoxy-7H-furo[3,2-g][1]-benzopyran-7-one) | Uvadex | Therakos, Inc., Way<br>Exton, Pa |
| Mitomycin C<br>mitomycin C | Mutamycin<br>Mitozytrex | Bristol-Myers Squibb<br>SuperGen, Inc.,<br>Dublin, CA |
| Mitotane<br>(1,1-dichloro-2-(o-chlorophenyl)-2-(p-<br>chlorophenyl) ethane) | Lysodren | Bristol-Myers Squibb |
| Mitoxantrone<br>(1,4-dihydroxy-5,8-bis[[2-[(2-<br>hydroxyethyl)amino]ethyl]amino]-9,10-<br>anthracenedione dihydrochloride) | Novantrone | Immunex<br>Corporation |
| Nandrolone phenpropionate | Durabolin-50 | Organon, Inc., West<br>Orange, NJ |
| Nofetumomab | Verluma | Boehringer Ingelheim<br>Pharma KG,<br>Germany |
| Oprelvekin<br>(IL-11) | Neumega | Genetics Institute,<br>Inc., Alexandria, VA |
| Oxaliplatin<br>(cis-[(1R,2R)-1,2-cyclohexanediamine-N,N']<br>[oxalato(2-)-O,O'] platinum) | Eloxatin | Sanofi Synthelabo,<br>Inc., NY, NY |
| Paclitaxel<br>(5β,20-Epoxy-1,2a,4,7β,10β,13a-<br>hexahydroxytax-11-en-9-one 4,10-diacetate 2-<br>benzoate 13-ester with (2R,3 S)-N-benzoyl-3-<br>phenylisoserine) | TAXOL | Bristol-Myers Squibb |
| Pamidronate<br>(phosphonic acid (3-amino-1-hydroxypropylidene)<br>bis-, disodium salt, pentahydrate, (APD)) | Aredia | Novartis |
| Pegademase<br>((monomethoxypolyethylene glycol succinimidyl)<br>11-17-adenosine deaminase) | Adagen<br>(Pegademase<br>Bovine) | Enzon<br>Pharmaceuticals, Inc.,<br>Bridgewater, NJ |
| Pegaspargase<br>(monomethoxypolyethylene glycol succinimidyl<br>L-asparaginase) | Oncaspar | Enzon |
| Pegfilgrastim<br>(covalent conjugate of recombinant methionyl<br>human G-CSF (Filgrastim) and<br>monomethoxypolyethylene glycol) | Neulasta | Amgen, Inc |
| Pentostatin | Nipent | Parke-Davis<br>Pharmaceutical Co.,<br>Rockville, MD |
| Pipobroman | Vercyte | Abbott Laboratories,<br>Abbott Park, IL |
| Plicamycin, Mithramycin<br>(antibiotic produced by *Streptomyces plicatus*) | Mithracin | Pfizer, Inc., NY, NY |
| Porfimer sodium | Photofrin | QLT<br>Phototherapeutics,<br>Inc., Vancouver,<br>Canada |
| Procarbazine<br>(N-isopropyl-μ-(2-methylhydrazino)-p-toluamide<br>monohydrochloride) | Matulane | Sigma Tau<br>Pharmaceuticals, Inc.,<br>Gaithersburg, MD |
| Quinacrine<br>(6-chloro-9-(1-methyl-4-diethyl-amine)<br>butylamino-2-methoxyacridine) | Atabrine | Abbott Labs |
| Rasburicase<br>(recombinant peptide) | Elitek | Sanofi-Synthelabo,<br>Inc., |
| Rituximab<br>(recombinant anti-CD20 antibody) | Rituxan | Genentech, Inc.,<br>South San Francisco,<br>CA |
| Sargramostim<br>(recombinant peptide) | Prokine | Immunex Corp |

TABLE 3-continued

List of exemplary antineoplastic agents

| | | |
|---|---|---|
| Streptozocin (streptozocin 2-deoxy-2-[[(methylnitrosoamino)carbonyl]amino]-a(and b)-D-glucopyranose and 220 mg citric acid anhydrous) | Zanosar | Pharmacia & Upjohn Company |
| Talc ($Mg_3Si_4O_{10}$ $(OH)_2$) | Sclerosol | Bryan, Corp., Woburn, MA |
| Tamoxifen ((Z)2-[4-(1,2-diphenyl-1-butenyl) phenoxy]-N,N-dimethylethanamine 2-hydroxy-1,2,3-propanetricarboxylate (1:1)) | Nolvadex | AstraZeneca Pharmaceuticals |
| Temozolomide (3,4-dihydro-3-methyl-4-oxoimidazo[5,1-d]-as-tetrazine-8-carboxamide) | Temodar | Schering |
| teniposide, VM-26 (4'-demethylepipodophyllotoxin 9-[4,6-0-(R)-2-thenylidene-(beta)-D-glucopyranoside]) | Vumon | Bristol-Myers Squibb |
| Testolactone (13-hydroxy-3-oxo-13,17-secoandrosta-1,4-dien-17-oic acid [dgr]-lactone) | Teslac | Bristol-Myers Squibb |
| Thioguanine, 6-TG (2-amino-1,7-dihydro-6 H-purine-6-thione) | Thioguanine | GlaxoSmithKline |
| Thiotepa (Aziridine, 1,1',1''-phosphinothioylidynetris-, or Tris (1-aziridinyl) phosphine sulfide) | Thioplex | Immunex Corporation |
| Topotecan HCl ((S)-10-[(dimethylamino) methyl]-4-ethyl-4,9-dihydroxy-1H-pyrano[3',4':6,7] indolizino [1,2-b] quinoline-3,14-(4H,12H)-dione monohydrochloride) | Hycamtin | GlaxoSmithKline |
| Toremifene (2-(p-[(Z)-4-chloro-1,2-diphenyl-1-butenyl]-phenoxy)-N,N-dimethylethylamine citrate (1:1)) | Fareston | Roberts Pharmaceutical Corp., Eatontown, NJ |
| Tositumomab, I 131 Tositumomab (recombinant murine immunotherapeutic monoclonal $IgG_{2a}$ lambda anti-CD20 antibody (I 131 is a radioimmunotherapeutic antibody)) | Bexxar | Corixa Corp., Seattle, WA |
| Trastuzumab (recombinant monoclonal $IgG_1$ kappa anti-HER2 antibody) | Herceptin | Genentech, Inc |
| Tretinoin, ATRA (all-trans retinoic acid) | Vesanoid | Roche |
| Uracil Mustard | Uracil Mustard Capsules | Roberts Labs |
| Valrubicin, N-trifluoroacetyladriamycin-14-valerate ((2S-cis)-2-[1,2,3,4,6,11-hexahydro-2,5,12-trihydroxy-7 methoxy-6,11-dioxo-[[4 2,3,6-trideoxy-3-[(trifluoroacetyl)-amino-α-L-lyxo-hexopyranosyl]oxy]-2-naphthacenyl]-2-oxoethyl pentanoate) | Valstar | Anthra Medeva |
| Vinblastine, Leurocristine ($C_{46}H_{56}O_{10} \cdot H_2SO_4$) | Velban | Eli Lilly |
| Vincristine ($C_{46}H_{56}N_4O_{10} \cdot H_2SO_4$) | Oncovin | Eli Lilly |
| Vinorelbine (3',4'-didehydro-4'-deoxy-C'-norvincaleukoblastine [R-(R*,R*)-2,3-dihydroxybutanedioate (1:2)(salt)]) | Navelbine | GlaxoSmithKline |
| Zoledronate, Zoledronic acid ((1-Hydroxy-2-imidazol-1-yl-phosphonoethyl) phosphonic acid monohydrate) | Zometa | Novartis |

In other embodiments, other agents (e.g., immunomodulatory agents, anti-inflammatory agents, NSAID, and immunotherapeutics) are co-administered with a c-Rel inhibiting composition of the present invention. Useful non-steroidal anti-inflammatory agents, include, but are not limited to, aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmefin, zomepirac, fiopinac, zidometacin, acemetacin, fentiazac, clidanac, oxpinac, mefenamio acid, meclofenamic acid, flufenamic acid, niflumic acid, tolfenamic acid, diflurisal, flufenisal, piroxicam, sudoxicam, isoxicam; salicylic acid derivatives, including aspirin, sodium salicylate, choline magnesium trisalicylate, salsalate, diflunisal, salicylsalicylic acid, sulfasalazine, and olsalazin; para-aminophennol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid, and meclofenamic acid; enolic acids, including oxicams (piroxicam, tenoxicam), and pyrazolidinediones (phenylbutazone, oxyphenthartazone); and alkanones, including nabumetone and pharmaceufioally acceptable salts thereof and mixtures thereof. For a more detailed description of the NSAIDs, reference is made to Paul A. Insel, Analgesic-Antipyretic and Anti-inflammatory Agents and Drugs Employed in the Treatment of Gout, in Goodman & Gilman's The Pharmacological Basis of Therapeutics 617-57 (Perry B. Molinhoff and Raymond W. Ruddon eds., 9th ed 1996) and Glen R. Hanson, Analgesic, Antipyretic and Anti-Inflammatory Drugs in Remington: The Science and Practice of Pharmacy Vol II 1196-1221 (A. R. Gennaro ed. 19th ed. 1995), the contents of which are hereby incorporated by reference in their entireties.

Other examples of prophylactic and therapeutic agents include, but are not limited to, immunomodulatory agents, anti-inflammatory agents (e.g., adrenocorticoids, corticosteroids (e.g., beclomethasone, budesonide, flunisolide, fluticasone, triamcinolone, methlyprednisolone, prednisolone, prednisone, hydroeortisone), glucocorticoids, steroids, non-steriodal anti-inflammatory drugs (e.g., aspirin, ibuprofen, diclofenac, and COX-2 inhibitors), and leukotreine antagonists (e.g., montelukast, methyl xanthines, zafirlukast, and zileuton), beta2-agonists (e.g., albuterol, biterol, fenoterol, isoetharie, metaproterenol, pirbuterol, salbutamol, terbutalin formoterol, salmeterol, and salbutamol terbutaline), anticholinergic agents (e.g., ipratropium bromide and oxitropium bromide), sulphasalazine, penicillamine, dapsone, antihistamines, anti-malarial agents (e.g., hydroxychloroquine), antiviral agents, and antibiotics (e.g., dactinomycin (formerly actinomycin), bleomyein, erythomycin, penicillin, mithramycin, and anthramycin (AMC)).

Any immunomodulatory agent well-known to one of skill in the art may or may not also be used for co-administration with c-Rel inhibiting compositions of the invention. Immunomodulatory agents can affect one or more or all aspects of the immune response in a subject. Aspects of the immune response include, but are not limited to, the inflammatory response, the complement cascade, leukocyte and lymphocyte differentiation, proliferation, and/or effector function, monocyte and/or basophil counts, and the cellular communication among cells of the immune system. In certain embodiments, an immunomodulatory agent modulates one aspect of the immune response. In other embodiments, an immunomodulatory agent modulates more than one aspect of the immune response. In a particular embodiment, the administration of an immunomodulatory agent to a subject inhibits or reduces one or more aspects of the subject's immune response capabilities. In a specific embodiment of the invention, the immunomodulatory agent inhibits or suppresses the immune response in a subject.

Some examples of immunomodulatory agents include, but are not limited to, proteinaceous agents such as cytokines, cytokine blockers (e g inhibitory agents of TNF, IL1, IL-2, IL6, IL17, IL23), peptide mimetics, and antibodies (e.g., human, humanized, chimeric, monoclonal, polyclonal, Fvs, ScFvs, Fab or F(ab)$_2$ fragments or epitope binding fragments), nucleic acid molecules (e.g., antisense nucleic acid molecules and triple helices), small molecules, organic compounds, inorganic compounds, auto-antigens, allergens, allo-antigens, and pathogenic antigens. In particular, immunomodulatory agents include, but are not limited to, methotrexate, leflunomide, cyclophosphamide, cytoxan, Immuran, cyclosporine A, minocycline, azathioprine, antibiotics (e.g., FK506 (tacrolimus)), methylprednisolone (MP), corticosteroids, steroids, mycophenolate mofetil, rapamycin (sirolimus), mizoribine, deoxyspergualin, brequinar, malononitriloaminodes (e.g., leflunamide), T cell receptor modulators, B cell receptor modulators, antigen presenting cell modulators, cytokine receptor modulators, antigens, and mast cell modulators.

Some examples of T cell receptor modulators include, but are not limited to, anti-T cell receptor antibodies (e.g., anti-CD4 antibodies (e.g., cM-T412 (Boeringer), IDEC-CE9.1 (IDEC and SKB), mAB 4162W94, Orthoclone and OKTcdr4a (Janssen-Cilag)), anti-CD3 antibodies (e.g., Nuvion (Product Design Labs), OKT3 (Johnson & Johnson), or Rituxan (IDEC)), anti-CD5 antibodies (e.g., an anfi-CD5 ricin-linked immunoconjugate), anti-CD7 antibodies (e.g., CHH-380 (Novartis)), anti-CD8 antibodies, anti-CD40 ligand monoclonal antibodies (e.g., IDEC-131 (IDEC)), anti-CD52 antibodies (e.g., CAMPATH 1H (Ilex)), anti-CD2 antibodies (e.g., MEDI-507 (MedImmune, Inc., International Publication Nos.WO 02/098370 and WO 02/069904), anti-CD1a antibodies (e.g., Xanelim (Genentech)), and anti-B7 antibodies (e.g., IDEC-114)(IDEC)), CTLA4-immunoglobulin, LFA-3TIP (Biogen, International Publication No. WO 93/08656 and U.S. Pat. No. 6,162,432), anti-CD28, anti-PD1, anti-BTLA, C-type lectin antibodies, cytokines (e.g. IL2, IFN-γ, GM-CSF, TNF, IL15, IL7, IL17).

Some examples of B cell modulators include, but are not limited to, anti-IgM, anti-IgG, anti-IgD, anti-IgA, anti-IgE, anti-CD20, anti-CD20, anti-CD19, anti-CD21, anti-CD23, anti-CD30, anti-TLR9, anti-Fas, anti-Blys receptor, anti-April receptor, anti-BCMA receptor, anti-Fcgamma receptor, anti-Blys (Baff), anti-April, anti-BCMA, and anti-BTLA.

Some examples of antigen presenting cell modulators include, but are not limited to, anti-CD40, anti-TLRs, antibodies to C-type lectin-ike molecules (e.g. NKRP1f, OCILRP2), cytokines (e.g. GM-CSF, TNF, IL1, IL6, IL12, IL15, IL23, IL27), and antibodies to costimularoty or co-repressor molecules (e.g. CD80, CD86, PDL1, PDL2, B7-H1, B7-H3).

Some examples of cytokine receptor modulators include, but are not limited to, soluble cytokine receptors (e.g., the extracellular domain of a TNF-α receptor or a fragment thereof, the extracellular domain of an IL-1β receptor or a fragment thereof, and the extracellular domain of an IL-6 receptor or a fragment thereof), cytokines or fragments thereof (e.g., interleukin IL-2, IL-3, IL-4, IL-5, IL-6, IL-7, IL-8, IL-9, IL-10, IL-11, IL-13, IL-15, IL-23, TNF-α, TNF-β, interferon (IFN)-α, IFN-β, IFN-7, and GM-CSF), anti-cytokine receptor antibodies (e.g., anti-IFN receptor antibodies, anti-IL-2 receptor antibodies (e.g., Zenapax (Protein Design Labs)), anti-IL-3 receptor antibodies, anti-IL-4 receptor antibodies, anti-IL-6 receptor antibodies, anti-IL-10 receptor antibodies, anti-IL-12 receptor antibodies, anti-IL-13 receptor antibodies, anti-IL-15 receptor antibodies, and anti-IL-23 receptor antibodies), and anti-cytokine antibodies (e.g. anti-TNF, anti-IL2, anti-IL6).

In one embodiment, an antigen is a self- or auto-antigen, allergen, foreign- or allo-antigen, or pathogenic antigen. Some examples of self and allo-antigens include, but not limited to, insulin, an extract or cells derived from insulin-producing beta cells, collagen, an extract or cells derived from synoviocytes, myelin basic protein (MBP), glycoproteins derived from neuronal tissues, MHC-mis-matched donor cells, tissues, and MHC extracts or complexes.

Some examples of allergens and pathogenic antigens include molecules or extracts derived from pollens, dust mite, pathogenic bacteria or viruses (e.g., *M. tuberculosis*, HCV, HIV, Herpes simplex, *Helicobacter pylori*, *Listeria monocytogenes, streptococcus*, influenza virus, bird flu virus (H5N1), SARS coronavirus, HCV, HIV, EBV, Herpes simplex, *Helicobacter pylori, Listeria*).

In one embodiment, a cytokine receptor modulator is a mast cell modulator. Some examples of mast cell modulators include, but are not limited to stem cell factor (c-kit receptor ligand) inhibitor (e.g., mAb 7H6, mAb 8H7a, pAb 1337, FK506, CsA, dexamthasone, and fluconcinonide), c-kit receptor inhibitor (e.g., STI 571 (formerly known as CGP 57148B)), mast cell protease inhibitor (e.g., GW-45, GW-58, wortmannin, LY 294002, calphostin C, cytochalasin D, gertistein, KT5926, staurosproine, and lactoferrin), relaxin ("RLX"), IgE antagonist (e.g., antibodies rhuMAb-E25 omalizumab, HMK-12 and 6HD5, and mAB Hu-901), IL-3 antagonists, IL-4 antagonists, IL-10 antagonists, and TGF-beta.

In combination therapy treatment, both a compound of this invention and another therapeutic agent are administered to a mammal (e.g., human, male or female) by conventional methods. The agents may be administered in a single dosage form or in separate dosage forms. Effective amounts of the other therapeutic agents are well known to those skilled in the art. However, it is well within the skilled artisan's purview to determine the other therapeutic agent's optimal effective-amount range. In one embodiment of the invention where another therapeutic agent is administered to an animal, the effective amount of the compound of this invention is less than its effective or optimal amount when the other therapeutic agent is not administered. In another embodiment, the effective amount of the additional therapeutic agent is less than its effective or optimal amount when a compound of this invention is not administered. In this way, undesired side effects associated with high doses of either agent may be minimized. Other potential advantages (including, without limitation improved dosing regimens and/or reduced drug cost) will be apparent to those of skill in the art.

In various embodiments, the therapies (e.g., prophylactic or therapeutic agents) are administered less than 5 minutes apart, less than 30 minutes apart, 1 hour apart, at about 1 hour apart, at about to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In particular embodiments, two or more therapies are administered within the same patent visit.

In certain embodiments, one or more compounds of the invention and one or more other therapies (e.g., prophylactic or therapeutic agents) are administered in a cyclic manner Cycling therapy involves the administration of a first therapy (e.g., a first prophylactic or therapeutic agent) for a period of time, followed by the administration of a second therapy (e.g., a second prophylactic or therapeutic agent) for a period of time, optionally followed by the administration of a third therapy (e.g., prophylactic or therapeutic agent) for a period of time and so forth, and repeating this sequential administration. A possible advantage of cyclic administration is the reduction or prevention of the development of resistance to one of the therapies, and/or to avoid or reduce the side effects of one of the therapies, and/or to improve the efficacy of the therapies.

In certain embodiments, the administration of the same compound of the invention may be repeated and the administrations may be separated by at least 1 day, 2 days, 3 days, 5 days, 10 days, 15 days, 30 days, 45 days, 2 months, 75 days, 3 months, or at least 6 months. In other embodiments, the administration of the same therapy (e.g., prophylactic or therapeutic agent) other than a compound of the invention may be repeated and the administration may be separated by at least at least day, 2 days, 3 days, 5 days, 10 days, 15 days, 30 days, 45 days, 2 months, 75 days, 3 months, or at least 6 months.

The efficacy of a compound of Formula (1) or (2) to inhibit c-Rel or to treat a disease or prevent a condition associated with overexpression of c-Rel can be measured by determining the $IC_{50}$ of the compound. As used herein, "$IC_{50}$" or "half maximal inhibitory concentration" identifies how much of a compound is needed to inhibit activity by half. The $IC_{50}$ of a compound can be determined by constructing a dose-response curve and examining the effect of different concentrations of a compound on reducing or preventing enzymatic activity. $IC_{50}$ values can be calculated for a given inhibitor by determining the concentration needed to inhibit half of the maximum enzymatic activity. The mathematical analysis used for deriving an $IC_{50}$ value is well known in the art. The c-Rel inhibiting compounds of the invention preferably inhibit c-Rel and/or a disease or condition associated with overexpression of c-Rel with an $IC_{50}$ of up to or less than 100 µM, 50 µM, 25 µM, 10 µM, 5 µM, 1 µM, 0.5 µM, 0.2 µM, 0.1 µM, 0.05 µM, 0.02 µM, or 0.01 µM or an $IC_{50}$ value within a range bounded by any two of these values.

Examples have been set forth below for the purpose of illustration and to describe the best mode of the invention at the present time. However, the scope of this invention is not to be in any way limited by the examples set forth herein.

EXAMPLES

Reagents and Instrumentation

Example 1

Biochemical Assays (Fluorescence Polarization) for Screening of Rel Inhibitors

This Example describes the identification of small molecule inhibitors of c-Rel. Rel protein functions primarily by forming a homo- or hetero-dimer and binding its cognate DNA site in the promoter region of targeted genes. Thus, small molecules that are able to efficiently disrupt the formation of the c-Rel dimer-targeted kB site complex are desirable inhibitors. These compounds may act either directly via inhibition at the protein-DNA interface or dimerizational interface, or indirectly by binding to an allosteric site and induction of a conformational change of c-Rel protein.

Historically, transcription factors have been considered difficult to access by small molecule inhibitors due to the large interaction surface mediating the binding of transcription factors to DNA. However, there is growing evidence to suggest that small molecules can modulate the interactions responsible for DNA-protein and protein-protein complex formation. Perhaps the best examples are natural compounds identified to possess anti-NF-kB activity, including epoxyquinomicin, plumbagin. Some of these natural compounds and their synthetic derivatives (e.g. DHMEQ) inhibit Rel or NF-kB via specific interaction with the Cysteine residues critical for binding to the specific kB-DNA sequence (Ouk, Liou, Liou, Future Med. Chem. 2009, 1(9), 1683-1707). For example, DHMEQ was shown to inhibit NF-kB DNA binding activity by interacting with the Cys-38 of p50 protein, Cys-62 of p65 protein, and Cys-27 of c-Rel protein.

Figure 1A:
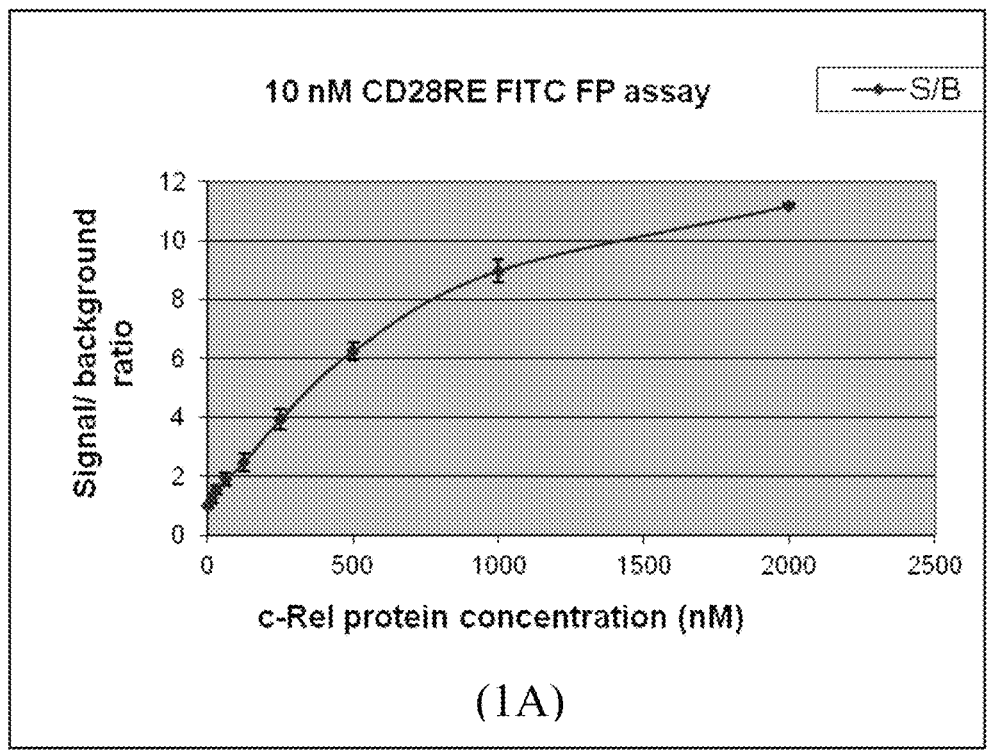
FIGS. 1A, 1B. Charts demonstrating the FP assay optimization of the fluorescent polarization assay used in some embodiments of the present invention. c-Rel(281) at 2-fold dilutions (2000 to 15.625 nM) were mixed with CD28RE-FITC (10, 3.3, 1.1, 0.33, 0.11 nM) in the FP buffer for 30 minutes. mP values were used to calculate signal/background ratio. Only the data for 10 nM and 0.33 nM are shown here.
Figure 1B:
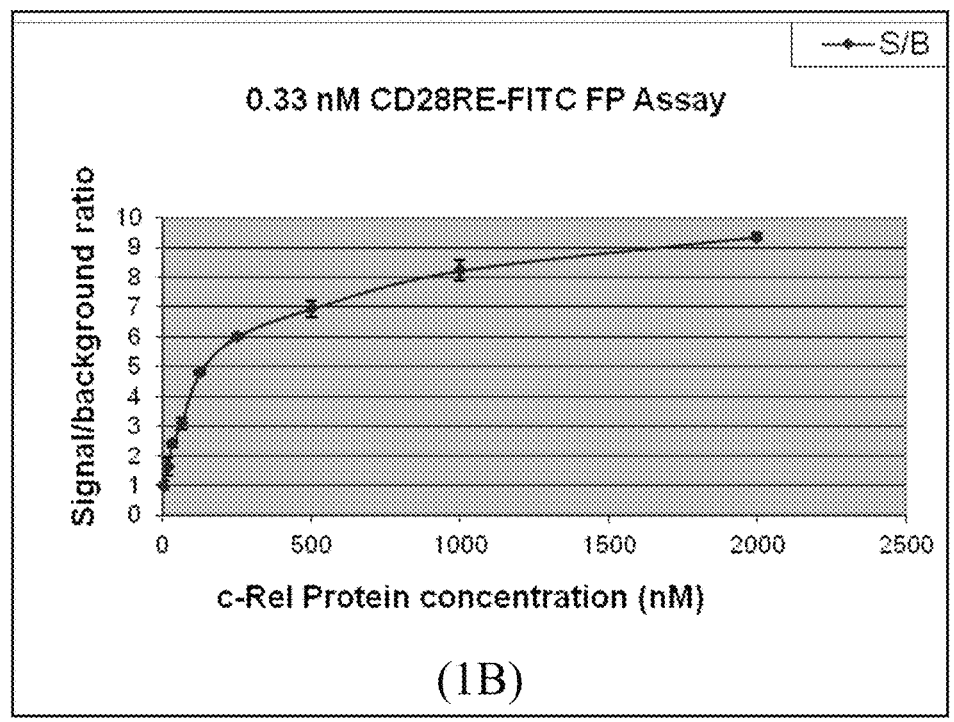

The instant disclosure is particularly directed to developing "direct" Rel inhibitors. To develop such "direct" Rel inhibitors, a fluorescence polarization (FP)-based high-throughput screening assay was utilized to identify small molecules that disrupt the binding of human c-Rel homodimer to the CD28 response element (CD28RE) in the promoter region of IL-2 gene (FIGS. 1A, 1B). As an example, a series of titration experiments were performed to optimize c-Rel protein and FITC-CD28RE probe concentrations to be used in the FP assay. The representative data for 10 nM and 0.33 nM are shown in FIGS. 1A and 1B, respectively. In both cases, the maximal Signal to Background (S/B) ratio for these titration experiments are in the range of 8-11, indicating a robust assay. The background value for DNA probe alone is ~20 mP and the signal for c-Rel-CD28RE reaction is ~200 mP.

The c-Rel/CD28RE FP assay was utilized to screen 15,000 compounds and ~100 positive hits were identified with FP signals below μ-3σ. The positive hits were further analyzed by an orthogonal assay, the electrophoretic mobility shift assay (EMSA) (see Examples 2 and 3). Some structure-activity-relationships (SARs) strategy for the c-Rel inhibiting compounds are shown in (FIG. 2A), and an exemplary synthetic method is shown in (FIG. 2B).

Example 2

Synthesis of Rel Inhibitors

Example 2-1

Synthesis of 5-(4-methoxybenzylidene)-2-thioxodihydropyrimidine-4,6(1H,5H)-dione, 1b 1.a) Synthesis of 2-thioxodihydropyrimidine-4,6(1H,5H)-dione, 1a Diethyl malonate (6.40 g, 40 mmol) was added into a solution of sodium ethoxide in ethanol (21% wt, 22.4 ml, 80 mmol). Precipitation occurred progressively. The reaction mixture was stirred for 1 hour. To the mixture was added thiourea (3.04 g, 40 mmol). The reaction mixture was heated to 80° C. for 20 hours. LCMS indicated that the reaction was completed. The reaction mixture was concentrated to obtain an off-white powder residue. 15 ml of water was added to dissolve the residue. 25 ml of acetic acid was added progressively to the mixture to cause precipitation. After the addition of acetic acid, the mixture was gently stirred for an additional 2 hours at 10° C. The solid was filtered, washed with water and dried at 40° C. in a vacuum oven to yield compound 1a, (74%, 4.26 g, 29.6 mmol).

1.b) Synthesis of 5-(4-methoxybenzylidene)-2-thioxodihydropyrimidine-4,6(1H,5H)-dione, 1b A mixture of 1a (0.072 g, 0.5 mmol) and 4-methoxybenzaldehyde (0.068 g, 0.5 mmol) in ethanol (2 ml) was heated to 80° C. and stirred for 18 hours. Ethanol was partially removed from reaction mixture by evaporation. To the residue was added water (5 ml) and ethyl acetate (3 ml). The suspension was stirred at 0° C. for 1 hour and then filtered. The solid was filtered, washed with water, washed with a mixture of hexanes:ethyl acetate, 8:2, and dried under vacuum to yield 1b, (85%, 0.111 g, 0.42 mmol).

Example 2-2

Synthesis of 5-(naphthalen-1-ylmethylene)-2-thioxodihydropyrimidine-4,6(1H,5H)-dione, 2b A mixture of 1a (0.072 g, 0.5 mmol) and 1-napthaldehyde (0.078 g, 0.5 mmol) in ethanol (2 ml) was heated to 80° C. and stirred for 18 hours. Ethanol was partially removed from reaction mixture by evaporation. To the residue was added water (5 ml) and ethyl acetate (3 ml). The suspension was stirred at 0° C. for 1 hour and then filtered. The solid was filtered, washed with water, washed with a mixture of hexanes:ethyl acetate, 8:2, and dried under vacuum to yield 2b, (72%, 0.102 g, 0.36 mmol).

Example 2-3

Synthesis of 5-(2,4-dimethoxybenzylidene)-2-thioxodihydropyrimidine-4,6(1H,5H)-dione, 3b [BA-011]

A mixture of 1a (0.072 g, 0.5 mmol) and 2,4-dimethoxybenzaldehyde (0.083 g, 0.5 mmol) in ethanol (2 ml) was heated to 80° C. and stirred for 14 hours. Ethanol was partially removed from reaction mixture by evaporation. To the residue was added water (5 ml) and ethyl acetate (3 ml). The suspension was stirred at 0° C. for 1 hour and then filtered. The solid was filtered, washed with water, washed with a mixture of hexanes:ethyl acetate, 8:2, and dried under vacuum to yield 3b, (68%, 0.099 g, 0.34 mmol).

Example 2-4

Synthesis of 5-((2-hydroxynaphthalen-1-yl)methylene)-2-thioxodihydropyrimidine-4,6(1H,5H)-dione, 2d A mixture of 1a (0.072 g, 0.5 mmol) and 2-hydroxy-1-naphthaldehyde (0.086 g, 0.5 mmol) in ethanol (2 ml) was heated to 80° C. and stirred for 14 hours. Ethanol was partially removed from reaction mixture by evaporation. To the residue was added water (5 ml) and ethyl acetate (3 ml). The suspension was stirred at 0° C. for 1 hour and then filtered. The solid was filtered, washed with water, washed with a mixture of hexanes:ethyl acetate, 8:2, and dried under vacuum to yield 4b, (73%, 0.109 g, 0.36 mmol).

Example 2-5

Synthesis of 5,5'-(1,4-phenylenebis(methan-1-yl-1-ylidene))dipyrimidine-2,4,6(1H,3H,5H)-trione, 5b [BA-002]

A mixture of barbituric acid (0.307 g, 2.4 mmol) and teraphthaldehyde (0.134 g, 1.0 mmol) in ethanol (4 ml) and acetic acid (0.5 ml) was heated to 80° C. and stirred for 20 hours. Ethanol was partially removed from reaction mixture by evaporation. To the residue was added NH$_4$Cl aqueous saturated (10 ml). The suspension was stirred at 0° C. for 1 hour and then filtered. The solid was filtered, washed with water, washed with a mixture of hexanes:ethyl acetate, 8:2, and dried under vacuum to yield 5b, (62%, 0.219 g, 0.62 mmol).

Example 2-6

5-(5-chloro-2-methoxybenzylidene)-1,3-dimethylpyrimidine-2,4,6(1H,3H,5H)-trione, 6b [BA-004]

A mixture of barbituric acid (0.128 g, 1.0 mmol) and 4-chloro-2-methoxybenzaldehyde (0.171 g, 1.0 mmol) in ethanol (4 ml) and acetic acid (0.5 ml) was heated to 80° C. and stirred for 20 hours. Ethanol was partially removed from reaction mixture by evaporation. To the residue was added $NH_4Cl$ aqueous saturated (10 ml). The suspension was stirred at 0° C. for 1 hour and then filtered. The solid was filtered, washed with water, washed with a mixture of hexanes:ethyl, acetate, 8:2, and dried under vacuum to yield 6b, (71%, 0.199 g, 0.71 mmol).

Example 2-7

Synthesis of 5-(2-(2-chlorobenzyloxyl)benzylidene)-1,3-dimethylpyrimidine-2,4,6(1H,3H,5H)-trione, 7b [BA-006]

7.a) Synthesis of 2-(2-chlorobenzyloxyl)benzaldehyde, 7a

A mixture of 2-hydroxybenzaldehyde (0.244 g, 2.0 mmol), 2-chlorobenzyl chloride (0.354 g, 2.2 mmol) and K2CO3 (0.414 g, 3.0 mmol) in 1,2-dimethoxyethane was heated to 100° C. and stirred for 4 hours. The mixture was partially concentrated by evaporation. Water (15 ml) was added to the residue. The suspension was filtered. The obtained solid was washed with water and then with hexanes and vacuum dried to yield 7a (94%, 0.463 g, 1.88 mmol).

7.b) Synthesis of 5-(2-(2-chlorobenzyloxyl)benzylidene)-1,3-dimethylpyrimidine-2,4,6(1H,3H,5H)-trione, 7b A mixture of 1,3-dimethylbarbituric acid (0.156 g, 1.0 mmol) and 7a (0.246 g, 1.0 mmol) in ethanol (6 ml) was heated to 80° C. and stirred for 20 hours. Ethanol was partially removed from reaction mixture by evaporation. To the residue was added water (10 ml). The suspension was stirred at 0° C. for 1 hour and then filtered. The solid was filtered, washed with water, washed with a mixture of hexanes:ethyl acetate, 8:2, and dried under vacuum to yield 7b, (78%, 0.3 g, 0.78 mmol).

Example 2-8

Synthesis of 5-((4-methoxynaphthalen-1-yl)methylene)pyrimidine-2,4,6(1H,3H,5H)-trione, 8b [BA-009]

A mixture of barbituric acid (0.128 g, 1.0 mmol) and 4-methoxy-1-naphthaldehyde (0.186 g, 1.0 mmol) in ethanol (4 ml) and acetic acid (0.5 ml) was heated to 80° C. and stirred for 20 hours. Ethanol was partially removed from reaction mixture by evaporation. To the residue was added $NH_4Cl$ aqueous saturated (10 ml). The suspension was stirred at 0° C. for 1 hour and then filtered. The solid was filtered, washed with water, washed with a mixture of hexanes:ethyl acetate, 8:2, and dried under vacuum to yield 8b, (65%, 0.192 g, 0.65 mmol).

Example 2-17

Synthesis of 5-((2,4-dimethoxynaphthalen-1-yl)methylene)-2-thioxodihydropyrimidine-4,6(1H,5H)-dione, 17c [BA-039]

17.a) Synthesis of 1,3-dimethoxynaphthalene, 17a

To a solution of 1,3-dihydroxynaphthalene (1 g, 6.25 mmol) in MeOH (20 mL), was added dimethyl sulfate (1.4 mL, 15 mmol) dropwise. The resulting mixture was refluxed overnight. The reaction solution was concentrated to give a oil which was diluted with 50 mL of dichloromethane and washed with 25% $NH_3$ aqueous. The organic layer was separated, dried (brine, sodium sulfate), evaporated and purified by chromatography (Petroleum ether: EtOA from 200:1 to 100:1) to give 1.1 g of 17a (93%) as colorless oil.

17,b) Synthesis of 2,4-dimethoxy-1-naphthaldehyde, 17b

To a solution of DMF (2.4 g, 32.7 mmol) in MeCN (150 mL) was added $POCl_3$ (2.03 mL, 21.8 mmol) dropwise at 0-5° C. The solution was stirred at reset temperature for 30 mins, then a solution of 9a (4.11 g, 21.8 mmol) in 20 mL of MeCN was added dropwise. The resulting mixture was stirred at r.t. overnight. The solvent was concentrated to give a solid that was dissolved in NaOH aqueous (5%, 100 mL) and stirred for 10 mins to cause precipitation. The resulting suspension was filtered to give 4 g of 17b (85%) as a white solid.

17.c) Synthesis of 5-((2,4-dimethoxynaphthalen-1-yl)methylene)-2-thioxodihydropyrimidine-4,6(1H,5H)-dione A solution of 17b (300 mg, 1.39 mmol) and 2-thioxodihydropyrimidine-4,6(1H,5H)-dione (200 mg, 1.39 mmol) in 50 mL EtOH was refluxed overnight. LC-MS showed 3 was consumed completely, then 100 mL of water was added to cause precipitate that was filtered and dried to give 210 mg of 17c (44%).

Example 2-18

Synthesis of 5-((2,4-dimethoxynaphthalen-1-yl)methylene)-1-methyl-2-thioxodihydropyrimidine-4,6(1H,5H)-dione, 18b [BA-040]

18.a) Synthesis of 1-methyl-2-thioxodihydropyrimidine-4,6(1H,5H)-dione, 18a

To a solution of EtONa (1.78 g, 26.3 mmol) in EtOH (20 mL) was added diethylmalonate (2 mL, 13.1 mmol) at 0-5° C. After stirring for 30 mins, 1-methylthiourea (1.18 g, 13.1 mmol) was added. The resulting mixture was refluxed overnight. LC-MS showed 1-methylthiourea was consumed. The reaction mixture was concentrated to give a residue that was dissolved in 10 mL of water. 5 mL of conc. HCl aqueous was added progressively into the mixture to cause precipitation of 10a (1.24 g, 60%), which was used without further purification.

18.b) Synthesis of 5-((2,4-dimethoxynaphthalen-1-yl)methylene)-1-methyl-2-thioxodihydropyrimidine-4,6(1H,5H)-dione, 18b A solution of 18a (220 mg, 1.39 mmol) and 17b (300 mg, 1.39 mmol) in 50 mL of EtOH was refluxed overnight. LC-MS showed 17b was consumed completely, then 50 mL of water was added to provide a precipitate, which was filtered out and dried in vacuum to give 100 mg of 18b (20%).

Example 2-19

Synthesis of 5-(2,4-dimethoxynaphthalen-1-yl)methylene)-1-phenyl-2-thioxodihydropyrimidine-4,6(1H,5H)-dione, 19c [BA-041]

19.a) Synthesis of 1-phenylthiourea, 18a

A solution of $NH_3$ (500 mg, 29.4 mmol) in 10 mL of dry dichloromethane was treated with 1 (1 g, 7.4 mmol). The solution was stirred at room temperature overnight, then concentrated to give 1.2 g of 19a, which was used without further purification.

19.b) 1-phenyl-2-thioxodihydropyrimidine-4,6(1H,5H)-dione, 19b

To a solution of EtONa (1.78 g, 26.3 mmol) in EtOH (20 mL) was added diethylmalonate (2 mL, 13.1 mmol) at 0-5° C. After stirring for 30 mins, 19a (2 g, 13.1 mmol) was added. The resulting mixture was refluxed overnight. LC-MS showed 19a was consumed. The reaction mixture was concentrated to give a residue, which was dissolved in 10 mL of water. 5 mL of conc. HCl aqueous was added progressively into the mixture to cause precipitation of 19b (1.5 g, 52%).

19.c) Synthesis of 5-((2,4-dimethoxynaphthalen-1-yl)methylene)-1-phenyl-2-thioxodihydropyrimidine-4,6(1H,5H)-dione, 19c A solution of 19b (200 mg, 0.91 mmol) and 17b (197 mg, 0.91 mmol) in 50 mL of EtOH was refluxed overnight. LC-MS showed 17b was consumed completely, then 50 mL of water was added to provide a precipitate, which was filtered out and dried in vacuum to give 270 mg of 19c (71%).

Example 2-20

Synthesis of 1-(4-methoxyphenyl)-4-(2-oxoindolin-3-ylidene)pyrazolidine-3,5-dione

20.a) Synthesis of ethyl 3-(2-(4-methoxyphenyl)hydrazinyl)-3-oxopropanoate, 20a Ethyl malonylchloride (0.83 g, 5.5 mmol) was added to a cold (−5° C.) solution of (4-methoxyphenyl)hydrazine (0.69 g, 5.0 mmol) and triethylamine (0.55 g, 5.5 mmol) in THF (5 ml). The reaction mixture was slowly warmed to room temperature and stirred overnight. The reaction mixture was washed with water and extracted with ethyl acetate. The organic layer was dried over $Na_2SO_4$, concentrated and purified by chromatography to yield 20a (0.65 g, 2.6 mmol, 51.6%).

20.b) Synthesis of 1-(4-methoxyphenyl)pyrazolidine-3,5-dione, 20b

A solution of 20a (0.504 g, 2 mmol) and NaOEt (0.204 g, 3 mmol) in EtOH (5 ml) was stirred at room temperature for 2 hours. The desired product was formed. The mixture was neutralized with acetic acid and concentrated to dryness. The solid residue was washed with water and extracted with dichloromethane. Organic layer was dried over $Na_2SO_4$, concentrated and purified by chromatography to yield 20b (0.31 g, 1.5 mmol, 75.2%).

20.c) A solution of 20b (0.21 g, 1 mmol), Isatin (0.15 g, 1 mmol), NaOEt (0.10 g, 1.5 mmol) in EtOH (5 ml) was heated to reflux for 4 hours.

Example 3

EMSA was Used to Quantify IC50 of Rel Inhibitors on Rel/NF-kB DNA Binding Activity Using the SAR strategy shown in FIG. 2A, analog libraries were screened and designed to further identify Rel inhibitors using both FP assays and electrophoretic mobility shift assay (EMSA). As an example, the $IC_{50}$ of several analogs was determined by quantifying the intensity of Rel/NF-kB inhibition in EMSA using phospho-imager (FIG. 3). Some c-Rel inhibitors not only interfere with c-Rel binding to DNA, but also inhibit other NF-kB member binding as well.

Based on the $IC_{50}$s from EMSA results, the c-Rel inhibitor analogs were rationally designed. FIG. 2B shows exemplary structures with Rel inhibitory activity based on the SAR strategy illustrated above.

Example 4

Tumor Cell Cytotoxicity Assay is Used to Select Active Rel Inhibitors

As described in the Background, multiple myelomas (MM) and diffuse large B cell lymphomas (DLBCL) exhibit persistent Rel activation attributed to mutations in the "classical" or the "alternative" Rel signaling pathways. During the course of the invention, it was found that although most MM and DLBCL cell lines express all five Rel members, they have differential dependence on the two Rel pathways for survival. For example, the "classical" Rel pathway is crucial for the survival of L363 cell line, whereas the "alternative" pathway is important for the survival of RPMI8226 cells.

The MM and DLBCL cell lines were used to test for tumor cell cytotoxicity by the Rel inhibitor analogs. As an example, three MM cell lines were treated with a Rel inhibitor for 48 hours and cell numbers were enumerated as percentage of control group. As shown in FIG. 4, MM cell lines have different response to growth inhibition by the Rel inhibitor. The L363 cells (with an active classical pathway) exhibit a dose-dependent apoptosis in response to the Rel inhibitors, such as BA001, whereas RPMI8226 cells (with an active alternative pathway) are quite resistant. MM1-144 cells, which use both pathways, are only partially inhibited by the Rel inhibitor.

FIG. 5 shows the effect of BA030 cRel inhibitor compound on DLBCL growth. The $IC_{50}$ was defined as the concentration that causes 50% cell death compared with control samples. $IC_{50}$ of BA030 on DLBCL cytotoxicity assay was found to be 4 µM. In summary, tumor cell lines were utilized to select for Rel inhibitors with tumor cytoxicity activities. Using these approaches, multiple Rel inhibitors were shown to exhibit anti-tumor cell proliferative activity in culture. Those compounds with in vitro anti-tumor activity were further tested in vivo using xenograft tumor models.

Example 5

Rel Inhibitors Exhibit Anti-Tumor Activity in Xenograft Tumor Models

Xenograft tumor models have been widely used to study human cancer. In this model, human tumor cells are transplanted, either under the skin or into the organ type in which the tumor originated, into immuno-compromised mice that do not reject human cells. The experiment used non-obese diabetic (NOD)/SCID mice for testing Rel inhibitor analogs.

Male NOD/SCID mice were injected with $3\text{-}5\times10^6$ of DLBCL tumor cells subcutaneously in each flank area. When tumors were palpable (~12 days after injection), the mice were randomized to receive either vehicle or test compounds corresponding to Rel inhibitors of the invention. In some experiments, DHMEQ was used as a benchmark compound. Compounds were administrated via i.p. at 12 to 24 mg/kg, three days per week for 2-3 weeks. Tumor volume was measured twice a week.

As an example, as shown by the graph in FIG. 6, mice treated with the Rel inhibitor (BA009, at 15 mg/kg) had significantly smaller tumor volume as compared to vehicle controls. In a separate example, as shown by the graph in FIG. 7, the Rel inhibitor (BA001, at 24 mg/Kg) slowed the tumor growth as compared to the vehicle controls.

As shown by the graph in FIG. 8, when BA001 was compared with the NF-kB inhibitor DHMEQ in DLBCL xenograft mouse model, BA001 (both 12 to 24 mg/kg doses) showed much better potency than DHMEQ. Administration with BA001 significantly slows down tumor growth as compared to DHMEQ treatment.

Example 6

Rel Inhibitors Inhibit the Expression of Inflammatory Cytokines

Since autoimmune diseases are associated with elevated levels of inflammatory cytokines, it is important to identify Rel inhibitors that can inhibit the expression of inflammatory cytokines. As c-Rel regulates the expression of several cytokines including IL-2, IFN-γ, and TNF, assays for these cytokines can be used to assess the anti-inflammatory effects of Rel inhibitor analogs. To perform such experiments, mouse splenocytes or human PBMCs were stimulated with anti-CD3+anti-CD28 for 6 hours to induce cytokine expression. Compounds were added at the beginning of the culture. Cytokines (IL-2, IFN-γ, and TNF) were measured by intracellular cytokine staining and flow cytometry and the % of cytokine-expressing cells within CD4+ T cell population was enumerated. Compounds at varying doses were tested.

The data shows that the Rel inhibitor (BA-001) inhibited IL-2, TNF, and IFN-γ expression at an $IC_{50}$ of ~6 uM (data not shown). By contrast, it had no inhibitory effects toward non-c-Rel target genes (e.g. CD69).

In yet another example, IL-2 expression was quantified by ELISA analysis. In these experiments, mouse splenocytes were stimulated with anti-CD3+anti-CD28, in the presence of varying doses of Rel inhibitors (from 0 to 20 µM). As shown by the results provided in FIGS. 9A and 9B, two c-Rel inhibitor analogs (BA001 and BA030) exhibited IL-2 inhibitory activity. The $IC_{50}$ of IL2 inhibition of BA030 found to be 0.4 µM, whereas $IC_{50}$ of BA001 was found to be 15 µM.

Example 7

Rel Inhibitors Reduced the Onset of EAE (Multiple Sclerosis) as Well as Prevented Streptozotocin (STZ)-Induced Diabetes in Animal Models Active Rel inhibitors with cytokine-inhibitory activity were further tested in inflammatory and autoimmune disease models in mice. As described in the Background, the c-Rel knockout mice were shown to be resistant to the development of a variety of inflammatory and autoimmune diseases, including Streptozotocin (STZ)-induced diabetes, EAE model (for human multiple sclerosis), collagen-induced arthritis, colitis, hepatitis, and atherosclerosis models. Thus, the Rel inhibitor analogs developed in this invention can be tested in the aforementioned disease models.

As an example, C57BL/6 mice were immunized to induce EAE with 1) a subcutaneous injection on flanks of 300 mg MOG38-50 peptide in 0.1 ml PBS emulsified in an equal volume of complete Freund's adjuvant containing 400 mg mycobacterium tuberculosis H37RA, and 2) an intravenous injection of 100 ng pertussis toxin in 0.1 ml PBS. A second injection of pertussis toxin (100 ng per mouse) was given 48 hr later.

Mice were subsequently injected i.p. with 300 µg BA-039 (n=4) or vehicle (n=3) daily beginning with the first day of EAE onset. Mice were monitored daily for disease score up to 16 days. The data demonstrate that, while mice treated with vehicle continue to get worse with disease score increases from 2 to 5, the mice treated with BA-039 have their disease score reduced from 2 to 1 (data not shown, manuscript in preparation). The data suggest that Rel inhibitor prevent the onset of EAE, a result consistent with earlier EAE studies in the c-Rel knockout mice.

In a second set of this experiment, treatment of the mice was stopped on the $16^{th}$ day of the study and further monitored for additional 22 days. The results showed a clear statistically significant difference between BA-039 and vehicle control groups in that the control group had an average disease score of 5 throughout the 22-day period. By contrast, the BA-039 treated group remained devoid of disease (average clinical score 1-2) (data not shown, manuscript in preparation). The data suggest that a transitory treatment of mice for 16 days at the onset of the EAE is sufficient to protect the mice from further deterioration even in the absence of continuous treatment. The data provide important information about treatment regimen with Rel inhibitors for multiple sclerosis patients in the future.

In yet another example, a Rel inhibitor compound was tested in Streptozotocin (STZ)-induced diabetes model. C57BL/6 (cRel+/+) mice were treated with low dose STZ for 5 days to induce diabetes, as indicated by glucose level above 300 mg/dl. c-Rel(−/−) mice were used as a control group. The Rel inhibitor (BA-001, 40 µg/mouse/day) or DMSO were injected IP to a group of five C57BL/6 mice for six consecutive days from day 0 to day 5. Glucose levels were determined at day 5, 7, 9, 12, 15, 19 and 27. The data showed that Rel inhibitor-treated C57BL/6 mice as well as the cRel(−/−) mice were resistant to STZ-induced diabetes (data not shown).

Example 8

Rel Inhibitors Reduce the Risk of Graft Versus Host Disease, but Preserving Anti-Tumor Activity, in Bone Marrow Transfer Tumor Models Earlier studies on c-Rel knockout mice have shown that blocking c-Rel in the host prevented rejection in heart and pancreatic islet cell transplant models. The benefit is due to inhibition of host T cell allo-reactivity. In a different clinical setting, the graft-versus-host (GVH) disease, a leading cause of death in leukemia patients receiving bone marrow or T cell therapies, is caused by allo-T cells that attack host tissues. The following test was devised to determine if c-Rel inhibition in allo-T cells or bone marrow dampens their GVH activity.

The GVH model is performed by transferring bone marrow, hematopoietic cells, or T cells derived from C57BL/6 mice to Balb/c mice (two strains of mice with different MHC types). Mouse survival is monitored daily, whereas clinical signs of GVHD are monitored weekly. Experimental readouts are survival, GVHD scores, and histopathology of GVHD target organs (skin, liver, intestine).

The first set of experiments were performed using c-Rel (−/−) T cells. The data showed that c-Rel(−/−) T cells, after transferring to recipient mice, did not cause GVHD. The mice receiving c-Rel(−/−) T cell transfer have prolonged survival, improved clinical and pathological. GVHD scores, as compared to mice receiving normal T cells. This correlates with impaired proliferation and activation of c-Rel(−/−) T cells.

In a second set of experiments, T cells were treated with Rel inhibitor ex vivo for 24 hours before transferring to the recipient mice. The mice receiving Rel inhibitor-treated T cells had prolonged survival and significantly reduced GVHD score and pathology, compared to mice receiving untreated T cells. This benefit correlates with its inhibitory effect on c-Rel and IL-2 expression. The mechanisms of Rel inhibition in diminishing GVHD are attributed to reduced proliferation and activation of T cells, shifting from Th1 to Th2 cytokine expression, and increased number of T-regulatory cells.

In a third set of experiments, the effect of Rel inhibitor on anti-tumor activity of transferred T cells is addressed. In this model, tumor cells were injected into recipient mice. The recipient mice were subsequently transferred with wild type T cells or c-Rel(−/−) T cells. The results showed that, although mice receiving wild type T cells had no signs of tumor growth (due to anti-tumor activity of infused T cells), unfortunately, a significant number of the mice died of GVHD. By contrast, the mice receiving c-Rel(−/−) T cells survived throughout the study and demonstrated reduced GHVD score. Most remarkably, tumor cells do not grow in these recipients. These data strongly suggest that, while c-Rel(−/−) T cells lose allo-reactivity, they still preserve anti-tumor activity.

Similar results were obtained when T cells were treated with Rel inhibitor beforehand ex vivo, instead of using c-Rel(−/−) T cells. Again, the mice receiving Rel inhibitor-treated T cells showed prolonged survival compared to control groups receiving untreated T cells. Furthermore, there are no residual tumor cells in the majority of mice receiving Rel inhibitor-treated T cells.

The data show significant clinical implication for CML and AML, where donor T cells are used for bone marrow reconstitution to achieve anti-leukemia therapeutic effects. The data strongly suggest clinical application for using Rel inhibitors to prevent Graft-versus-host disease (GVHD) while preserving the anti-tumor (GVT) effect. This is significant, since, in a clinical setting, doctors would like to reduce GVHD resulting from transplanted T cells while not affecting their anti-leukemic activity.

While there have been shown and described what are at present considered the preferred embodiments of the invention, those skilled in the art may make various changes and modifications which remain within the scope of the invention defined by the appended claims.

What is claimed is:

1. A method of treating leukemia in a subject, the method comprising transplanting bone marrow into said subject having leukemia and administering to said subject a pharmaceutically effective amount of a c-Rel activity inhibitor or a pharmaceutically acceptable salt or solvate thereof to reduce the level of transplant rejection of the subject to the transplanted bone marrow, wherein said c-Rel activity inhibitor has the formula:

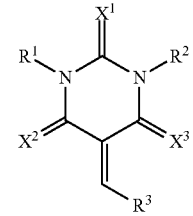

(1)

wherein $R^1$ and $R^2$ are each independently selected from hydrogen atom and hydrocarbon groups having at least one and up to thirty carbon atoms and optionally includes one or more heteroatoms selected from halogen, nitrogen, oxygen, and sulfur; $R^3$ is selected from hydrocarbon groups having at least one and up to thirty carbon atoms and optionally includes one or more heteroatoms selected from halogen, nitrogen, oxygen, and sulfur; and $X^1$, $X^2$, and $X^3$ are each independently selected from oxygen and sulfur atoms, provided that at least one of $X^1$, $X^2$, and $X^3$ is a sulfur atom.

2. The method of claim 1, wherein said leukemia is chronic lymphocytic leukemia.

3. The method of claim 1, wherein $R^3$ is a fused ring system.

4. The method of claim 1, provided that at least $X^1$ is a sulfur atom.

5. The method of claim 3, wherein said fused ring system is substituted with at least one alkoxy substituent.

6. The method of claim 3, provided that at least $X^1$ is a sulfur atom.

7. The method of claim 5, provided that at least $X^1$ is a sulfur atom.

8. The method of claim 3, wherein $R^3$ is a carbocyclic fused ring system.

9. The method of claim 8, provided that at least $X^1$ is a sulfur atom.

10. The method of claim 8, wherein said carbocyclic fused ring system is substituted with at least one alkoxy substituent.

11. The method of claim 10, provided that at least $X^1$ is a sulfur atom.

12. The method of claim 1, wherein said c-Rel activity inhibitor is selected from the group consisting of:
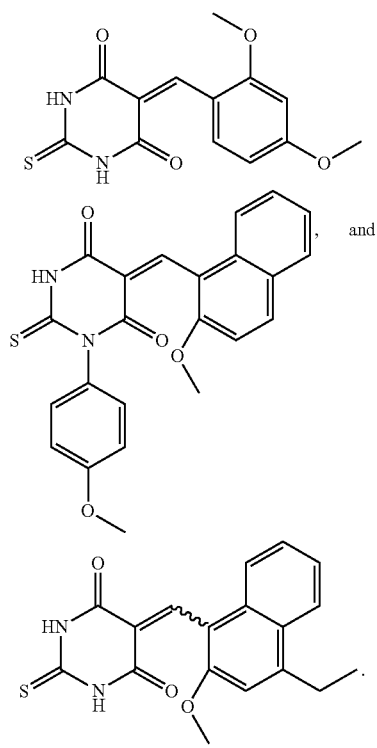
13. The method of claim 5, wherein said at least one alkoxy substituent is at least one methoxy substituent.
14. The method of claim 1, wherein said c-Rel activity inhibitor is selected from the group consisting of:
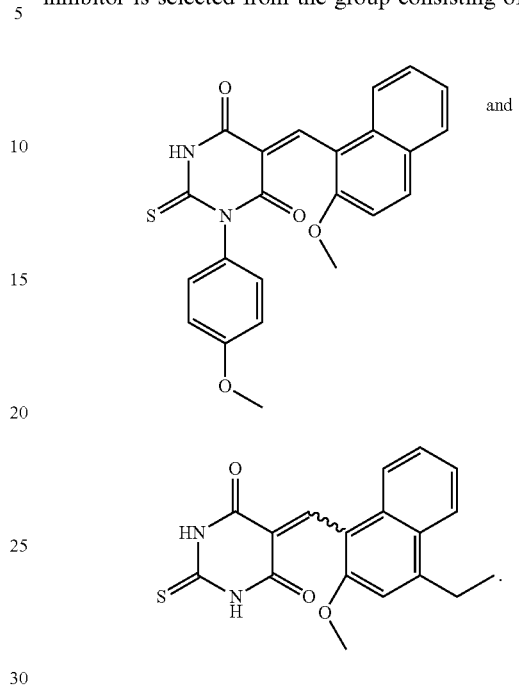
* * * * *